US007541043B2

(12) United States Patent
Kopecko et al.

(10) Patent No.: US 7,541,043 B2
(45) Date of Patent: Jun. 2, 2009

(54) **VACCINE FOR PROTECTION AGAINST *SHIGELLA SONNEI* DISEASE**

(75) Inventors: Dennis J. Kopecko, Silver Spring, MD (US); De-Qi Xu, Columbia, MD (US); John O. Cisar, Gaithersburg, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 617 days.

(21) Appl. No.: 10/346,706

(22) Filed: Jan. 15, 2003

(65) Prior Publication Data

US 2005/0281841 A1 Dec. 22, 2005

Related U.S. Application Data

(60) Provisional application No. 60/349,788, filed on Jan. 16, 2002.

(51) Int. Cl.
*A61K 39/112* (2006.01)
(52) U.S. Cl. ............... 424/258.1; 424/93.2; 424/93.48
(58) Field of Classification Search .................. None
See application file for complete search history.

(56) References Cited

U.S. PATENT DOCUMENTS

| 4,632,830 | A | * | 12/1986 | Formal et al. ............ 424/200.1 |
| 5,672,345 | A | | 9/1997 | Curtiss, III |
| 5,980,907 | A | | 11/1999 | Dougan et al. |
| 6,190,669 | B1 | | 2/2001 | Noriega et al. |

OTHER PUBLICATIONS

Keren et al. (Infect. Immun., 37:387-389, 1982).*
Viret et al. (Mol. Microbiol., 7:239-252, 1993).*
Bowie et al. (Science, 1990, 247:1306-1310).*
Burgess et al. (J. of Cell Bio. 111:2129-2138, 1990).*
Lazar et al. (Molecular and Cellular Biology, 1988, 8:1247-1252).*
Xu et al. (Abstract B-436, Abstracts of the 101st General Meeting of the American Society for Microbiology, May 2001).*
Galan et al. (Gene, 94:29-35, 1990).*
Belanger et al., "Functional analysis of genes responsible for the synthesis of the B- band O antigen of *Pseudomonas aeruginosa* serotype O6 lipopolysaccharide",. Microbiology. 145:3505-3521 (1999).
Bilge et al., "Role of the *Escherichia coli* O157:H7 O side chain in adherence and analysis of an rfb locus", Infect Immun. 64:4795-4801 (1996).
Black et al., "Prevention of shigellosis by a *Salmonella typhi-Shigella sonnei* bivalent vaccine", J Infect Dis. 155:1260-1265 (1987).
Burrows et al., "Functional conservation of the polysaccharide biosynthetic protein WbpM and its homologues in *Pseudomonas aeruginosa* and other medically significant bacteria" Infect Immun. 68:931-936 (2000).

Chida et al., "The complest DNA sequence of the O antigen gene region of *Plesiomonas shigelloides* serotype O17 which is identical to *Shigella sonnei* form I antigen", Microbiol Immunol. 44:161-172 (2000).
Creuzenet et al., "FlaA1, a new bifunctional UDP-GlcNAc C6 dehydratase / C4 reductase from *Helicobacter pylon*", J Biol Chem. 275:34873-34880 (2000).
DuPont et al., "Immunity in shigellosis. I. Response of man to attenuated straines of *Shigella*" J Infect Dis. 125:5-11 (1972).
Ertesvag et al., "Cloning and expression of an *Azotobacter vinelandii* mannuronan C-5- epimerase gene", J Bacteriol. 176:2846-2853 (1994).
Formal et al., "Construction of a potential bivalent vaccine strain: Introduction of *Shigella sonnei* form I antigen genes into the galE *Salmonella typhi* Ty21a typhoid vaccine strain", Infect Immun. 34:746-750.
Franklin et al., "*Pseudomonas aeruginosa* AlgG is a polym

OTHER PUBLICATIONS

Paulsen et al., "A family of gram-negative bacterial outer membrane factors that function in the export of proteins, carbohydrates, drugs and heavy metals from gram-negative bacteria", FEMS Microbiol Lett. 156:1-8 (1997).

Sansonetti et al., "*Shigella sonnei* plasmids: evidence that a large plasmid is necessary for virulence", Infect Immun. 34:75-83 (1981).

Seid et al., "Unusual lipopolysaccharide antigens of a *Salmonella typhi* oral vaccine strain expressing the *Shigella sonnei* form I antigen", J Biol Chem. 259:9028-9034 (1984).

Shepherd et al., "Comparison of O-antigen gene clusters of *Escherichia coli* (*Shigella*) *sonnei* and *Plesiomonas shigelloides* O17: sonnei gained its current plasmid-borne O-antigen genes from *P. shigelloides* in a recent event", Infect Immun. 68:6056-6061 (2000).

Stroeher et al., "A putative pathway for perosamine biosynthesis is the first function encoded within the rfb region of *Vibrio cholerae* O1". Gene. 166:33-42 (1995).

Van de Verg et al., "Specific immunoglobulin A-secreting cells in peripheral blood of humans following oral immunization with a bivalent *Salmonella typhi-Shigella sonnei* vaccine or infection by pathogenic *S. sonnei.*" Infect Immun. 58:2002-2004 (1990).

Viret et al., "Molecular cloning and characterization of the genetic determinants that express the complete *Shigella* serotype D (*Shigella sonnei*) lipopolysaccharide in heterologous live attenuated vaccine strains", Mol Microbiol. 7:239-252 (1993).

Wang et al., "Expression of the O antigen gene cluster is regulated by RfaH through the JUMPstart sequence. FEMS", Microbiol Lett. 165:201-206 (1998).

Whitfield et al., "Structure, assembly and regulation of expression of capsules in *Escherichia coli.* Mol" Microbiol. 31:1307-1319 (1999).

Yoshida et al., "Molecular cloning and characterization of form I antigen genes of *Shigella sonnei*", J Gen Microbiol. 137:867-874 (1991).

Zhao et al., "WbpO, a UDP-N-Acetyl-D-galactosamine dehydrogenase from *Pseudomonas aeruginosa* serotype O6", J Biol Chem. 275:33252-33259 (2000).

* cited by examiner

VACCINE FOR PROTECTION AGAINST *SHIGELLA SONNEI* DISEASE

STATEMENT AS TO RIGHTS TO INVENTIONS MADE UNDER FEDERALLY SPONSORED RESEARCH AND DEVELOPMENT

This invention is owned by the United States Government.

FIELD OF THE INVENTION

This invention relates to the field of vaccines for treating and preventing bacillary dysentery. In particular, this invention provides for attenuated live bacteria expressing the *Shigella sonnei* form I-O polysaccharide that are useful for inducing an immunoprotective response against *Shigella sonnei*.

BACKGROUND OF THE INVENTION

Bacillary dysentery and specifically shigellosis is a global human health problem. It has been over 100 years since the discovery of Shiga's *bacillus*, yet shigellosis remains endemic in most areas of the world including industrialized nations. An estimated 200 million people worldwide suffer from shigellosis, with more than 650,000 associated deaths annually (27). A recent CDC estimate indicates the occurrence of over 440,000 annual shigellosis cases in the United States alone (32), approximately 80% of which are caused by *Shigella sonnei*. All virulent *S. sonnei* strains comprise a single serotype determined by form I O-polysaccharide (O-Ps). This O-Ps is composed of a disaccharide repeating unit containing two unusual amino sugars, 2-amino-2-deoxy-L-altruronic acid (L-AltNAcA) and 2-acetamido-4-amino-2,4,6-trideoxy-D-galactose (4-n-D-FucNAc) (25). The genes encoding the enzymes that produce this O-Ps are novelly located on the 180 kb virulence plasmid in *S. sonnei* (26), which also harbors the invasion genes (36). Virulent form I colonies are typically unstable and upon replating convert to rough colonies, termed form II, due primarily to spontaneous loss of the large virulence plasmid and the ensuing loss of form I O-antigen. Substantially identical genes that encode the same antigen producing enzymes are located on the bacterial chromosome in *Plesiomonas shigelloides* (termed the O17 gene cluster).

Immunity to Shigellae, acquired either by natural infection or volunteer challenge, is mediated largely by immune responses directed against the serotype specific O-Ps (9, 10). This insight has led to the development of a variety of candidate vaccines containing *Shigella* O-Ps for oral or parenteral administration including recombinant heterologous, live, bacterial carrier strains (3, 12, 18). Parenteral vaccines in the past have not been effective in protecting against bacillary dysentery because shigellosis is an infection limited to the superficial layer of the colonic mucosa. It is, therefore, not surprising that attempts to immunize man or other primates with killed whole cell *Shigella* vaccines, administered by the parenteral route, have not been successful.

In early recombinant vaccine efforts, the virulence plasmid of *S. sonnei* was transferred as part of a larger plasmid cointegrate to the attenuated vector *Salmonella enterica* serovar *Typhi* strain Ty21a (i.e. *S. Typhi* Ty21a) (12). The resulting hybrid vaccine strain, 5076-1C, expressed *S. sonnei* O antigen as a lipid-linked surface O-Ps as well as *S. Typhi* 9,12 LPS (37). Although not core-linked, this form I O-Ps was immunogenic (12) and oral immunization of volunteers with 5076-1C elicited protection against virulent *S. sonnei* oral challenge (3, 21, 40). However, the protection observed in volunteers was variable, presumably due to loss of the form I gene region from the large cointegrate plasmid in 5076-1C (17). Thus, further molecular studies are needed to stabilize the *S. sonnei* form I gene region in vaccine vector constructs. In spite of an increased molecular understanding of *Shigella* pathogenesis, there are still no licensed vaccines for protection against shigellosis in the United States.

Although the form I O-Ps-encoding locus has been studied in some detail previously (6, 24, 38, 42, 45) the biosynthetic pathway and minimal gene region for stable expression of O-antigen have not been unambiguously defined. We show through deletion and sequence analyses and LPS expression studies that the *S. sonnei* form I biosynthetic gene region comprises a 12.3 kb operon. A detailed biosynthetic pathway, based on DNA sequence analysis of this region and the known structure of form I O-Ps, is proposed. In addition, stable expression of form I O-Ps was observed from a low copy plasmid and was associated with the removal of an adjacent IS91 resulting in small, genetically stable form I gene region constructs. We report the development and animal testing of a live attenuated *S. Typhi* vaccine vector stably expressing enzymes that produce form I O-Ps for protection against *S. sonnei* disease.

To develop a more stable living attenuated oral *Shigella* strain vaccine, the gene region encoding the enzymes that produce form I antigen was isolated from a large non-conjugative plasmid and analyzed to determine the essential genes required for biosynthesis of *Shigella sonnei* form I O-polysaccharide. Nucleic acids totaling 18 kb, were characterized genetically and used to define a minimal region encoding all of the proteins required to produce the form I antigen for development of live vaccine vector strains. Constructs comprising a 12.2 kb region encoding a consensus promoter and ten contiguous ORF's, and additional flanking DNA were generated which contained all of the information required to produce the *Shigella* form I O-Ps antigen. Significantly, attenuated *Salmonella enterica* serovar *Typhi* live vector vaccine candidate strains, containing minimal-sized form I O-Ps operon constructs, elicited immune protection in mice against virulent *S. sonnei* challenge.

BRIEF SUMMARY OF THE INVENTION

In one aspect of the invention, an immunoprotective composition containing an attenuated bacteria capable of expressing an antigen useful for inducing an immunoprotective response against *Shigella sonnei* (*S. sonnei*) is prepared. The antigen comprises the *S. sonnei* form I O-polysaccharide and the antigen is produced by enzymes encoded by an expression cassette containing a nucleotide fragment comprising the genes wbgT, wbgU, wzx, wzy, wbgV, wbgW, wbgX, wbgY, and wbgZ isolated from the *S. sonnei* rfb/rfc gene cluster or *Plesiomonas shigelloides* (*P. shigelloides*) O17 gene cluster which are operably linked to transcriptional promoter and termination signals. The gene containing fragment is between 10,000 and 13,700 nucleotides in length. The expression cassette containing the fragment does not include sequences that naturally flank the rfb/rfc gene cluster.

In another aspect of the invention, the attenuated bacteria in the immunoprotective composition are selected from the group consisting of *Campylobacter jejuni*, *Campylobacter coli*, *Listeria monocytogenes*, *Yersinia enterocolitica*, *Yersinia pestis*, *Yersinia pseudotuberculosis*, *Escherichia coli*, *Shigella flexneri*, *Shigella sonnei*, *Shigella dysenteriae*, *Shigella boydii*, *Helicobacter pylori*, *Helicobacter felis*, *Gastrospirillum hominus*, *Vibrio cholerae*, *Vibrio parahaemolyti-* cus, *Vibrio vulnificus, Bacteroides fragilis, Clostridium difficile, Salmonella typhimurium, Salmonella typhi, Salmonella gallinarum, Salmonella pullorum, Salmonella choleraesuis, Salmonella enteritidis, Streptococcus gordonii, Lactobacillis* sp., *Klebsiella pneumoniae, Enterobacter cloacae,* and *Enterococcus faecalis.*

In one embodiment of the invention, the attenuated bacteria are *E. coli* bacteria selected from the group consisting of the strains DH5α and HB101. In another embodiment of the invention, the attenuated bacteria are *S. typhi* bacteria selected from the group consisting of the strains Ty21a, CVD 908, CVD 908-htrA, X4073 and Ty800. In a particularly preferred embodiment, the attenuated *S. typhi* bacteria are the attenuated strain of Ty2. In another embodiment, the attenuated bacteria are *S. sonnei* bacteria selected from the group consisting of strains 53GI and 53GII.

In one aspect of the invention, the gene containing fragment in the immunoprotective composition comprises SEQ ID NO:2, SEQ ID NO:3, or SEQ ID NO:4 operably linked to a promoter.

In another aspect of the invention, the gene containing fragment of the immunoprotective composition lacks SEQ ID NO:15.

In still another aspect of the invention the enzymes that produce the antigen are expressed from a recombinant plasmid. In one embodiment of the invention, the recombinant plasmid contains a selectable marker. In a preferred embodiment, the selectable marker is the aspartate β-semialdehyde dehydrogenase (asd) gene operably linked to a promoter. In still another embodiment of the invention, the enzymes that produce the antigen are encoded by a recombinant plasmid containing SEQ ID NO: 2, SEQ ID NO: 3, or SEQ ID NO: 4 operably linked to a promoter. In yet another embodiment of the invention, the recombinant plasmid lacks SEQ ID NO:15. In one embodiment, the recombinant plasmid comprises SEQ ID NO: 2 operably linked to a promoter. In another embodiment, the recombinant plasmid comprises SEQ ID NO: 3 operably linked to a promoter. In still another embodiment, the recombinant plasmid comprises SEQ ID NO: 4 operably linked to a promoter.

In another aspect of the invention, the immunoprotective composition also contains a pharmaceutical diluent.

The invention provides for a method of protecting a susceptible host against an infection of *Shigella sonnei* (*S. sonnei*) by administering to the host an immunoprotective composition containing an attenuated bacteria capable of expressing an antigen useful for inducing an immunoprotective response against *Shigella sonnei* (*S. sonnei*), where the antigen comprises the *S. sonnei* form I O-polysaccharide, the antigen is produced by enzymes encoded by an expression cassette containing a nucleotide fragment comprising the genes wbgT, wbgU, wzx, wzy, wbgV, wbgW, wbgX, wbgY, and wbgZ isolated from the *S. sonnei* rfb/rfc gene cluster or *Plesiomonas shigelloides* (*P. shigelloides*) O17 gene cluster which are operably linked to transcriptional promoter and termination signals, the gene containing fragment is between 10,000 and 13,700 nucleotides in length, the expression cassette containing the fragment does not include sequences that naturally flank the rfb/rfc gene cluster, and the composition is given in an amount sufficient to invoke an immunoprotective response in the host.

In another aspect the invention provides a method of protecting a susceptible host against an infection of *Shigella sonnei* (*S. sonnei*) comprising administering to said host an immunoprotective composition containing an attenuated bacteria capable of expressing an antigen useful for inducing an immunoprotective response against *Shigella sonnei* (*S. sonnei*), where the antigen comprises the *S. sonnei* form I O-polysaccharide, the antigen is produced by enzymes encoded by an expression cassette containing a nucleotide fragment comprising the genes wbgT, wbgU, wzx, wzy, wbgV, wbgW, wbgX, wbgY, and wbgZ isolated from the *S. sonnei* rfb/rfc gene cluster or *Plesiomonas shigelloides* (*P. shigelloides*) O17 gene cluster which are operably linked to transcriptional promoter and termination signals, the gene containing fragment is between 10,000 and 13,700 nucleotides in length, the expression cassette containing the fragment does not include sequences that naturally flank the rfb/rfc gene cluster, the expression cassette is on a recombinant plasmid, and the immunogenic composition is given in an amount sufficient to invoke an immunoprotective response in the host. In one embodiment of the method, the enzymes that produce the antigen are encoded by a recombinant plasmid containing SEQ ID NO: 2, SEQ ID NO: 3, or SEQ ID NO: 4 operably linked to a promoter. In another embodiment of the method, the immunogenic composition is in a pharmaceutically acceptable carrier. In still another embodiment of the method, the immunogenic composition is in a sterile medium. In another embodiment of the method, the immunogenic composition also contains an adjuvant.

Definitions

Figure 1:
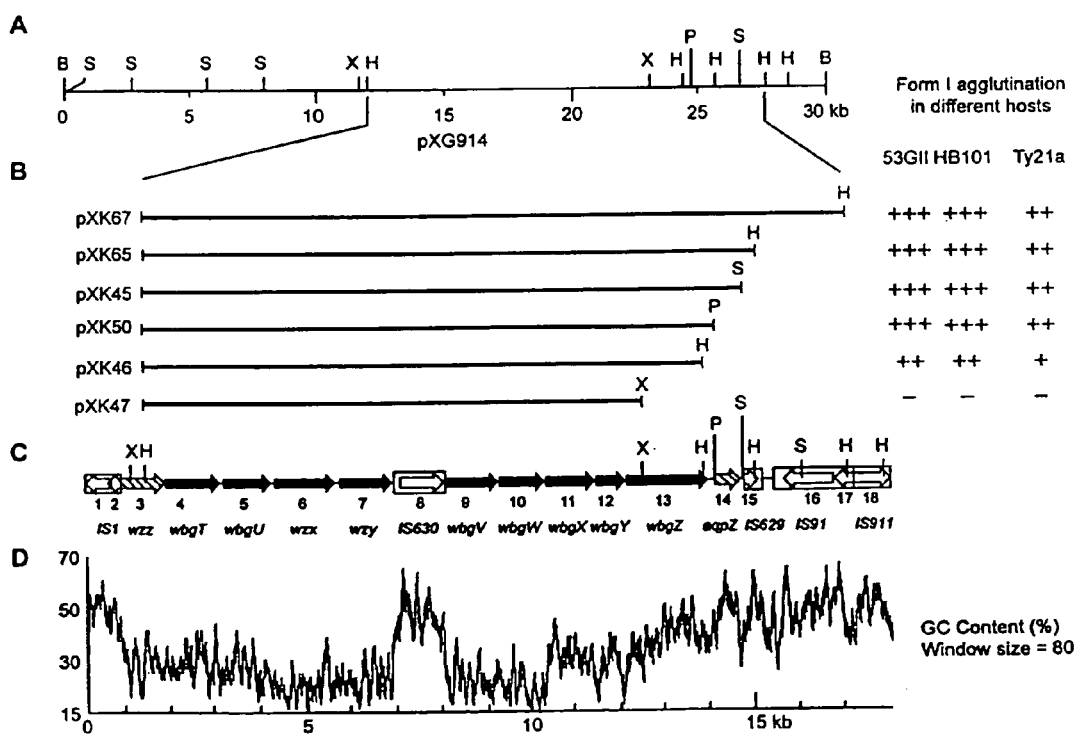
FIG. 1. Cloning and downsizing of the *S. sonnei* form I biosynthetic gene cluster for sequencing and O-antigen expression studies. (A) Restriction map of the 30 kb BamH1 insert from cosmid pXG914. (B) The inserts of plasmid subclones prepared to define a minimal essential region for form I O-antigen expression, defined by anti-form I specific bacterial agglutination of recipient *S. sonnei* 53GII. *E. coli* HB101, or *S. Typhi* Ty21a carrying each of these plasmids. (C) Map of the form I gene region showing restriction sites relative to inserts shown in panel B and the location of 18 ORFs identified by sequence analysis. Filled ORFs represent the genes required for form I O-Ps biosynthesis in plasmid bearing subclones. Restriction endonuclease sites are shown for BamHI (B), HindIII (H), PmeI (P), SmaI (S), and XbaI (X). (>) Percent GC content of the 17,986 bp form I biosynthetic region and flanking sequences.

The term "operon" refers to a cluster of functionally related genes whose expression or operation is regulated by the same preceeding promoter gene.

The term "rfb/rfc" is the gene symbol for the gene cluster which encodes all of the proteins required to synthesize, polymerize, and transport to the bacterial surface the form I O-Polysaccharide of *Shigella sonnei*. The rfb/rfc gene cluster comprises the genes wbgT, wbgU, wzx, wzy, wbgV, wbgW, wbgX, wbgY, and wbgZ (see Table 2 and SEQ ID NO:7). Included in the cluster but not required for production of the form I O-Ps is the transposable element IS630 (SEQ ID NO:15). Also included in the gene cluster are the promoter and operator sequences (SEQ ID NO:12) for the gene cluster located in the carboxyterminus of the wzz gene immediately upstream (5') of the wbgT gene, and the transcriptional terminator sequences are located immediately downstream (3') of the wbgZ gene (SEQ ID NO:13). Sequences which naturally flank the rfb/rfc gene cluster include those sequences found on the *S. sonnei* virulence plasmid containing the rfb/rfc gene cluster not contained in SEQ ID NO:2.

The term "form I O-Polysaccharide" refers to the *Shigella sonnei* O antigen composed of disaccharide repeating units containing two unusual amino sugars, 2-amino-2-deoxy-L-alturonic acid (L-AltNAcA) and 2-acetamido-4-amino-2,4,6-trideoxy-D-galactose (4-nD-FucNAc).

The term "form I O-Ps" is a short hand designation for and used interchangeably herein for the *Shigella sonnei* form I O-Polysaccharide surface antigen.

The term "O17 gene cluster" is the name of the gene cluster isolated from *Plesiomonas shigelloides* (*P. shigelloides*) encoding the the genes wbgT, wbgU wzx, wzy, wbgV, wbgW, wbgX, wbgY, and wbgZ (SEQ ID NO:17). The genes are located in an operon on the bacterial chromosome. The O17 gene cluster is substantially identical to the rfb/rfc gene cluster. The nucloetide sequence identity between the clusters ranges from 95% to 100% depending on the gene. The amino acid sequence identity ranges from 98% to 100%, depending on the gene and the amino acid sequence similarity ranges from 99% to 100% depending on the gene. The O17 gene cluster lacks the IS630 transposable element found in the rb/rfc gene cluster. The genes encoded by the O17 gene cluster produce the same enzymes and are capable of producing the same form I O-Ps surface antigen as the rfb/rfc gene cluster. Sequences which naturally flank the O17 gene cluster include those sequences found on the *P. shigelloides* bacterial chromosome which are not substantially identical the sequences contained in SEQ ID NO:4.

The term "attenuated," when used with respect to a bacteria, means that the bacteria has lost some or all of its ability to proliferate and/or cause disease or other adverse effect when the bacteria infects an organism. For example, an "attenuated" bacteria can be unable to replicate at all, or be limited to one or a few rounds of replication, when present in an organism in which a wild-type or other pathogenic version of the attenuated bacteria can replicate. Alternatively or additionally, an "attenuated" bacteria might have one or more mutations in a gene or genes that are involved in pathogenicity of the bacteria. Many genes, loci, or operons are known, mutations in which will result in an attenuated bacteria. Examples of attenuated bacteria used as live vaccines include *S. typhi* carrying a mutation in its galE or htrA gene, and *V. cholerae* carrying mutations in its ctxA gene.

A "host organism" is an animal that is a target of vaccination with the attenuated vaccines of the invention. Such host organisms have an immune system that is responsive to inoculation with an immunogen. Suitable host organisms include, for example, humans, rodents, livestock, birds, and other animals in which it is desirable to vaccinate for either therapeutic or prophylactic purposes.

The term "vaccine," is used interchangeably herein with "immunoprotective composition" and as used herein, refers to an immunogen that, upon inoculation into a host organism, can induce complete or partial immunity to pathogenic agents, or can reduce the effects of diseases associated with pathogenic agents.

The terms "nucleic acid" or "oligonucleotide" or grammatical equivalents herein refer to at least two nucleotides covalently linked together. The term nucleic acid is used interchangeably with gene, cDNA, and mRNA encoded by a gene. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nuc. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 141 9), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research,* Ed. Y. S. Sanghui and P. Dan Cook. Nucleic acids containing one or more carbocyclic sugars are also included within the definition of nucleic acids (see Jenkins et al. (1995), *Chem. Soc. Rev.* pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

A "exogenous DNA segment", "heterologous sequence" or a "heterologous nucleic acid", as used herein, is one that originates from a source foreign to the particular host cell, or, if from the same source, is modified from its original form. Thus, a heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

The term "gene" is used broadly to refer to any segment of DNA associated with a biological function. Thus, genes include coding sequences and/or the regulatory sequences required for their expression. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids (typically less than 5%, more typically less than 1%) in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 15 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units.

The term "isolated", when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to essentially one band in an electrophoretic gel. Particularly, it means that the nucleic acid or protein is at least about 50% pure, more preferably at least about 85% pure, and most preferably at least about 99% pure.

The term "naturally-occurring" is used to describe an object that can be found in nature as distinct from being artificially produced by man. For example, an organism, or a polypeptide or polynucleotide sequence that is present in an organism (including viruses, bacteria, protozoa, insects, plants or mammalian tissue) that can be isolated from a source in nature and which has not been intentionally modified by man in the laboratory is naturally-occurring.

"Nucleic acid derived from a gene" refers to a nucleic acid for whose synthesis the gene, or a subsequence thereof, has ultimately served as a template. Thus, an mRNA, a cDNA reverse transcribed from an mRNA, an RNA transcribed from that cDNA, a DNA amplified from the cDNA, an RNA transcribed from the amplified DNA, etc., are all derived from the gene and detection of such derived products is indicative of the presence and/or abundance of the original gene and/or gene transcript in a sample.

A nucleic acid is "operably linked" when it is placed into a functional relationship with another nucleic acid sequence. For instance, a promoter or enhancer is operably linked to a coding sequence if it increases the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

The term "recombinant" when used with reference to a bacteria indicates that the host bacteria contains a heterologous nucleic acid, or expresses a peptide or protein encoded by a heterologous nucleic acid. Heterologous nucleic acids can integrate into the host bacteria chromosome and be expressed from host or heterologous promoters. Alternatively, heterologous nucleic acids can be expressed from an autonomously replicating plasmid. Recombinant bacteria can contain genes that are not found within the native (non-recombinant) form of the bacteria. Recombinant bacteria can also contain genes found in the native form of the bacteria wherein the genes are modified and re-introduced into the cell by artificial means. The term also encompasses bacteria that contain a nucleic acid endogenous to the bacteria that has been modified without removing the nucleic acid from the bacteria; such modifications include those obtained by gene replacement, site-specific mutation, and related techniques.

A "recombinant expression cassette" or simply an "expression cassette" is a nucleic acid construct, generated recombinantly or synthetically, with nucleic acid elements that are capable of effecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide or series of peptides), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette. The recombinant expression cassette may be located on an autonomously replicating plasmid or may be integrated into the host genome.

The term "selectable marker" refers to a nucleotide sequence that encodes a protein and that confers either a positive or negative selective advantage to a bacteria expressing that marker. For example, an expression cassette comprising a selectable marker could comprise the aspartate β-semialdehyde dehydrogenase (asd) gene operably linked to a promoter. A recombinant plasmid capable of expressing asd could complement the asd phenotype of asd deletion mutants. Bacteria lacking asd would not be able to synthesize diaminopimelic acid, an essential element of the peptidoglycan of the bacterial cell wall, and would die. Examples of other selectable markers useful in bacteria include SacB, aroA, and heavy metal ion resistance genes.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90-95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., *Current Protocols in Molecular Biology*, John Wiley and Sons Inc. New York, N.Y. (2001)).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (http://www.ncbi.nlm.nih.gov/).

A "subsequence" refers to a sequence of nucleic acids or amino acids that comprise a part of a longer sequence of nucleic acids or amino acids (e.g., polypeptide) respectively.

The term "protective immunity" means that a vaccine or immunization schedule that is administered to a mammal induces an immune response that prevents, retards the development of, or reduces the severity of a disease or infection that is caused by *Shigella sonnei*, or diminishes or altogether eliminates the symptoms of the disease or infection.

The phrase "sufficient to invoke an immunoprotective response" means that there is a detectable difference between an immune response indicator measured before and after administration of a particular antigen preparation. Immune response indicators include but are not limited to: antibody titer or specificity, as detected by an assay such as enzyme-linked immunoassay (ELISA), bactericidal assay, flow cytometry, immunoprecipitation, Ouchter-Lowny immunodiffusion; binding detection assays of, for example, spot, Western blot or antigen arrays; cytotoxicity assays, etc.

A "surface antigen" is an antigen that is present in a surface structure of a bacteria such as the *Shigella sonnei* form I O-Ps antigen, which is capable of generating an immunoprotective response when expressed by a recombinant bacteria and presented to a host organism in an immunoprotective composition.

DETAILED DESCRIPTION OF THE INVENTION

This invention is directed to a living, attenuated, oral vaccine capable of inducing an immunoprotective response against *Shigella sonnei*. The invention is based on an attenuated strain of bacteria which has been genetically engineered to carry the genes encoding the enzymes capable of synthesizing the *S. sonnei* form I O-Ps antigen. These recombinant bacteria are useful in an immunoprotective composition to induce an immunoprotective response in a susceptible host organism. In addition to infections caused by *S. sonnei*, enteric infections caused by other organisms are considered amenable to treatment with a combination vaccine according to this invention. For example, genes encoding the surface antigens derived from other *Shigella* strains such as *S. flexneri*, *S. dysenteriae*, and *S. boydii* (see e.g., Baron et al., *Infect. and Immun.* 55:2797 (1987)) can be transferred into recipient bacteria independently of or concurrently with the *S. sonnei* rfb/rfc gene cluster. The resulting recombinant bacteria can then express two or more heterologous surface antigens suitable for generating an immunoprotective response in a host organism. Alternatively, the oral vaccine may contain multiple strains of attenuated bacteria, each strain expressing a different heterologous antigen. This resulting vaccine would also be suitable for generating an immunoprotective response against multiple antigens in a host organism.

Genes encoding other antigens, such as *Salmonella typhi* Vi antigen and genes encoding non-toxic variants of toxins derived from enterotoxogenic strains such as *Escherichia coli*, *Vibrio cholera*, and *Yersinia* can also be transferred independently of or concurrently with the *S. sonnei* rfb/rfc gene cluster into bacterial hosts (see e.g. U.S. Pat. No. 4,632, 830). In a preferred embodiment, the Vi antigen or non-toxic variants of the enterotoxins should be expressed in such a way that the proteins are present on the surface of the recombinant bacteria or secreted by the recombinant bacteria. The resulting recombinant bacteria would be useful in immunogenic compositions for generating an immunoprotective response to these additional antigens. Enteric disease caused by bacterial secretion of an exotoxin exemplified by staphylococcal, clostridial or similar food poisoning are also considered amenable to treatment with an immunoprotective composition according to this invention using an approach similar to the approach used for enterotoxins.

Nucleic acids encoding the *S. sonnei* rfb/rfc gene cluster as exemplified in SEQ ID NO:2-4, the O17 gene cluster, or other antigens are typically cloned into vectors for transformation into bacterial cells for replication, expression, and cell transformation. Such vectors are typically prokaryotic vectors, e.g., plasmids that act as shuttle vectors, or for production of protein. The elements that are typically included in vectors include a replicon that functions in the recombinant bacteria, a gene encoding a selectable marker to permit selection of bacteria that harbor recombinant plasmids, and unique restriction sites in nonessential regions of the plasmid to allow insertion of recombinant sequences. Selectable markers may include a gene encoding antibiotic resistance, or may include a gene encoding a protein whose naturally occuring gene has been mutated resulting in an attenuated strain of bacteria. Examples of suitable targets for mutation include genes that would result in essential auxotrophic pathways, loci encoding regulons that exert pleiotropic effects such as the cya/crp system, the ompR/envZ system or the phoP system (see e.g. U.S. Pat. Nos. 5,672,345, 5,980,907, 6,190,669). A preferred selectable marker is the aspartate β-semialdehyde dehydrogenase (asd) gene operably linked to a promoter. A recombinant plasmid capable of expressing asd could complement the asd phenotype of attenuated bacterial strains suitable for use in vaccines and containing asd deletion mutantations. Bacteria lacking asd would not be able to synthesize diaminopimelic acid, an essential element of the peptidoglycan of the bacterial cell wall, and would die. Examples of other selectable markers useful in bacteria include SacB, aroA, and heavy metal ion resistance genes.

Alternatively, vectors containing nucleic acids encoding the enzymes that produce the form I O-Ps antigen may be transformed into bacterial cells carrying a mutation in the msbB gene. Mutations in this gene fail to myristylate lipid A. Bacteria containing this mutation may contain additional mutations resulting in attenuated bacteria and vectors containing the enzymes that produce the form I O-Ps may contain selectable markers. Form I O-Ps produced in bacteria containing a mutation in the msbB gene may be purified using techniques well known to those of skill in the art and used in an immunoprotective composition directly.

To obtain expression of the *S. sonnei* rfb/rfc gene cluster, the O17 gene cluster, or other antigens, the nucleic acids encoding the appropriate gene(s) are typically subcloned using techniques well known to those of skill in the art, into an expression vector that contains a promoter to direct transcription. Suitable bacterial promoters are well known in the art and described, e.g., in Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 2001).

The promoter used to direct expression of the *S. sonnei* rfb/rfc gene cluster, the O17 gene cluster, or other antigen depends on the particular application. Either a constitutive or an inducible promoter may be used. Preferably, a constitutive promoter is used. Alternatively, the promoter which drives the normal expression of the *S. sonnei* rfb/rfc gene cluster can be used.

The promoter typically can also include elements that are responsive to transactivation, e.g., hypoxia response elements, Gal4 response elements, lac repressor response element, and small molecule control systems such as tet-regulated systems and the like (see, e.g., Gossen & Bujard, *Proc. Nat'l Acad. Sci. USA* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)).

In addition to the promoter, the expression vector typically contains a transcription unit or expression cassette that contains all the additional elements required for the expression of the nucleic acid in recombinant bacteria A typical expression cassette thus contains a promoter operably linked, e.g., to the nucleic acid sequence encoding the rfb/rfc gene cluster, and signals required, e.g., for transcriptional termination, ribosome binding sites, or translation termination. Additional elements of the cassette may include, e.g., regulatory proteins.

Standard bacterial vectors include plasmids such as pBR322 based plasmids, pBR325, pUC18, pSKF, pET23D, and pBR322 based cosmid vectors such as pHC79 and pCVD551. Vectors based on the bacterial plasmid pSC101 such as pGB-2 may also be used.

Standard transformation methods are used to produce bacterial cell lines that express the surface antigen proteins of the invention. Transformation of prokaryotic cells are performed according to standard techniques (see, e.g., Morrison, *J. Bact.* 132:349-351 (1977); Sambrook et al. supra; Ausubel et al. supra). These methods include microinjection, ballistics, use of calcium chloride transformation, infection, conjugation, and electroporation of plasmid vectors, both episomal and integrative, and any of the other well known methods for introducing cloned genomic DNA, synthetic DNA or other foreign genetic material into a recombinant bacteria (see, e.g., Sambrook et al., supra, see also U.S. Pat. No. 5,049,386, U.S. Pat. No. 4,946,787; U.S. Pat. No. 4,897,355; WO 91/17424, and WO 91/16024). It is only necessary that the particular genetic engineering procedure used be capable of successfully introducing at least one gene into the recombinant bacteria capable of expressing the protein of choice.

The microorganisms which are used to express the *S. sonnei* rfb/rfc gene cluster, the O17 gene cluster and other antigens for use in immunoprotective compositions include without limitation, *Campylobacter* sp., *Yersinia* sp., *Helicobacter* sp., *Gastrospirillum* sp., *Bacteroides* sp., *Klebsiella* sp., *Lactobacillis* sp., *Streptococcus gordonii, Enterobacter* sp., *Salmonella* sp., *Shigella* sp., *Aeromonas* sp., *Vibrio* sp., *Clostridium* sp., *Enterococcus* sp. and *Escherichia coli* (see e.g. U.S. Pat. Nos. 5,858,352, and 6,051,416, and Levine et al., in "New Generation Vaccines Second Edition" ed. Levine et al., Marcel Dekker, Inc. pp 351-361 (1997), Levine et al., in "New Generation Vaccines Second Edition" ed. Levine et al., Marcel Dekker, Inc. pp 437-446 (1997), Butterton et al., in "New Generation Vaccines Second Edition" ed. Levine et al., Marcel Dekker, Inc. pp 379-385 (1997) and Fennelly et al., in "New Generation Vaccines Second Edition" ed. Levine et al., Marcel Dekker, Inc. pp 363-377 (1997)).

Preferred enteric bacteria that the various aspects of the present invention relate to are *Campylobacter jejuni, Campylobacter coli, Listeria monocytogenes, Yersinia enterocolitica, Yersinia pestis, Yersinia pseudotuberculosis, Escherichia coli, Shigella flexneri, Shigella sonnei, Shigella dysenteriae, Shigella boydii, Helicobacter pylori, Helicobacter felis, Gastrospirillum hominus, Vibrio cholerae, Vibrio parahaemolyticus, Vibrio vulnificus, Bacteroides fragilis, Clostridium difficile, Salmonella typhimurium, Salmonella typhi, Salmonella gallinarum, Salmonella pullorum, Salmonella choleraesuis, Salmonella enteritidis, Klebsiella pneumoniae, Enterobacter cloacae*, and *Enterococcus faecalis*. Preferred *Escherichia coli* include but are not limited to entero-toxic, entero-hemorrhagic, entero-invasive, entero-pathogenic or other strains.

More preferred strains of *Escherichia coli* include DH5α and HB101. More preferred strains of *Salmonella typhi* include CVD 908, CVD 908-htrA, X4073 and TY800. More preferred strains of *Shigella sonnei* include 53GI and 53 GII.

Most preferred strains of bacteria to use as live attenuated vaccines include *S. typhi*, strain Ty21a, which carries a mutation in its galE gene, and *V. cholerae* carrying mutations in its ctxA gene which prevent the expression of cholera toxin.

Attenuated vaccines can be administered directly to the mammal. The vaccines obtained using the methods of the invention can be formulated as pharmaceutical compositions for administration in any suitable manner. The preferred route of administration is oral. Other routes of administration include rectal, intrathecal, buccal (e.g., sublingual) inhalation, intranasal, and transdermal (see e.g. U.S. Pat. No. 6,126,938). Although more than one route can be used to administer a particular composition, a particular route can often provide a more immediate and more effective reaction than another route.

The immunoprotective compositions to be administered are provided in a pharmaceutically acceptable solution such as an aqueous solution, often a saline or buffered solution, or they can be provided in powder form. There is a wide variety of suitable formulations of pharmaceutical compositions of the present invention. See, e.g., Lieberman, *Pharmaceutical Dosage Forms*, Marcel Dekker, Vols. 1-3 (1998); *Remington's Pharmaceutical Science,* 17th ed., Mack Publishing Company, Easton, Pa. (1985) and similar publications. The compositions may also include an adjuvant. Examples of known suitable adjuvants include alum, aluminum phosphate, aluminum hydroxide, and MF59 (4.3% w/v squalene, 0.5% w/v Tween 80, 0.5% w/v Span 85)—these are the only ones currently licensed for use in humans. For experimental animals, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion, or Bacille Calmette-Guerin (BCG). The effectiveness of an adjuvant may be determined by measuring the amount of antibodies directed against the immunogenic antigen.

The concentration of immunogenic antigens of the invention in the pharmaceutical formulations can vary widely, i.e. from less than about 0.1%, usually at or at least about 2% to as much as 20% to 50% or more by weight, and will be selected primarily by fluid volumes, viscosities, etc., in accordance with the particular mode of administration selected.

Formulations suitable for oral administration can consist of (a) liquid solutions, such as an effective amount of the recombinant bacteria suspended in diluents, such as buffered water, saline or PEG 400; (b) capsules, sachets or tablets, each containing a predetermined amount of the active ingredient, as lyophilized powder, liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art. It is recognized that the attenuated vaccines, when administered orally, must be protected from digestion. This is typically accomplished either by complexing the vaccines with a composition to render it resistant to acidic and enzymatic hydrolysis or by packaging the vaccines in an appropriately resistant carrier such as a liposome or enteric coated capsules. Means of protecting the attenuated bacteria from digestion are well known in the art. The pharmaceutical compositions can be encapsulated, e.g., in liposomes, or in a formulation that provides for slow release of the active ingredient.

The attenuated vaccines, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

The dose administered to a patient, in the context of the present invention should be sufficient to effect a beneficial therapeutic and/or prophylactic response in the patient over time. The dose will be determined by the efficacy of the particular attenuated vaccine employed and the condition of the patient, as well as the body weight or vascular surface area of the patient to be treated. The size of the dose also will be determined by the existence, nature, and extent of any adverse side-effects that accompany the administration of a particular vaccine in a particular patient.

In determining the effective amount of the vaccine to be administered in the treatment or prophylaxis of an infection or other condition, the physician evaluates vaccine toxicities, progression of the disease, and the production of anti-vaccine vector antibodies, if any.

The compositions are administered to an animal that is at risk from acquiring an infection caused by *S. sonnei* or to prevent or at least partially arrest the development of the infection and its complications. An amount adequate to accomplish this is defined as a "therapeutically effective dose." Amounts effective for therapeutic use will depend on, e.g., the antigen composition, the manner of administration, the weight and general state of health of the patient, and the judgment of the prescribing physician. Single or multiple doses of the antigen compositions may be administered depending on the dosage and frequency required and tolerated by the patient, and route of administration.

In particular embodiments, a therapeutically effective dose of the immunoprotective composition is administered to an individual. Amounts of live attenutated bacteria expressing the *S. sonnei* rfb/rfc gene cluster (SEQ ID NOs: 2-4), the O17 gene cluster, or other antigens present in the initial immunization generally range from about $5\times10^6$ to $5\times10^{11}$ organisms per patient, and more commonly from about $5\times10^8$ to $5\times10^9$ organisms per patient.

The existence of an immune response to the first dose of the immunoprotective composition may be determined by known methods (e.g. by obtaining serum from the individual before and after the initial immunization, and demonstrating a change in the individual's immune status, for example an immunoprecipitation assay, or an ELISA, or a bactericidal assay, or a Western blot, or flow cytometric assay, or the like) prior to administering a subsequent dose. The existence of an immune response to the first dose may also be assumed by waiting for a period of time after the first immunization that, based on previous experience, is a sufficient time for an immune response and/or priming to have taken place—e.g. 1, 2, 4, 6, 10 or 14 weeks. Boosting dosages of the immunoprotective composition will contain from about $5\times10^6$ to $5\times10^{11}$ organisms per patient, depending on the nature of the immunogen.

The immunoprotective compositions are typically administered to an individual that is immunologically naïve with respect to *Shigella sonnei*. In a particular embodiment, the individual is a human child about 1-4 years of age or younger, and the antigen compositions are administered preferrably at 12 months of age with booster doses given approximately one week apart. Usually, 2-4 doses may be sufficient, however additional doses may be required to achieve a high level of immunity. Additional booster doses may be given every 1-5 years, as necessary, to maintain a high level of immunity.

In general, administration to any individual should begin prior to the first sign of disease, or possibly at the first sign of possible or actual exposure to *Shigella*.

The toxicity and therapeutic efficacy of the attenuated vaccines provided by the invention are determined using standard pharmaceutical procedures in cell cultures or experimental animals. One can determine the $ED_{50}$ (the dose therapeutically effective in 50% of the population) using procedures presented herein and those otherwise known to those of skill in the art.

The attenuated vaccines of the invention can be packaged in packs, dispenser devices, and kits for administering genetic vaccines to a mammal. For example, packs or dispenser devices that contain one or more unit dosage forms are provided. Typically, instructions for administration of the compounds will be provided with the packaging, along with a suitable indication on the label that the compound is suitable for treatment of an indicated condition. For example, the label may state that the active compound within the packaging is useful for treating a particular infectious disease, enteric disorder, or for preventing or treating other diseases or conditions that are mediated by, or potentially susceptible to, a mammalian immune response.

EXAMPLES

The following example is offered to illustrate, but not to limit the claimed invention.

I. Materials and Methods

Bacterial Strains, Plasmids, and Growth Conditions.

The bacterial strains and plasmids utilized are described in Table 1. Wild type *S. sonnei* strain 53G form I (i.e. 53GI), harboring the 180 kb virulence plasmid, was used for cloning studies and as a positive control for LPS analysis and immunoblot assays. Studies of plasmid-based form I O-Ps expression were performed in *E. coli* strains HB101 or DH5α, *Salmonella* serovar *Typhi* strain Ty21a, and virulence plasmid-minus *S. sonnei* strain 53G form II (i.e. 53GII).

Cosmids pHC79 and pCVD551 (kindly provided by Timothy McDaniel, Center for Vaccine Development, University of Maryland, Baltimore, Md.) were employed to clone segments of the 180 kb plasmid of *S. sonnei* 53GI. Plasmid vectors pBR325, pGB2 and pUC18 were used for subcloning.

Bacterial strains were grown at 37° C. in Luria-Bertani broth (LB) or on LB agar (Difco). Plasmid-containing strains were selected in media containing ampicillin (Ap, 100 μg/ml), spectinomycin (Sp, 50 μg/ml), chloramphenicol (Cm, 35 μg/ml), or tetracycline (Tc, 20 μg/ml).

Plasmid Manipulations

Unless otherwise noted all DNA manipulations were performed essentially following the procedures outlined in Sambrook et al. (35). Restriction enzymes were used with the buffers supplied by the manufacturer (Roche). Electroporation of plasmid constructs was performed with a GENE PULSER® Electroporation System (Bio-Rad).

Cloning of *S. sonnei* Form I Genes.

pWR101 and pWR102 are form I antigen-expressing cosmids that contain large overlapping regions of the *S. sonnei* 180 kb plasmid from strain 53GI (D. J. Kopecko, L. S. Baron, T. L. Hale, S. B. Formal and K. Noon, Abstr. 83th Annual Meeting of the American Society for Microbiology, abstr. D 10, 1983). These recombinant cosmids, initially selected in *E. coli* recipients on antibiotic-containing media, were identified by colony immunoblotting and bacterial agglutination assays using purified form I O-antigen-specific, rabbit polyclonal antiserum (see below). The essential form I genes and flanking sequences were subcloned from the 39 kb insert of pWR101 (Table 1). First, pWR101 DNA was digested with BamH1 and a resulting 30 kb fragment was ligated to the isoschizomer BglII-digested cosmid pCVD551. DNA was packaged in lambda phage particles in vitro using a commercial kit GIGAPACK® II Plus Packaging Extract, Stratagene) according to the manufacturer's instructions. Lambda-packaged DNA was used to infect *E. coli* HB101 or DH5α, and the recombinants were screened for form I antigen expression by colony immunoblotting. A HindIII partial digest of one form I-expressing clone, designated pXG914, was ligated to the multicopy plasmids pUC18 and pBR325, and the low copy plasmid pGB-2 (7). Inserts representing one or more of three contiguous HindIII fragments of 12.4, 1.2 and 2.1 kb were initially obtained (i.e. pXK67 (comprising SEQ ID NO:1), pXK68 (comprising SEQ ID NO:1), pXK66 (comprising SEQ ID NO:2), pXK65 (comprising SEQ ID NO:2) and pXK46 (comprising SEQ ID NO:5)). Additional deletion derivatives (i.e. pXK45 (comprising SEQ ID NO:3), pXK50 (comprising SEQ ID NO:4) and pXK47 (comprising SEQ ID NO:6)) of this region were obtained to delimit the form I biosynthetic region (Table 1).

DNA Sequencing and Analysis.

DNA sequencing was performed using Ready Reactions DyeDeoxy Terminator cycle sequencing kits (Applied Biosystems) and an ABI model 373A automated sequencer. Subclones used for sequencing studies included pXK2.1 (comprising SEQ ID NO:9), pXK1.2 (comprising SEQ ID NO:10), pXK1.4 (comprising SEQ ID NO:11), pXK47 and pXG914 (Table 1). Limited sequencing of pWR102 was also performed. Sequences were assembled and analyzed using the Vector NTI suite 6.0 software (InforMax, Inc.). DNA homology searches were performed using the Basic Local Alignment Search Tool (BLAST) of the National Center for Biotechnology Information. The GenBank sequence accession number for the 17,986 bp sequence of pWR101 identified in this work is AF294823 (comprising SEQ ID NO:7) and the accession number for the 2,964 bp sequence of pWR102 is AF455358 (comprising SEQ ID NO:8).

Antisera and Slide Agglutination.

Rabbit polyclonal form I specific antiserum, kindly provided by S. Formal (Walter Reed Army Institute of Research, Washington, D.C.), was produced by repeated immunization of New Zealand white rabbits with whole cells of heat-killed *S. sonnei* 53GI. Group D-specific *Shigella* typing sera (Difco) was also utilized. These rabbit antisera were absorbed with heat-treated (70° C., 30 min) *S. sonnei* form II and *E. coli* HB101 cells. Packed cells (0.1 ml) were added to 1.0 ml of undiluted or 10-fold diluted antiserum, mixed and incubated for 2 h at 37° C. and overnight at 4° C. Following centrifugation, the absorbed antiserum was stored at 4° C. for use in bacterial agglutination assays performed on microscope slides as previously described (12). Absorbed form I-specific antiserum did not agglutinate *E. coli, S. sonnei* 53GII or *Salmonella* host strains.

LPS and Immunoblot Analyses.

*Salmonella, Shigella*, and *E. coli* strains carrying various plasmid constructs were grown overnight with aeration at 37° C. in LB media containing appropriate antibiotics. Bacteria were pelleted by centrifugation and lysed in SDS-PAGE sample buffer containing 4% 2-mercaptoethanol. The sample was boiled for 5 min, treated with proteinase K for 1 h and analyzed by SDS-PAGE using a 15% gel and the Laemmli buffer system (28). Gels were silver-stained (22) or subjected to Western blotting with form I-specific antiserum.

Western blotting was performed using PVDF membranes (Schleicher & Schuell). The membranes were blocked with 5% non-fat dry milk in Tris-buffered saline (TBS; 20 mM Tris-HCl, 150 mM NaCl, pH7.5) and reacted with anti-form I serum followed by protein A-alkaline phosphatase conjugate. The developing solution consisted of 200 mg of Fast Red TR salt and 100 mg of Naphthol NS-MX phosphate (Sigma) in 50 ml of 50 mM Tris buffer (pH 8.0).

Recombinant clones expressing the *S. sonnei* O-Ps were identified by colony immunoblotting performed with anti-form I serum and protein A-alkaline phosphatase conjugate as described above. Colonies of recipient *E. coli, S. sonnei* 53G II, or *S. Typhi* strains alone did not react with the absorbed form I-specific antisera under these conditions.

Stability of Form I O-Ps Expression in *Salmonella*.

Several *S. Typhi* Ty21a strains, each containing a different form I-expressing recombinant plasmid, were tested for stability of form I O-Ps expression. Each form I-expressing strain was diluted to approximately 100 cfu per ml and grown for 12 h (i.e. approximately 25 generations) with aeration at 37° C. in LB media under nonselective conditions (i.e. without antibiotics). These cultures were diluted again to 100 cfu per ml in LB and grown for an additional 12 h. Samples taken after 12 and 24 h of nonselective growth were plated onto LB agar without antibiotics and incubated at 37° C. At least 100 colonies of each strain were tested at each time point for O-Ps expression by the colony immunoblot assay.

Animal Immunization Study.

Outbred ICR mice weighing from 13 to 15 g were used to assess immune protection as described previously (12). Vaccine candidate strains and control Ty21a alone were grown overnight in BHI broth (Difco) supplemented with 0.01% galactose, washed, and suspended in sterile saline to a concentration of $5 \times 10^7$ cfu per ml. Mice were inoculated intraperitoneally with a single 0.5 ml dose of either vaccine or control cell suspensions or sterile saline. Immunized and control mice were challenged 5 weeks postimmunization with $5 \times 10^5$ cfu (approximately $100 \times LD_{50}$) of freshly grown, mid-log phase *S. sonnei* strain 53GI in 0.5 ml of 5% hog gastric mucin (Sigma) in sterile saline. Survival was monitored for 96 h.

II. Results

Cloning and Genetic Downsizing for Expression of the Form I O-Antigen Locus.

To delimit the DNA region required for biosynthesis of form I antigen, we initially cloned this region from *S. sonnei* strain 53GI in cosmids (see Methods). The 30 kb BamH1 insert of pXG914, which directs the expression of typical form I LPS in *E. coli*, was partially digested with HindIII and separately ligated to low and high copy plasmid vectors pGB-2, pBR325, and pUC18. The resulting form I-expressing subclones (Table 1), containing inserts comprised of one or more of three adjacent HindIII fragments of 12.4, 1.2, and 2.1 kb (e.g. pXK67, pXK65, and pXK46 and several additional deletion derivatives (i.e. pXK45, pXK47, and pXK50) were characterized for form I expression in three host backgrounds (i.e. *E. coli, S. Typhi,* and *S. sonnei*) (FIG. 1). Plasmid inserts ranging in size from 15.7 to 12.4 kb all directed form I antigen expression in each host as shown by results of bacterial agglutination of plasmid bearing subclones with form I-specific antiserum (FIG. 1B). However, this antiserum did not agglutinate bacteria containing pXK47, which contains an 11 kb insert, like the one previously reported (24) to contain the entire form I biosynthetic region. In the present study, the smallest inserts that directed form I antigen expression were the 12.7 and 12.4 kb inserts of plasmids pXK50 and pXK46, respectively. However, form I specific agglutination of host strains containing pXK46 was weak and did not correlate with the detection of typical polymerized O-antigen as described below.

O-units as detected by silver stain or immunoblotting (FIG. 2A). Immunoblotting also detected additional material of lower mobility, well above the position of 25 O-repeats, suggesting capsule-like expression. As expected, anti-form I reactive material was not detected with *S. sonnei* 53GII or the "rough" *E. coli* HB101. However, recipient 53GII or HB101 carrying either pXK67 or pXK65 showed typical LPS ladder patterns like that seen from parent strain 53GI. Similar LPS ladder patterns were detected in further studies of *E. coli* carrying cosmid pWR01, pXG914, pXK45 containing a 13.3 kb insert (FIG. 2B) or pXK50 containing a 12.7 kb insert (data not shown). In contrast, a dramatic loss of form I immunoreactive material was noted in either *Shigella* (FIG. 2A) or *E. coli* (FIG. 2B) containing pXK46, which has a 12.4 kb insert. Moreover, host strains carrying pXK47, which has an 11 kb insert, showed no reaction by silver staining or immunoblotting (data not shown).

*S. Typhi* Ty21a exhibited a typical and distinctive 9,12 LPS ladder pattern by silver-stain analysis, but, as expected, showed no form I antigen by immunoblotting (FIG. 2C). The presence of pXK67, pXK65, or pXK45 (FIG. 2C) or the

TABLE 1

Bacterial strains and plasmids

| Strain/Plasmid | Genotype/Description | Reference |
|---|---|---|
| Strain | | |
| *E. coli* | | |
| DH5α | supE44, hsdR17, recA1, endA1, gyrA96, thi-1, relA1 | (35) |
| HB101 | supE44, hsdS20 ($r_B^-m_B^-$), recA13, ara-14, proA2, lacY1, galk2, rpsL20, xyl-5, mtl-1 | (35) |
| *S. Typhi* | | |
| Ty21a | galE, ilvD, viaB ($Vi^-$), $H_2S^-$ | (14) |
| *S. sonnei* | | |
| 53GI | form I (phase I), virulent isolate | (26) |
| 53GII | form II (phase II), avirulent variant | (26) |
| Plasmid | | |
| pGB-2 | pSC101 derivative, low copy plasmid; $Sm^r$, $Spc^r$ | (7) |
| pBR325 | pBR322-derived plasmid; $Cm^r$, $Ap^r$, $Tc^r$ | (4) |
| pUC18 | pBR322-derived cloning vector; $Lac^+$, $Ap^r$ | (41) |
| pHC79 | pBR322-derived cosmid; $Ap^r$, $Tc^r$ | (23) |
| pCVD551 | pHC79-derived cosmid; $Cm^r$ | Timothy McDaniel |
| pWR101 | *S. sonnei* form I positive cosmid clone #19; $Tc^r$ | (26) |
| pWR102 | *S. sonnei* form I positive cosmid clone #27; $Tc^r$ | (26) |
| pXG914 | 30 kb BamHI fragment of pWR101 cloned into pCVD551 cosmid; $Cm^r$ | This study |
| pXK68 | 15.7 kb HindIII fragment of pXG914 cloned into pBR325; $Ap^r$, $Cm^r$ | This study |
| pXK67 | 15.7 kb HindIII fragment of pXG914 cloned into pGB-2; $Sm^r$, $Spc^r$ | This study |
| pXK66 | 13.6 kb HindIII fragment from pXG914 cloned into pBR325; $Ap^r$, $Cm^r$ | This study |
| pXK65 | 13.6 kb HindIII fragment of pXK67 cloned into pGB-2; $Sm^r$, $Spc^r$ | This study |
| pXK45 | 13.3 kb HindIII-SmaI fragment of pXK45 cloned into pGB-2; $Sm^r$, $Spc^r$ | This study |
| pXK50 | 12.7 kb HindIII-PmeI fragment of pXK45 cloned into pGB-2; $Sm^r$, $Spc^r$ | This study |
| pXK46 | 12.4 kb HindIII fragment of pXK67 cloned into pUC18, $Ap^r$ | This study |
| pXK47 | 11.0 kb XbaI-HindIII fragment of pXK46 cloned into pUC18; $Ap^r$ | This study |
| pXK2.1 | 2.1 kb HindIII fragment of pXK67 cloned into pUC18; $Ap^r$ | This study |
| pXK1.2 | 1.2 kb HindIII fragment of pXK67 cloned into pUC18; $Ap^r$ | This study |
| pXK1.4 | 1.4 kb XbaI-HindIII fragment of pXK46 cloned into pUC18; $Ap^r$ | This study |

Plasmid-based expression of form I O-Ps in each host was further examined by SDS-PAGE followed by silver-staining and Western blotting with form I-specific antisera (FIG. 2). LPS from wildtype *S. sonnei* 53GI gave a typical O-antigen ladder pattern with the predominant chain length of 20 to 25 smaller pXK50 (data not shown) in Ty21a did not noticeably affect the silver-stained O-antigen pattern of this strain. However, immunoblot analysis revealed that these plasmids directed the expression of anti-form I reactive material. The form I material in *S. Typhi* did not migrate as LPS and presumably was attached to carrier lipid as proposed previously (37). No immunoreactive form I O-Ps was detected in strain Ty21a carrying pXK46. Thus, the combined results suggest that plasmids pXK67, pXK65, pXK45, and pXK50, but not pXK46, contain the essential genes for synthesizing form I O-Ps in each of the three host strains examined.

Sequence Analysis of the Form I Gene Region.

A contiguous segment of about 18 kb was sequenced to characterize the form I biosynthetic gene region and evolutionarily important adjacent regions, (see FIG. 1C; Genbank #AF294823). Primary analysis of this sequence revealed 18 ORFs, the properties of which are summarized in Table 2 and FIG. 1. The notably higher GC content for ORF8, ORFs 11 through 13 and other terminal sequences, compared with the remainder of the form I region, suggests different evolutionary origins for these sequences.

The inserts of all plasmids that direct the expression of typical form I antigen (FIG. 1B) begin at the HindIII site charide biosynthesis (Table 2), except ORF9, which we suggest, encodes a C5-epimerase based on the need for such an enzyme in our proposed biosynthetic pathway (see Discussion). The presence of a putative promoter, identified by a -35 and -10 consensus sequence (ATTACCN$_{15}$TATAGT) (SEQ ID NO:19) at nucleotide positions 1,645 to 1,671 of our sequence (i.e. AF294823, SEQ ID NO:7) and a typical transcriptional terminator, identified by a stem-loop structure and adjacent poly(T) sequence at nucleotide positions 13,930 to 13,949 of SEQ ID NO:7 (and is SEQ ID NO:13) defines an essential 12.3 kb region required for form I O-Ps biosynthesis by our plasmid subclones. This region, which contains 10 intact ORFs, including the transposase of IS630, begins near the 3' end of ORF3 and ends between ORF13 and ORF14 (FIG. 1C).

Sequencing of the operon-adjacent regions revealed several interesting features that aid in understanding the evolution of the plasmid-borne form I region.

TABLE 2

Summary of S. sonnei 53G ORFs

| ORF | Gene Name | Location in Sequence | (G + C) % | aa no. | Selected Homolog (accession no.) | Identity % (aa[a]) | Proposed function of 53G protein |
|---|---|---|---|---|---|---|---|
| 1 | insB | 519-16 | 54.4 | 167 | IS1 (InsB), E. coli (AJ223474) | 98 (167) | IS1 transposase |
| 2 | insA | 713-438 | 52.5 | 91 | IS1 (InsA), E. coli (AJ223475) | 100 (91) | IS1 protein |
| 3 | wzz | 788-1,720 | 36.4 | 310 | Wzz, Actinobacillus actinomycetemcomitans (AB041266) | 35 (328) | chain length determinant |
|  |  |  |  |  | Wzz, E. coli (AF011911) | 26 (292) |  |
| 4 | wbgT | 1,756-3,069 | 36.1 | 437 | WbpO, Pseudomonas aeruginosa (AF035937) | 74 (418) | UDP-GalNAc dehydrogenase |
|  |  |  |  |  | WcdA, Salmonella typhi (D14156) | 63 (418) |  |
| 5 | wbgU | 3,150-4,187 | 34.1 | 345 | WbpP, Pseudomonas aeruginosa (AF035937) | 67 (343) | UDP-GlcNAc C4-epimerase |
|  |  |  |  |  | WcdB, Salmonella typhi (D14156) | 65 (338) |  |
| 6 | wzx | 4,276-5,556 | 28.1 | 426 | Cps19CJ, Streptococcus pneumoniae (AF105116) | 21 (394) | repeat unit transporter |
|  |  |  |  |  | Wzx, Escherichia coli (AF104912) | 19 (393) |  |
| 7 | wzy | 5,625-6,797 | 29.8 | 390 | Cap14H, Streptococcus pneumoniae (X85787) | 25 (201) | polysaccharide polymerase |
| 8 | IS630 | 6,894-7,925 | 52.8 | 343 | IS630 (ORF343), S. sonnei (P16943) | 99 (343) | IS630 transposase |
| 9 | wbgV | 7,958-9,202 | 29.9 | 414 | None | none | UDP-GalNAcA C5-epimerase[b] |
| 10 | wbgW | 9,186-10,181 | 26.6 | 331 | WaaV, E. coli (AF019746) | 27 (237) | glycosyl transfease |
|  |  |  |  |  | LgtA, Neisseria gonorrhoeae (U14554) | 30 (142) |  |
| 11 | wbgX | 10,178-11,332 | 37.6 | 384 | WlbF, Bordetella bronchiseptica (AJ007747) | 55 (392) | amino-sugar synthetase |
|  |  |  |  |  | Per, E. coli (AF061251) | 34 (383) |  |
|  |  |  |  |  | RfbE, Vibrio cholerae (X59554) | 31 (380) |  |
| 12 | wbgY | 11,349-11,939 | 35.4 | 196 | WlbG, Bordetella pertussis (X90711) | 53 (194) | glycosyl transferase |
|  |  |  |  |  | WcaJ, E. coli K-12 (U38473) | 34 (197) |  |
|  |  |  |  |  | WbaP, E. coli K30 (AF104912) | 31 (212) |  |
| 13 | wbgZ | 11,954-13,873 | 44.3 | 639 | WbcP, Yersinia enterocolitica (Z47767) | 68 (633) | UDP-GlcNAc C6-dehydratase C4-reductase |
|  |  |  |  |  | WbpM, Pseudomonas aeruginosa (U50396) | 49 (657) |  |
|  |  |  |  |  | WlbL, Bordetella pertussis (X90711) | 49 (592) |  |
|  |  |  |  |  | FlaA1, Helicobacter pylori (AE000595) | 28 (297) |  |
| 14 | aqpZ | 13,992-14,504 | 55.5 | 170 | ORF10P, P. shigelloides (AB025970) | 99 (146) | water channel protein |
|  |  |  |  |  | AqpZ, E. coli (AE000189) | 71 (146) |  |
| 15 | orfA | 14,657-14,983 | 53.8 | 108 | IS629 (ORFA), S. sonnei (P16941) | 99 (108) | IS629 transposase |
| 16 | InsB | 16,706-15,486 | 55.0 | 406 | IS91 (TnpA), E. coli (X17114) | 94 (406) | IS91 transposase |
| 17 | InsA | 17,071-16,706 | 53.0 | 121 | IS91 (ORF121), E. coli (S23781) | 95 (121) | IS91 protein |
| 18 | InsB | 17,130-17,978 | 54.8 | 282 | IS911 (InsB), S. dysenteriae (AAF28127) | 99 (271) | IS911 transposase |

[a]Length of comparable sequence in the homologous protein.
[b]Proposed function based on the predicted presence of an enzyme that converts UDP-GalNAcA to UDP-AltNAcA (see Discussion)

located at nucleotide position 1,310 of our sequence, in the middle of ORF3, a homolog of wzz. Ten identically oriented ORFs (i.e. ORFs 4 to 13) occur within the 12.7 kb insert of pXK50, the smallest insert that directs typical form I antigen expression. One of these ORFs (i.e. ORF 8 in FIG. 1C) represents the transposase of IS630, which is inserted nonpolarly into the C-terminus of the preceding biosynthetic ORF as noted previously (38). All remaining ORFs present within the pXK50 insert are homologs of known genes for polysac- Analysis of upstream sequences from pWR101 subclones revealed the presence of a partial wzz (933 bp) created by an IS1 insertion. Sequence homology to the plasmid R100 was noted immediately 5' of this IS1 element (Xu et al., unpublished data; FIG. 3A). Unexpectedly, the 5' region of pWR101 differed from that in pWR102. The latter plasmid contained a partial IS91 (201 bp), a partial IS630 (339 bp), a JUMPstart sequence (i.e. CAGCGCTTTGGGAGCTGAAACT-CAAGGGCGGTAGCGTA) (SEQ ID NO:14), which is characteristic of O-antigen loci and a full-length copy of wzz (1,104 bp) (FIG. 3A). The observation of a full length *S. sonnei* plasmid-borne wzz, as reported previously (38), preceded by a JUMPstart sequence and partial IS elements suggests that this pWR102-derived sequence represents that of the original 180 kb *S. sonnei* virulence plasmid and that during subcloning of this region in pWR101, an IS1 element insertion occurred within wzz causing a 5'-deletion of this gene and adjacent upstream sequences (FIG. 1C). The remnants of IS630 and IS91 found upstream of JUMPstart in pWR102 suggests the insertion of IS91 via its left inverted repeat (IRL) into a -GTTC-target site (33) originally present within IS630 and subsequent deletion of much of the IS91 element (FIG. 3A).

Immediately downstream of the form I encoding region, a partial aqpZ gene (513 bp) was found that is virtually identical to the 5'-portion of *Pleisiomonas shigelloides* aqpZ (699 bp) (6). Further downstream a partial IS629 element (31), a small fragment of a *Pseudomonas* IS element, a full-length IS91 and partial IS911 sequences were identified (FIG. 3B). The specific target sequence of IS91, -GTTC-, was found immediately adjacent to the right inverted repeat (IRR) of this element, indicating the prior insertion of IS91 into a target site originally present in the middle of IS911. Thus, the region downstream of the form I biosynthetic operon contains numerous IS element remnants, and like the upstream region, serves as a recombinational hotspot.

Stability of Form I O-Ps Expression in a *Salmonella* Vaccine Vector.

Several recombinant plasmids were tested for their ability to direct stable form I O-Ps expression in *S. Typhi* Ty21a. Following electroporation of each plasmid into strain Ty21a, the resulting strain was grown in the absence of antibiotic selective pressure for approximately 25 and 50 generations and then examined for form I antigen expression. The percentage of form I-positive colonies was determined by immunoblot assay of colonies grown on LB agar without antibiotic. *Salmonella* harboring the 15.7 kb form I region insert in the multicopy vector pBR325 (i.e. pXK68) exhibited highly unstable form I O-Ps expression. Thus, following growth for 24 hrs, the loss of antigen expression from *Salmonella* carrying this plasmid was greater than 97% (Table 3). Deletion of IS91 from the 15.7 kb insert of pXK68 to generate the 13.6 kb fragment of pXK66 increased the stability of form I O-Ps expression. The percentage of form I positive colonies was further enhanced when these inserts were carried in the low copy vector, pGB2. The 15.7 kb insert in pGB-2 (i.e. pXK67) exhibited markedly improved stability of antigen expression compared with the same insert in pBR325. Again, deletion of IS91 from the 15.7 kb insert of pXK67 to generate the 13.6 kb fragment of pXK65 increased the stability of form I O-Ps expression. In fact, as shown in Table 3, pXK65 and pXK45 directed stable form I antigen expression in *Salmonella* over 50 generations.

TABLE 3

Stability of plasmid-based form I O-Ps expression in *S. Typhi* Ty21a[a]

| Plasmid | Vector | Insert (kb) | Percent form I O-Ps positive colonies at: | |
|---|---|---|---|---|
| | | | 12 h | 24 h |
| pXK68 | pBR325 | 15.7 | 12.5 | 2.5 |
| pXK66 | pBR325 | 13.6 | 80 | 45.5 |

TABLE 3-continued

Stability of plasmid-based form I O-Ps expression in *S. Typhi* Ty21a[a]

| Plasmid | Vector | Insert (kb) | Percent form I O-Ps positive colonies at: | |
|---|---|---|---|---|
| | | | 12 h | 24 h |
| pXK67 | pGB-2 | 15.7 | 78 | 69 |
| pXK65 | pGB-2 | 13.6 | 100 | 98.5 |
| pXK45 | pGB-2 | 13.3 | 100 | 97 |

[a]A form I positive colony of each strain was inoculated in L-broth and grown for 12 h (approximately 25 generations) before dilution and regrowth in fresh L-broth for an additional 12 h. Samples taken at 12 or 24 h were plated on L-agar and the resulting colonies assayed for form I O-Ps by colony immunoblotting.

Vaccine Protection Study in Mice.

Shigellae are specific for higher primates and nonprimate models do not exist for the development of either typical dysenteric disease from low infectious doses of these bacteria or protective immunity from natural challenge. Nevertheless, mice have been employed previously to demonstrate immune stimulation by a vaccine and specific protection against parenteral challenge with virulent *S. sonnei* (12). In the present study, ICR mice were immunized with a single ip dose of viable *S. Typhi* Ty21a containing pXK65 or pXK45, Ty21a alone, or saline and challenged at 5 weeks post-immunization with $5 \times 10^5$ virulent *S. sonnei* 53GI (i.e. approximately $100 \times LD_{50}$). This challenge resulted in 100% mortality in negative control mice immunized with saline or strain Ty21a alone (Table 4). In contrast, all mice that received Ty21a harboring the stable form I inserts deleted for IS91 and carried by pGB-2 were protected from the *S. sonnei* challenge.

TABLE 4

Mouse protection against virulent *S. sonnei* challenge

| Vaccine (plasmid)/control[a] | Survivors/total[b] |
|---|---|
| *S. Typhi* Ty21a (pXK45) | 8/8 |
| *S. Typhi* Ty21a (pXK65) | 8/8 |
| *S. Typhi* Ty21a | 0/8 |
| Saline | 0/8 |

[a]Vaccine strains containing plasmids or control Ty21a alone were suspended in saline to a concentration of $2.5 \times 10^7$ cells per 0.5 ml dose for intraperitoneal immunization. Saline (0.5 ml) served as control.
[b]Each mouse was challenged intraperitoneally with $5 \times 10^5$ CFU *S. sonnei* 53GI (i.e. $100 \times LD_{50}$) in 0.5 ml saline containing 5% hog gastric mucin and monitored for four days.

III. Discussion

Figure 4:
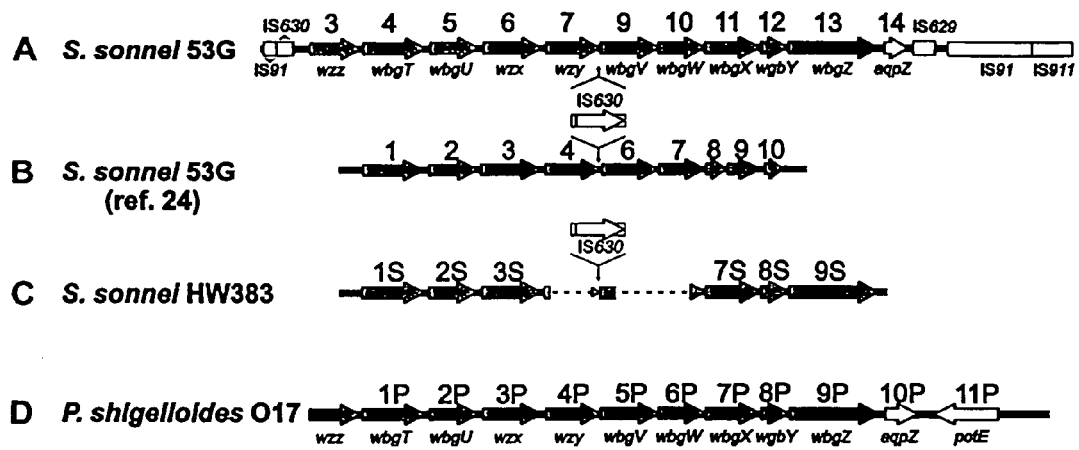
FIG. 4. Comparison of gene clusters for biosynthesis of the *S. sonnei* form I O-Ps and the substantially identical *P. shigelloides* O17 Ps: (A) Composite *S. sonnei* 53G form I gene cluster and flanking regions derived from Genbank accession numbers AF285971 (SEQ ID NO:16), AF294823 (SEQ ID NO:7) and AF455358 (SEQ ID NO:8). ORFs are identified numerically as defined in Table 2 and also by gene designations (38). (B) *S. sonnei* 53G form I gene cluster reported by Houng and Venkatesan (24). (C) partial *S. sonnei* HW383 form I gene cluster determined by Chida et al. (6). (D) Composite *P. shigelloides* O17 Ps gene cluster derived from Genbank accession numbers AF285970 (SEQ ID NO:17) and AB025970 (SEQ ID NO:18). ORFs are identified numerically and by gene names (38). The ORFs for form I O-Ps biosynthesis by plasmid-bearing subclones are shaded.

The genes controlling form I O-Ps biosynthesis have previously been cloned and sequenced to varying extents as summarized in FIG. 4 (D. J. Kopecko, L. S. Baron, T. L. Hale, S. B. Formal and K. Noon, Abstr. 83th Annual Meeting of the American Society for Microbiology, abstr. D 10, 1983) (6, 24, 38, 42, 45). However, reported sequence differences in the *S. sonnei* form I gene region (FIG. 4A and B), combined with limited analyses of LPS expression, have resulted in confusion regarding the essential genes for form I antigen biosynthesis. Houng and Venkatesan (24) reported that these genes were contained within an 11 kb region of the *S. sonnei* 53GI virulence plasmid; DNA sequencing revealed ten ORFs including IS630 (FIG. 4B). However, our findings, which support other recent sequencing studies of the form I gene region in *S. sonnei* strains 53GI and HW383 (FIGS. 4A and C), as well as the corresponding gene region of *P. shigelloides* (FIG. 4D), suggest that the form I biosynthetic region contains an additional gene, designated wbgZ (FIG. 4A), homologs of which occur in many Ps gene clusters (5) but not in the sequence of Houng and Venkatesan (24) (FIG. 4B).

Figure 2:
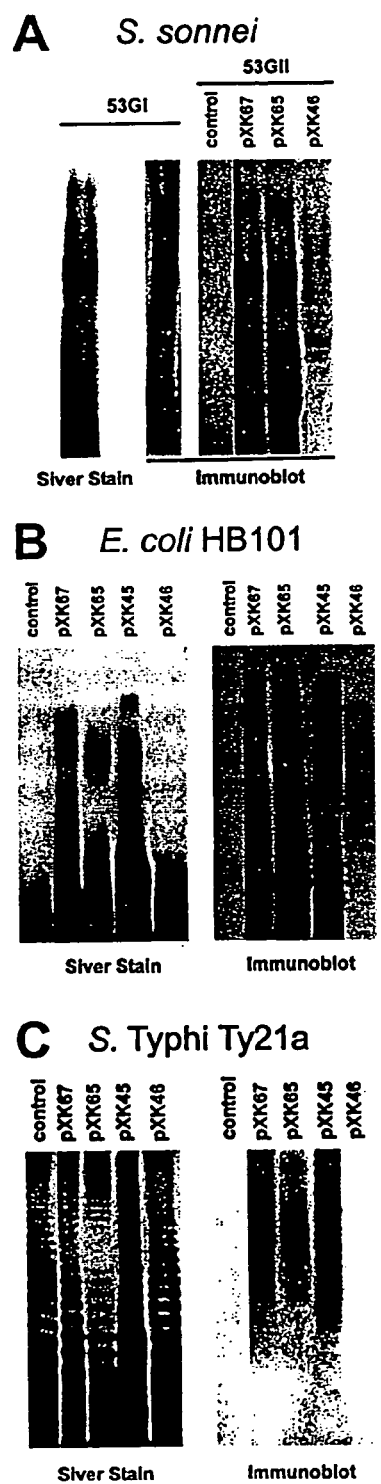
FIG. 2. Detection of SDS-PAGE separated O-Ps by silver staining and anti-form I Western immunoblotting with form I specific antiserum. O-Ps from: (A) *S. sonnei* 53GI, strain 53GII alone (control) or carrying plasmids with different form I-encoding inserts; (B) *E. coli* HB101 alone (control) or carrying different form I-encoding plasmids; (C) *S. typhi* Ty21a alone (control) or carrying different form I-encoding plasmids.

Antibody to form I O-Ps was previously reported to agglutinate subclones expressing an 11 kb form I insert (24), which lacks wbgZ. In contrast, we found that such subclones (i.e. pXK47) were not agglutinated by specific anti-form I antibody, prepared by absorption with form II *S. sonnei* cells. Further, LPS analysis by silver stain or immunoblot showed no detectable form I material from subclones expressing the 11 kb insert, but typical form I LPS from pXK50 subclones expressing the 12.7 kb insert thereby indicating that wbgZ (but not aqpZ) is required for form I O-Ps biosynthesis. The right-hand end of the form I gene region, between wbgZ and aqpZ, is further defined by the presence of a transcriptional terminator in this region and the dramatic effect on form I O-Ps synthesis seen from the short truncation of wbgZ in subclones expressing the 12.4 kb insert (FIG. 2, pXK46).

The left-hand end of the essential form I region is defined by plasmid inserts that begin in the middle of wzz (FIG. 1B) but direct the synthesis of typical form I LPS. The wild type distribution of LPS chain length seen in our *S. sonnei* subclones (FIG. 2A) can be explained by the expression of the previously described chromosomal wzz (38), which apparently determines the chain length of form I LPS. Whereas JUMPstart, a presumed transcriptional antiterminator (43), and plasmid borne wzz may play a role in biosynthesis of LPS by wild type *S. sonnei* and *P. shigelloides* 017, our studies indicate that neither of these loci is essential for form I O-Ps expression from our subclones. Such observations also suggest the presence of a promoter at the 3' end of plasmid borne wzz (6), immediately ahead of wbgT, the first essential gene for plasmid-based form I O-Ps biosynthesis. The IS630 element inserted in the C-terminus of ORF7 (nucleotides 6894-7925 of SEQ ID NO:7 which is SEQ ID NO:15) (i.e. wzy) (38) is evidently also not essential for form I O-Ps biosynthesis as the comparable region of *P. shigelloides*, which lacks IS630, also directs the production of typical LPS. Thus, the available data from studies of LPS biosynthesis clearly indicate that nine genes beginning with wbgT (ORF4) and ending with wbgZ (ORF13) (FIG. 4A) are required for form I antigen biosynthesis in each of the three host genera examined.

Figure 5:
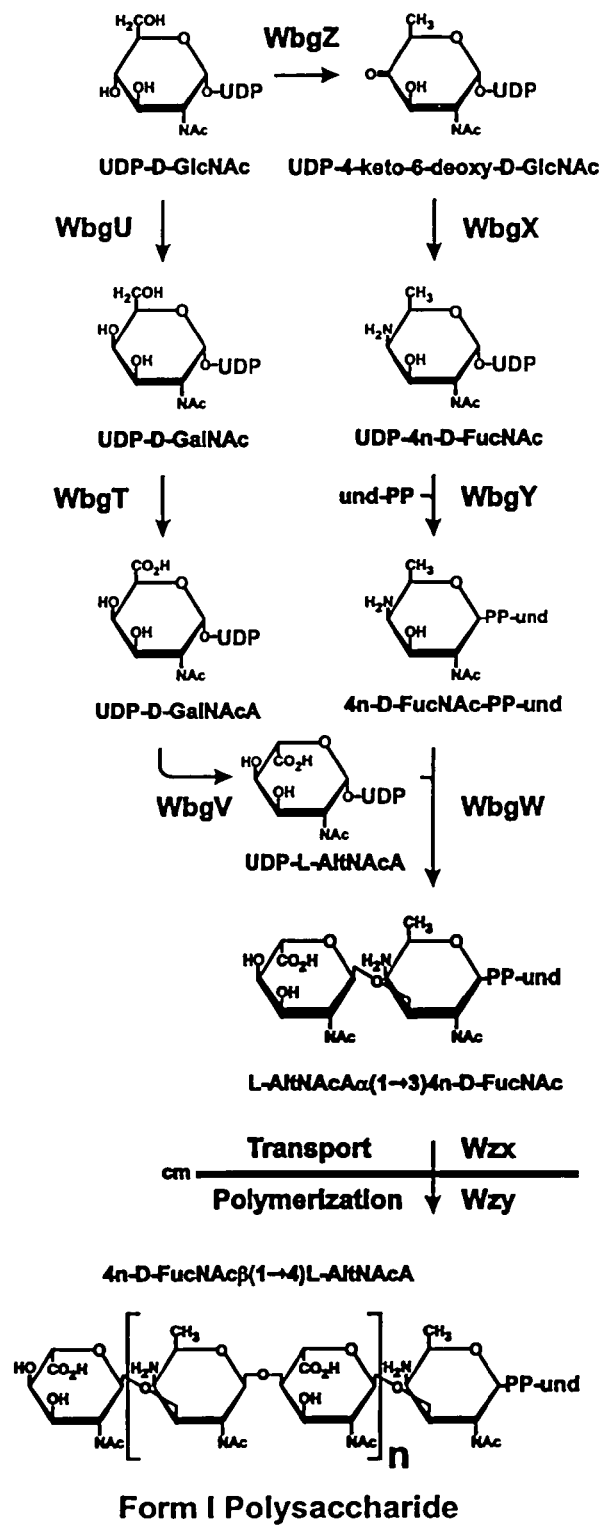
FIG. 5. Proposed pathway for biosynthesis of undecaprenyl phosphate (und-P)-linked, *S. sonnei* form I O-Ps. The pathway is based on the predicted enzymatic activities of *S. sonnei* 53G proteins as summarized in Table 2 and the structural steps required for conversion of UDP-GlcNAc to the putative form I O-Ps precursors, UDP-L-AltNAcA and UDP-4n-D-FucNAc.

The properties of these nine essential genes (Table 2) provide the basis for the detailed biosynthetic pathway presented as a working hypothesis in FIG. 5. These genes include two (i.e. wbgW and wbgY) for putative glycosyl transferases and two (ie. wzx and wzy) for proteins that function in the transport and polymerization of form I repeating units. Thus, the remaining five genes of the form I cluster may function to convert available nucleotide-linked sugars to the 4n-D-FucNAc- and L-AltNAcA-containing precursors of the form I disaccharide repeating unit (25). The initial step in formation of UDP-4n-D-FucNAc was previously proposed to involve conversion of UDP-GlcNAc to UDP-4-keto-6-deoxy-GlcNAc by the action of wbgV (38). Rather than wbgV, we suspect that wbgZ catalyzes this reaction. Homologs of wbgZ, which include FlaA1 of *Helicobacter pylori* and WbpM of *Pseudomonas aeruginosa*, are associated with synthesis of the 2,6-deoxysugars QuiNAc, D-FucNAc, and structurally related derivatives such as 4-n-D-QuiNAc (5), the C4-epimer of 4-n-D-FucNAc. Significantly, FlaA1 of *H. pylori* has recently been identified as a bifunctional UDP-GlcNAc C6-dehydratase/C4-reductase that catalyzes the conversion of UDP-GlcNAc to UDP-QuiNAc through the stable intermediate, UDP-4-keto-6-deoxy-GlcNAc (8). Consequently, the predicted intermediate product of wbgZ, UDP-4-keto-6-deoxy-GlcNAc, is the putative substrate of wbgX (38), which likely catalyzes the formation of 4-n-D-FucNAc (FIG. 5) in a manner similar to the conversion of GDP-4-keto-6-deoxymannose to GDP-perosamine by perosamine synthase of *V. cholerae* 01 (39) and *E. coli* (2).

Homologs of two other *S. sonnei* biosynthetic genes, wbgT and wbgU, occur in a number of bacteria that synthesize N-acetylgalactosamine uronic acid (GalNAcA) including *P. aeruginosa* serotype 06 (1) and Vi-capsule-expressing *Salmonella* serovars (19) (Table 2). The relevant biosynthetic pathway, proposed from studies of *P. aeruginosa* (1), involves the conversion of UDP-GlcNAc to UDP-GalNAc by WbpO and subsequent conversion of UDP-GalNAc to UDP-N-GalNAcA by WbpP. Indeed, recent biochemical studies confirm the identification of WbpP as a UDP-GlcNAc C4-epimerase (8) and WbpO as a UDP-GalNAc dehydrogenase (46). Significantly, D-GalNAcA, the predicted product of WbgT, is the C5-epimer of L-AltNAcA, a constituent of form I O-Ps. Thus, the corresponding precursor, UDP-L-AltNAcA, would be obtained by the action of a C5-epimerase on UDP-GalNAcA. We predict that this activity is provided by WbgV (FIG. 5), the only *S. sonnei* ORF that failed to retrieve significant homologs from the database (Table 2). Although weak homology between WbgV and plant NADH dehydrogenases was previously reported (38), we found that WbgV is not affiliated with these or other NADH-containing enzymes in the Blocks Data Base (Fred Hutchinson Cancer Research Center) thereby questioning the identification of WbgV as a dehydrogenase. Intracellular C5-epimerases that act on nucleotide-linked sugars have not been described to our knowledge, which may contribute to the apparent absence of WbgV homologs in the database. Extracellular C5-epimerases that act on polysaccharides are, however, well documented and include the enzymes of *P. aeruginosa* (13) and *Azotobacter vinelandii* (11) that convert D-mannuronic acid to L-guluronic acid in alginate polymers as well as mammalian enzymes that convert D-glucuronic acid to L-iduronic acid in heparin and heparin sulfate (30).

That the form I O-Ps is linked to the phase II core of *S. sonnei* (25) through 4-n-D-FucNAc suggests that 4-n-D-FucNAc is the first sugar attached to the acyl carrier lipid. This step almost certainly depends on WbgY, which is a homologue of several well-studied glycosyl transferases that link the first sugar of different O-antigen repeating units to carrier lipid (Table 2). WbgW, the other predicted glycosyl transferase (Table 2) presumably completes the biosynthetic unit by transferring L-AltNAcA thereby forming L-AltNAcAα (1→3)4-n-D-FucNAc-PP-und. Indeed, the predicted α(1→3) transfer of L-AltNAcAα by WbgW would resemble the known β(1→3) transfer of D-sugars by WaaV (20) of *E. coli* and LgtA of *N. gonorrhoeae* (16) (Table 2). Wzx, a member of the PST(2) subfamily of polysaccharide transport proteins (34), based on its predicted size (Table 2) and hydropathy profile (results not shown), would then be expected to flip the lipid-linked repeating unit from the cytoplasmic to periplasmic face of the plasma membrane without the aid of auxiliary export proteins. Wzx-mediated transport would provide the substrate for Wzy-dependent polymerization resulting in the formation of a β1-4 linkage between each adjacent repeating unit, thereby completing the form I O-Ps structure (FIG. 5).

Plasmid-based expression of form I O-Ps in *S. typhi* Ty21a, which has a core that is chemically dissimilar to that of Shigellae, resulted in the production of a lipid-linked surface Ps (37) rather than typical form I LPS (FIG. 2C). In contrast, a significant fraction of form I O-Ps synthesized in *S. sonnei* and *E. coli* was ligated to core-Lipid A. However, even from these species, a slow migrating band of form I immunoreactive material, apparently unlinked to core-Lipid A, was detected (FIGS. 2A and B). It is unclear whether this band of core-nonlinked form I material is surface bound through the acyl carrier lipid, or alternatively through another molecule as an O-antigen capsule. As pointed out in a recent review (44), O-Ps capsules are easily overlooked because serological and structural studies have generally been interpreted with the expectation that all surface 0 antigen is core-lipid A linked. However, examples such as *E. coli* serotype O111 have long been recognized (15) in which the same O-Ps is surface expressed in a LPS form and in an LPS-unlinked capsular form. Clearly, further studies of *S. sonnei* form I O-Ps are needed to clarify this possibility.

Figure 3:
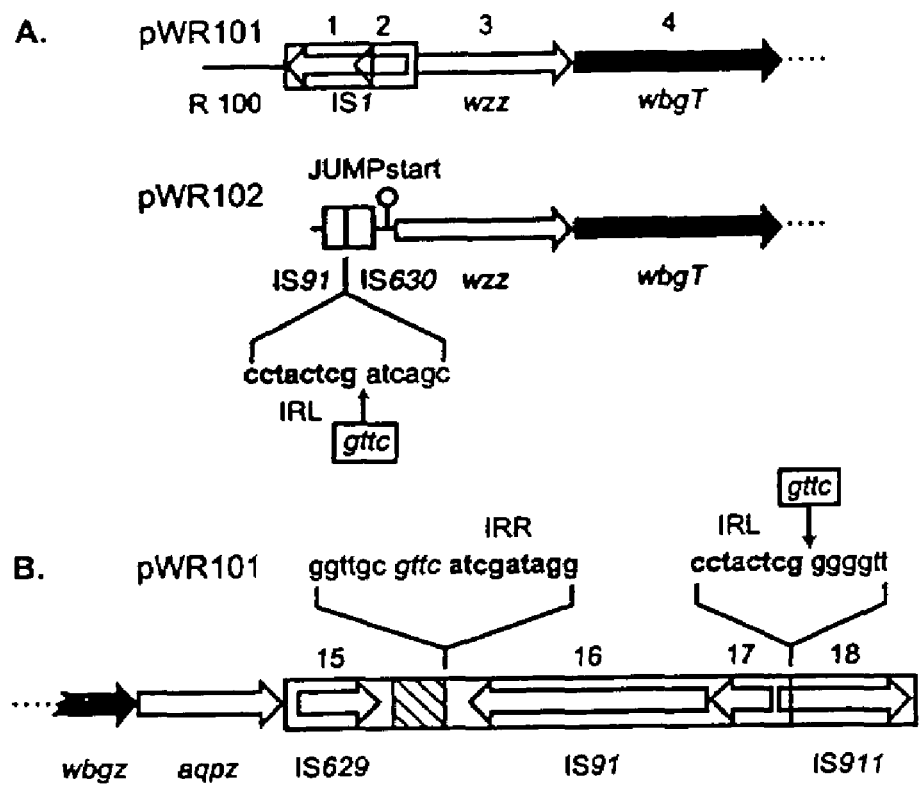
FIG. 3. ORF diagrams of the regions flanking the *S. sonnei* form I biosynthetic gene cluster. (A) Regions of pWR101 and pWR102 (including SEQ ID NO:20) upstream of wbgT. (B) Region of pWR101 downstream of wbgZ (including SEQ ID NOS:21 and 22). The sequences of the left and right inverted repeats (IRL and IRR) of IS91 are shown in bold type. The -gttc- target sequence of IS91 is italicized. The original -gttc- sites within IS630 and IS911 for insertion of IS91 are boxed. A sequence homologous to a *Pseudomonas* IS element occurs within the hatched region.

High homology between the gene regions for O-Ps biosynthesis in *S. sonnei* and *P. shigelloides* (6, 38), over the region from wzz to aqpZ (FIG. 4), supports the proposal of Reeves and coworkers (29) that *S. sonnei* evolved from *E. coli* by the acquisition of the form I biosynthetic region from *P. shigelloides*. The form I operon adjacent sequences obtained herein (FIGS. 1B and 3) provide an improved definition of the limits of the gene transfer event. Comparison of the available *S. sonnei* form I gene region sequences (FIG. 4A) with the analogous *Pleisiomonas* region (FIG. 4D) suggests the transfer of approximately 12.6 kb of *P. shigelloides* chromosomal DNA. The right-hand endpoint apparently occurred at bp 513 within aqpZ where sequence homology between *P. shigelloides* and *S. sonnei* ends abruptly. The left-hand junction apparently occurred upstream of JUMPstart where partial IS elements were identified in pWR102 (FIG. 3). Since remnants of IS91, IS630, and other elements have been shown to flank the form I operon in *S. sonnei* (FIGS. 3 and 4A), any of these elements could have been involved in transposition of this region, likely from the *Pleisiomonas* chromosome to a plasmid, which was then transferred to the evolving *E. coli* recipient.

Form I antigen expression is frequently lost in *S. sonnei* mainly by spontaneous loss of the large virulence plasmid (26). Instead of stabilizing form I expression in attenuated *Shigella* for use as a live vaccine, our approach has been to transfer the form I genes into *S. Typhi* Ty21a. Ty21a (14) is a proven safe and effective, mucosally-delivered, live bacterial vaccine which stimulates long-term protection against typhoid fever. In addition, Ty21a has the advantage of oral administration, eliminating the need for needles, syringes and a skilled health professional for immunization. A live, oral candidate vaccine strain, 5076-1C, was previously constructed by introducing the large *S. sonnei* virulence plasmid into Ty21a. The resulting strain was protective in humans challenged with virulent *S. sonnei* (3, 12, 21) but was genetically unstable, resulting in loss of form I O-Ps expression (17). The current study has allowed us to create stable, minimal-sized *S. sonnei* form I region constructs in Ty21a. The stability of plasmid-based expression of form I O-Ps was enhanced by deletion of the downstream IS91 from form I inserts and was further stabilized by use of the low copy vector pGB-2 (Table 3). Animal studies (Table 4) have provided preclinical evidence that these minimal-sized form I region constructs in *S. Typhi* induced protective immunity in a stringent mouse challenge model.

REFERENCES

1. Belanger, M., L. L. Burrows, and J. S. Lam. 1999. Functional analysis of genes responsible for the synthesis of the B- band O antigen of *Pseudomonas aeruginosa* serotype O6 lipopolysaccharide. Microbiology. 145:3505-21.
2. Bilge, S. S., J. C. Vary, Jr., S. F. Dowell, and P. I. Tarr. 1996. Role of the *Escherichia coli* O157:H7 O side chain in adherence and analysis of an rfb locus. Infect Immun. 64:4795-801.
3. Black, R. E., M. M. Levine, M. L. Clements, G. Losonsky, D. Herrington, S. Berman, and S. B. Formal. 1987. Prevention of shigellosis by a *Salmonella typhi-Shigella sonnei* bivalent vaccine. J Infect Dis. 155:1260-5.
4. Bolivar, F. 1978. Construction and characterization of new cloning vehicles. III. Derivatives of plasmid pBR322 carrying unique Eco RI sites for selection of Eco RI generated recombinant DNA molecules. Gene. 4:121-36.
5. Burrows, L. L., R. V. Urbanic, and J. S. Lam. 2000. Functional conservation of the polysaccharide biosynthetic protein WbpM and its homologues in *Pseudomonas aeruginosa* and other medically significant bacteria. Infect Immun. 68:931-6.
6. Chida, T., N. Okamura, K. Ohtani, Y. Yoshida, E. Arakawa, and H. Watanabe. 2000. The complete DNA sequence of the O antigen gene region of *Plesiomonas shigelloides* serotype O17 which is identical to *Shigella sonnei* form I antigen. Microbiol Immunol. 44:161-72.
7. Churchward, G., D. Belin, and Y. Nagamine. 1984. A pSC101-derived plasmid which shows no sequence homology to other commonly used cloning vectors. Gene. 31:165-71.
8. Creuzenet, C., M. Schurr, J. Li, W. W. Wakarchuk, and J. S. Lam. 2000. FlaA1, a new bifunctional UDP-GlcNAc C6 dehydratase/C4 reductase from *Helicobacter pylori*. J Biol. Chem. 275:34873-80.
9. DuPont, H. L., R. B. Homick, M. J. Snyder, J. P. Libonati, S. B. Formal, and E. J. Gangarosa. 1972. Immunity in shigellosis. L Response of man to attenuated strains of *Shigella*. J Infect Dis. 125:5-11.
10. DuPont, H. L., R. B. Homick, M. J. Snyder, J. P. Libonati, S. B. Formal, and E. J. Gangarosa. 1972. Immunity in shigellosis. II. Protection induced by oral live vaccine or primary infection. J Infect Dis. 125:12-6.
11. Ertesvag, H., B. Doseth, B. Larsen, G. Skjak-Braek, and S. Valla. 1994. Cloning and expression of an *Azotobacter vinelandii* mannuronan C-5-epimerase gene. J. Bacteriol. 176:2846-53.
12. Formal, S. B., L. S. Baron, D. J. Kopecko, O. Washington, C. Powell, and C. A. Life. 1981. Construction of a potential bivalent vaccine strain: introduction of *Shigella sonnei* form I antigen genes into the galE *Salmonella typhi* Ty21a typhoid vaccine strain. Infect Immun. 34:746-50.
13. Franklin, M. J., C. E. Chitnis, P. Gacesa, A. Sonesson, D. C. White, and D. E. Ohman. 1994. *Pseudomonas aeruginosa* AlgG is a polymer level alginate C5-mannuronan epimerase. J. Bacteriol. 176:1821-30.
14. Germanier, R., and E. Furer. 1975. Isolation and characterization of Gal E mutant Ty 21a of *Salmonella typhi*: a candidate strain for a live, oral typhoid vaccine. J Infect Dis. 131:553-8.
15. Goldman, R. C., D. White, F. Orskov, I. Orskov, P. D. Rick, M. S. Lewis, A. K. Bhattacharjee, and L. Leive. 1982. A surface polysaccharide of *Escherichia coli* O111 contains O-antigen and inhibits agglutination of cells by O-antiserum. J. Bacteriol. 151:1210-21.
16. Gotschlich, E. C. 1994. Genetic locus for the biosynthesis of the variable portion of *Neisseria gonorrhoeae* lipooligosaccharide. J Exp Med. 180:2181-90.

17. Hartman, A. B., M. M. Ruiz, and C. L. Schultz. 1991. Molecular analysis of variant plasmid forms of a bivalent *Salmonella typhi-Shigella sonnei* vaccine strain. J Clin Microbiol. 29:27-32.
18. Hartman, A. B., and M. M. Venkatesan. 1998. Construction of a stable attenuated *Shigella sonnei* DeltavirG vaccine strain, WRSS1, and protective efficacy and immunogenicity in the guinea pig keratoconjunctivitis model. Infect Immun. 66:4572-6.
19. Hashimoto, Y., N. Li, H. Yokoyama, and T. Ezaki. 1993. Complete nucleotide sequence and molecular characterization of ViaB region encoding Vi antigen in *Salmonella typhi*. J. Bacteriol. 175:4456-65.
20. Heinrichs, D. E., M. A. Monteiro, M. B. Perry, and C. Whitfield. 1998. The assembly system for the lipopolysaccharide R2 core-type of *Escherichia coli* is a hybrid of those found in *Escherichia coli* K-12 and *Salmonella enterica*. Structure and function of the R2 WaaK and WaaL homologs. J Biol. Chem. 273:8849-59.
21. Herrington, D. A., L. Van de Verg, S. B. Formal, T. L. Hale, B. D. Tall, S. J. Cryz, E. C. Tramont, and M. M. Levine. 1990. Studies in volunteers to evaluate candidate *Shigella* vaccines: further experience with a bivalent *Salmonella typhi-Shigella sonnei* vaccine and protection conferred by previous *Shigella sonnei* disease. Vaccine. 8:353-7.
22. Hitchcock, P. J., and T. M. Brown. 1983. Morphological heterogeneity among *Salmonella* lipopolysaccharide chemotypes in silver-stained polyacrylamide gels. J. Bacteriol. 154:269-77.
23. Hohn, B., and J. Collins. 1980. A small cosmid for efficient cloning of large DNA fragments. Gene. 11:291-8.
24. Houng, H. S., and M. M. Venkatesan. 1998. Genetic analysis of *Shigella sonnei* form I antigen: identification of a novel IS630 as an essential element for the form I antigen expression. Microb Pathog. 25:165-73.
25. Kenne, L., B. Lindberg, K. Petersson, E. Katzenellenbogen, and E. Romanowska. 1980. Structural studies of the O-specific side-chains of the *Shigella sonnei* phase I lipopolysaccharide. Carbohydr. Res. 78:119-26.
26. Kopecko, D. J., O. Washington, and S. B. Formal. 1980. Genetic and physical evidence for plasmid control of *Shigella sonnei* form I cell surface antigen. Infect Immun. 29:207-14.
27. Kotloff, K. L., J. P. Winickoff, B. Ivanoff, J. D. Clemens, D. L. Swerdlow, P. J. Sansonetti, G. K. Adak, and M. M. Levine. 1999. Global burden of *Shigella* infections: implications for vaccine development and implementation of control strategies. Bull World Health Organ. 77:651-66.
28. Laemmli, U. K. 1970. Cleavage of structural proteins during the assembly of the head of bacteriophage T4. Nature. 227:680-5.
29. Lai, V., L. Wang, and P. R. Reeves. 1998. *Escherichia coli* clone Sonnei (*Shigella sonnei*) had a chromosomal O-antigen gene cluster prior to gaining its current plasmid-borne O-antigen genes. J. Bacteriol. 180:2983-6.
30. Li, J., A. Hagner-McWhirter, L. Kjellen, J. Palgi, M. Jalkanen, and U. Lindahl. 1997. Biosynthesis of heparin/heparan sulfate. cDNA cloning and expression of D-glucuronyl C5-epimerase from bovine lung. J Biol. Chem. 272:28158-63.
31. Matsutani, S., and E. Ohtsubo. 1990. Complete sequence of IS629. Nucleic Acids Res. 18:1899.
32. Mead, P. S., L. Slutsker, V. Dietz, L. F. McCaig, J. S. Bresee, C. Shapiro, P. M. Griffin, and R. V. Tauxe. 1999. Food-related illness and death in the United States. Emerg Infect Dis. 5:607-625.
33. Mendiola, M. V., Y. Jubete, and F. de la Cruz. 1992. DNA sequence of IS91 and identification of the transposase gene. J. Bacteriol. 174:1345-51.
34. Paulsen, I. T., J. H. Park, P. S. Choi, and M. H. Saier, Jr. 1997. A family of gram-negative bacterial outer membrane factors that function in the export of proteins, carbohydrates, drugs and heavy metals from gram-negative bacteria. FEMS Microbiol Lett. 156:1-8.
35. Sambrook, J., E. F. Fritsch, and T. Maniatis. 1989. In Molecular Cloning: A Laboratory Manual. 2nd edition.
36. Sansonetti, P. J., D. J. Kopecko, and S. B. Formal. 1981. *Shigella sonnei* plasmids: evidence that a large plasmid is necessary for virulence. Infect Immun. 34:75-83.
37. Seid, R. C., Jr., D. J. Kopecko, J. C. Sadoff, H. Schneider, L. S. Baron, and S. B. Formal. 1984. Unusual lipopolysaccharide antigens of a *Salmonella typhi* oral vaccine strain expressing the *Shigella sonnei* form I antigen. J Biol. Chem. 259:9028-34.
38. Shepherd, J. G., L. Wang, and P. R. Reeves. 2000. Comparison of O-antigen gene clusters of *Escherichia coli* (*Shigella*) *sonnei* and *Plesiomonas shigelloides* O17: *sonnei* gained its current plasmid-borne O-antigen genes from *P. shigelloides* in a recent event. Infect Immun. 68:6056-61.
39. Stroeher, U. H., L. E. Karageorgos, M. H. Brown, R. Morona, and P. A. Manning. 1995. A putative pathway for perosamine biosynthesis is the first function encoded within the rfb region of *Vibrio cholerae* O1. Gene. 166:3342.
40. Van de Verg, L., D. A. Herrington, J. R. Murphy, S. S. Wasserman, S. B. Formal, and M. M. Levine. 1990. Specific immunoglobulin A-secreting cells in peripheral blood of humans following oral immunization with a bivalent *Salmonella typhi-Shigella sonnei* vaccine or infection by pathogenic *S. sonnei*. Infect Immun. 58:2002-4.
41. Vieira, J., and J. Messing. 1982. The pUC plasmids, an M13 mp7-derived system for insertion mutagenesis and sequencing with synthetic universal primers. Gene. 19:259-68.
42. Viret, J. F., S. J. Cryz, Jr., A. B. Lang, and D. Favre. 1993. Molecular cloning and characterization of the genetic determinants that express the complete *Shigella* serotype D (*Shigella sonnei*) lipopolysaccharide in heterologous live attenuated vaccine strains. Mol Microbiol. 7:239-52.
43. Wang, L., S. Jensen, R. Hallman, and P. R. Reeves. 1998. Expression of the O antigen gene cluster is regulated by RfaH through the JUMPstart sequence. FEMS Microbiol Lett. 165:201-6.
44. Whitfield, C., and I. S. Roberts. 1999. Structure, assembly and regulation of expression of capsules in *Escherichia coli*. Mol Microbiol. 31:1307-19.
45. Yoshida, Y., N. Okamura, J. Kato, and H. Watanabe. 1991. Molecular cloning and characterization of form I antigen genes of *Shigella sonnei*. J Gen Microbiol; 137:867-74.
46. Zhao, X., C. Creuzenet, M. Belanger, E. Egbosimba, J. Li, and J. S. Lam. 2000. WbpO, a UDP-N-Acetyl-D-galactosamine dehydrogenase from *Pseudomonas aeruginosa* serotype O6. J Biol. Chem. 275:33252-9.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An immunoprotective composition comprising *Salmonella enterica* serovar Typhi strain Ty21a expressing an antigen comprising the *S. sonnei* form I O-polysaccharide wherein said strain Ty21a comprises a polynucleotide comprising the genes wbgT, wbgU, wzx, wzy, wbgV, wbgW, wbgX, wbgY, and wbgZ from the *S. sonnei* rfb/rfc gene cluster or *Plesiomonas shigelloides* (*P. shigelloides*) O17 gene cluster operably linked to transcriptional promoter and termination signals, wherein the polynucleotide does not include at least one of the following genes: IS1, wzz, IS630, aqpZ, IS629, IS91, and IS911.

2. The immunoprotective composition of claim 1, wherein said polynucleotide comprises SEQ ID NO:2, SEQ ID NO:3, or SEQ ID NO:4 operably linked to a promoter.

3. The immunoprotective composition of claim 1, wherein said antigen is expressed from a recombinant plasmid.

4. The immunoprotective composition of claim 3, wherein said recombinant plasmid contains a selectable marker.

5. The immunoprotective composition of claim 4, wherein said selectable marker is aspartate β-semialdehyde dehydrogenase (asd) gene operably linked to a promoter.

6. The immunoprotective composition of claim 3, wherein said recombinant plasmid comprises SEQ ID NO: 2 operably linked to a promoter.

7. The immunoprotective composition of claim 3, wherein said recombinant plasmid comprises SEQ ID NO: 3 operably linked to a promoter.

8. The immunoprotective composition of claim 3, wherein said recombinant plasmid comprises SEQ ID NO: 4 operably linked to a promoter.

9. The immunoprotective composition of claim 1 further comprising a pharmaceutical diluent.

10. A method of protecting a susceptible host against an infection of *Shigella sonnei* (*S. sonnei*) comprising administering to said host an amount of the immunoprotective composition of claim 1 sufficient to invoke an immunoprotective response in the host.

11. A method of protecting a susceptible host against an infection of *Shigella sonnei* (*S. sonnei*) comprising administering to said host an amount of the immunoprotective composition of claim 3 sufficient to invoke an immunoprotective response in the host.

12. A method of protecting a susceptible host against an infection of *Shigella sonnei* (*S. sonnei*) comprising administering to said host an amount of the immunoprotective composition of claim 2 sufficient to invoke an immunoprotective response in the host.

13. The method of claim 12, wherein the composition is in a pharmaceutically acceptable carrier.

14. The method of claim 12, wherein the composition is in a sterile medium.

15. The method of claim 12, wherein said sterile medium comprises an adjuvant.

16. An isolated *Salmonella enterica* serovar Typhi strain Ty21a expressing an *S. sonnei* form I O-polysaccharide antigen, wherein said Ty21a strain comprises:

a polynucleotide comprising the genes wbgT, wbgU, wzx, wzy, wbgV, wbgW, wbgX, wbgY and wbgZ from the *S. sonnei* rfb/rfc gene cluster or *Plesiomonas shigelloides* (*P. shigelloides*) O17 gene cluster operably linked to transcriptional promoter and termination signals, wherein the polynucleotide does not include at least one of the following genes: IS1, wzz, IS630, aqpZ, IS629, IS91 and IS911.

17. The strain Ty21a of claim 16, wherein said genes wbgT, wbgU, wzx, wzy, wbgV, wbgW, wbgX, wbgY, and wbgZ are isolated from the *S. sonnei* rfb/rfc gene cluster.

18. The strain Ty21a of claim 16, wherein said genes wbgT, wbgU, wzx, wzy, wbgV, wbgW, wbgX, wbgY, and wbgZ are isolated from the *Plesiomonas shigelloides* (*P. shigelloides*) O17 gene cluster.

19. The strain Ty21a of claim 16, wherein said polynucleotide comprises SEQ ID NO: 2 operably linked to a promoter.

20. The strain Ty21a of claim 16, wherein said polynucleotide comprises SEQ ID NO: 3 operably linked to a promoter.

21. The strain Ty21a of claim 16, wherein said polynucleotide comprises SEQ ID NO: 4 operably linked to a promoter.

22. The strain Ty21a of claim 16, wherein said transcriptional promoter is a constitutive promoter.

23. The immunoprotective composition of claim 1, wherein the polynucleotide does not include the following genes: IS1, wzz, IS630, aqpZ,IS629, IS91 and IS911.

24. The strain Ty21a of claim 16, wherein the polynucleotide does not include the following genes: IS1, wzz, IS630, aqpZ, IS629, IS91 and IS911.

* * * * *

SEQUENCE LISTING

<160> NUMBER OF SEQ ID NOS: 22

<210> SEQ ID NO 1
<211> LENGTH: 15690
<212> TYPE: DNA
<213> ORGANISM: Shigella sonnei
<220> FEATURE:
<223> OTHER INFORMATION: 15.7 kb HindIII fragment from AF294823 (SEQ ID NO:7 positions 1310-16999) encoding Shigella sonnei O antigen gene cluster

<400> SEQUENCE: 1

```
aagcttgatc aaatagctca tattcagcga gatttaacaa ctgcggaaca agccggaatc      60
attgattatc gctctagcaa aggcggcttc gataatgcgc aaagtagcta taagttcttg     120
ctcggcgaaa aactgttatc agcagagcta aaagcaacta aagatgcgcc aattatttac     180
ccatttagat attacgaagt gaaacgtcaa attgatgagt tagaaggaat gttacgcgat     240
aacattcagg cgcaagcata tcgatatcaa atgaagccat ctgagccagt tataaaagac     300
aaacccaaca agcattaat tttgattctt ggtgcattac caggggcaat gtttgctata     360
gttggtacat tagtttatgc gacattaaaa gataaaacca agttagatta aactgggtta     420
cgtattgttg tgtcaatgcg aaatagatgt tctatgtgca ctttatgatg gataagaaaa     480
tgaaattcga tactttgaat gcgaaaattg ggattatagg ccttggttat gttggattgc     540
ctcttgctgt tgagtttgga aagaaagtaa cgacgattgg atttgatatt aataagtctc     600
gtattgatga attacgaaat ggtcacgata gtacattaga gtgctcaaat ttagagttgt     660
tagaagcaac taaattgacg tacgcctgtt cattagatgc actaaaagag tgtaatgtat     720
ttattgtaac tgttccaact ccaattgata aacataaaca gccagatcta acacctctaa     780
ttaaagcatc tgaaacattg ggtaagataa taaagaaagg cgatgttatt atttatgagt     840
caacagttta ccctggagcg acagaagaag attgtatacc agttgtagag aaagtatcag     900
gtcttaagtt taatattgat ttttttgccg gttattcacc tgagcgtatt aatcctgggg     960
ataaagagca tcgtgtaact aatatcctta aggtgaccag tggatctaca ccggatgttg    1020
ctgagtatgt agatcagcta tataaattaa taattactgt cggtacgcat aaagcatcat    1080
cgataaaagt agcagaggct gcaaaagtaa ttgaaaacac gcagcgagat gtcaatattg    1140
cattgattaa tgagttatct attatattta ataagttagg gattgatacc ttagaggttc    1200
ttgaggctgc aggtacgaag tggaattttt tacctttag gcccggttta gtaggtggcc    1260
actgtatagg tgtagatcct tattatctta cacataaagc gcaaagtgtc ggctatcatc    1320
cggagatgat tttagccgga cgtcgtttaa atgatagtat ggggcagtat gtcgtttccc    1380
agttagtcaa aaaatgttg aaacaacgga ttcaagttga aggggcgaat gtgttagtga    1440
tggggcttac atttaaagag aattgcccag atctacgaaa cactaaagtg attgatatta    1500
tttcagagtt aaaagaatac aatatcaata tagatattat agatccatgg tgttctaccg    1560
atgaggcaca acatgaatat ggattaactt tatgtgaaga tcctaaagtt aatcattatg    1620
atgcaataat tatcgctgtt gcacacaatg agtttcgcga gatgggagag agcgctattc    1680
gtgcattagg taaagacgag cacgttttgt tcgatttaaa atatgtgctt gataaaaaaa    1740
gtatcgatat gcgcttgtaa gagtgattaa aaaaatcaaa tcctctttga tatgatacac    1800
ctcagcattt tatgctaggt ttagcacttg attaatatac atggatattt atatgtctcg    1860
ctatgaagag attacacagc agttaatttt ttcaccgaaa acttggttaa ttactggtgt    1920
```

```
cgctggcttt ataggatcaa atcttttaga aaagttactt aaattaaacc aggttgttat   1980
tgggttagat aacttttcca cgggacatca atataatctt gatgaagtta aaacattagt   2040
ttccactgaa cagtggagtc gattttgctt tatagaaggt gatattcgag atctcactac   2100
ctgtgagcaa gttatgaaag gtgttgatca tgtcttacat caggctgcgc taggttctgt   2160
acctcgttca attgttgatc ctataacaac caatgcaact aatattactg gattttttgaa  2220 tatcttacat gcggctaaaa atgcacaagt acaaagtttt acttatgctg catcaagctc   2280
aacttatgga gatcatcccg cactaccaaa agtagaggaa acattggta atccactttc    2340 tccttatgca gttactaaat atgttaacga gattatgct caggtatatg ctcgaacata    2400
tggttttaaa actattggat tacgttattt taatgtattt ggtcgtcgtc aagatcctaa   2460
tggagcttat gctgcagtaa ttccaaaatg gacagcagca atgcttaaag gtgatgacgt   2520
atatattaat ggcgatggtg aaacgagtcg tgattttgt tatatagata atgttataca    2580
aatgaatata ttatctgcat tagcgaagga cagtgctaaa gataatatat ataatgttgc   2640
agttggtgat agaacaacgt taaatgaatt atctggttac atttatgatg agcttaattt   2700
aattcaccat atcgataaat tgagcattaa gtatagagag tttagatctg gagatgttag   2760
gcattctcag gctgatgtta ctaaggctat agatttacta agtatagac caaatataaa    2820 aatcagagag ggattacgac tttcaatgcc gtggtatgtg agattttaa aaggctaaat    2880 tatattaaca tgaataaata atctatttca cctctgttat taatgcaggg gtgaaaatcc   2940
atgtatttat tctaaatggt cagtgtatgt ttagaaaaat gattgatgca ggtggtacat   3000
ttttacttaa agcaatattt caaataggag ttttttgtta tttcacacat gtgtcagata   3060
ttactacatt tggtattatt agttatgtgt ttactgttta ttggtttgtg cttaacttct   3120
ctgattatgg atttagaaca aaattagtga agatatttc tgataatagt tattctgcat   3180
cagaattatt atcaagaagt gatggagtta aaacatatgt tttttcttc attttttataa  3240 tcttcatgtt ttattcttat gtttctgatt caatttcatt aactctgctt gtttatattt   3300
catctgcata ttttgtttgt atttcaagtg gtagatttag cttgctacag gctgttggtc   3360
ggtttagatg tgaattatat ataaatatct actcaacaat tatatatatt gggtgtaatt   3420
tatttttatc tctgtttatc gaacctctat attatagtgc gatatcaata ttcatatact   3480
caatttcgct tttggtttc tcatcacata aatgcaatgt gccatgtttt catataaaaa    3540
gaccaagtat tttagtttat aaagatttt tggatgcaac tccgttcgct attctggtgt    3600
tactaaatgt tgttttatct agtattgacc tttttatatt aaaagaatat ttctcttata   3660
atagtgttgc tatatatcag gtggtaacta gggttaatac cggtctaata atagtgttta   3720 atgttatttta tactgtttta ttgccttcat tttcttatta tctgaaaaat tctgaatggg   3780
gtaatataag gaaattacaa cgatatatat cactgttagt cttattacta tgtttatgct   3840
attatttttt tggcatctat ttcgtaggga tattgtttgg tgatgagtat aaggtaatat   3900
cttctgcaac atttttgata atgtttatgg ctcttattaa atataatttt tggctaataa   3960
atgaacttta tcttgtgtgt agtggaaatc aaagcgagcg agttaaatcg tattgtattg   4020
gtgtggtcat ttcaatggcg gtttcttt attttatacc tcggtatgga tggagtgggg    4080 cggttttttgg aagtgccatt gcaacattag taattggaat attttatatt atttctgtga   4140
aaaaagattg tgggaaaatt cttcatgata agtattcact aatgatgatc tttgtcccaa   4200
ttttctttta ttttattatt aatggtcagc agcggttgtt atattaatat gttgtggttt   4260
tatatcgttc cattaatatg tttagactcg attggaagcc taataaaggt taagtatgtt   4320
```

```
aatataccta tatcctgtac ttttgttatt taatatcctt ccggttttt ttttatggaca    4380
aatgaactct gatttagagc gttttttttgg agttcctatt ggctatattc cagatctaat    4440
attttatttc tttgttgttt taacatctat aataacgttg aggttcacg tttctctgtg      4500
gacaaagaaa ttattatttt taggcatcat attcctgatt tatatcagca ttcagatgtt    4560
gttgttatca gcggatatat caggtgtcgt aatttatta tcgttttttt ctaattttat      4620
agctttggtt cttttggtgt catttgcat tggtaaagat gagctttatt taactcattc      4680
ggttagaaat ataaatgttg taatgtgttt tggtattatc tgtggagttg taaaattatt    4740
tattggttat tctgaagata gtaatttttat agtttattta aatagaaatg ccaccgcaat    4800
tatagtagtg tgcttttatt gtgtatattc atactttat cgtggtcgaa agtcttggta     4860
tgtctcatct gtattgtact ctctgttctt tcttttctg gatagccgag caggaataat     4920
atcatttgct atatcgttgt tttttgtttt tcttcagtta acaaagaagg aaaagttatt    4980
aatatcattg ttttttgttc ctcttctaac tttaggtatt tcttttactg atataggcac    5040
tcgtcttgaa cgaatgctgt cttcgtcaca ggttatattc tctggtggta acactcttac    5100
aaaaagtcag aatgattatc gtcgagttga gttagtattt attggggttg atgttttaaa    5160
agaaaattat ttaattggca ctggattagg tgttgcaaat tatgtaaagg ctatagataa    5220
aaagttttta ggaagtacca actttgggtt ggcgcataat ttttatttat cttattcggc    5280
tcagttaggg attattggtt ttattttgct tatttctgta ttttatataa tgctgtctcc    5340
aattttttaaa tgcggagggt atattggtaa aggatgcgtt tttgctttgg ctttctatgt    5400
cttttttaat gagtatatat tgacgccagc gatatatatt tatatttcta ttttttttatc    5460
ggtggttttt atacgtaatt ctaaatagct gcgcggaata gtagatcact ttgagggaac    5520
ttagcccgga ttgtgcgatc tgatcaatcg ccaaatcaaa acaaatcacc aaccggactg    5580
agcaatgccg atcatagcac caatttcccg tgacgaacga cgcctgatgc agaaagccat    5640
ccataaaaca cacgataaaa attatgcccg cagactgact gccatgctga tgctgcaccg    5700
gggcgaccgt gtcagcgacg ttgccagaac gctctgctgc gcccgttcct ctgttggacg    5760
ctggattaac tggttcacgc agtcgggtgt tgagggactg aaatcattac ctgccgggcg    5820
tgcccgtcgc tggccgtttg agcatatctg cacactgtta cgtgagctgg taaaacattc    5880
tcccggcgac tttggctacc agcgttcacg ctggagtaca gaactgctgg caataaaaat    5940
caatgagata accggttgcc agttaaatgc cggaaccgtt cgccgctggt tgccgtctgc    6000
ggggattgtg tggcgaaggg ctgcgccaac tctgcgtatc cgtgacccgc ataaagatga    6060
aaagatggca gcaatccata aagcactgga cgaatgcagc gcagagcatc cggtcttta    6120
tgaagatgaa gtggatatcc atcttaatcc caaatcggt gcggactggc aactgcgcgg    6180
acagcaaaaa cgggtggtca cgccgggaca gaatgaaaaa tattatctgg ccggagcgct    6240
gcacagcggg acaggtaaag tcagctgtgt gggcggcaac agcaaaagtt cggcgctgtt    6300
catcagcctg ctgaagcggc ttaaagcgac ataccgtcgg gcgaaaacca tcacgctgat    6360
cgtggacaac tacattatcc acaaaagccg ggaaacacag agctggctga aggagaaccc    6420
gaagttcagg gtcatttatc agccggttta ctcgccatgg atgaatcatg ttgaacggct    6480
atggcaggca cttcacgaca caataacgcg taatcatcag tgcagctcaa tgtgcaact     6540
gttgaaaaaa gttcgccatt ttatggaaac cgtcagccca ttccccggag gcaaacatgg    6600
gctggcaaaa gtgtagcggt attaagcgca gctatttagg atgagaatat gttgttagaa    6660
tatgttgaaa gaaaaatttc cttagccttg agtaagtatc ctaaggtaag ggatgttatt    6720
```

```
aagttctttt atttatatat cgcatcatta ttcggaatta ttttgaataa aaataagacg    6780
gttattcaat caaaaatata cgagatttca attgatgatt ctgaagaatc atttttggc    6840
tattatgacc atagtccaat gagctctaat gggcggtacg tattgttcca ctctagtgcg    6900
tttagcacta aacgacatcc aaagaaagtt aagtatatat ctatttgcgt aaaagacctt    6960
cttaataaca aagtttataa gctatatgat acgcgagcat ttaattggca gcagggaagc    7020
cgattaatgt ggattgatga tgacaatata attttaatg actatgaaaa taatggatac     7080
attagtgttg tctattcttt gtctttgatg aaggttataa aaaaataaa ctatccgatt     7140
tatgatgtga ataattacaa ggctgtgacg ttagatttct catggctggc taaatatgat    7200
agcgattatg gttattataa taaaaaatca ttttctacag atatttcaat cattaatttg    7260
aatacggggg gaatagaatt attttatcc ttagacgaaa tgctaaagag aactaatttt     7320
aaatgtaata ttgatgttga acatgtggtc aatcatttta tgtttgctcc cgatggacgt    7380
tccgttatgt tcatacatcg atactataca cctaaaggaa agcgtgaaag gttaatacat    7440
tggaatttaa taaatgataa tgttcgagtc ctaataaatg aatcgattat tagtcattgt    7500
tgttggaatg ggaatgatga aattataggt tttttggtg cagaaataga ttcgctaaat     7560
tattatagat tgtcaattga atcctgtaat acagagaaat tgttttttga tgcaagaaaa    7620
tattctgatg gacatcctac tatagttcat aatagatata ttatatctga tacttaccca    7680
gataaaaata gaattaaaaa gttgtttgtt tatgaccttg tcaaaaatga ttatcgcgag    7740
cttggattat tttatgagtc aatgagtttt ttttcttatt ctcgatgtga cttacatcca    7800
aggatctcgg ttgataatag attttttgttt gttgattcag ttcactcagg gaaaagaaaa    7860
ctatatttta tgaggagtgg tatttgtgag tgatgttcta gtatctttaa ttatagtttg    7920
ctttaatgca gagaagtata ttgaaaaatc tcttttggca tttattaatc aagatgttgg    7980
attagataaa tttgaattga ttattgtaga tggggattca tctgataata caatatctat    8040
tgttcaggat gttttttcta aacatagcaa cattaagcat aaaattatca ataataaaaa    8100
aagaactctt gctacgggtt ggaatattgg ggtgctagaa gctaatggta agtttgtgtg    8160
tagagttgat gcacatagtg atattccaaa taactatata tctaaattat tagatgatta    8220
ttttaatatt atgcagtttg atgatagcgt tgttggtgtt ggaggtgtat taactaattc    8280
ttataaaact aagtttggtt caattgtagc ggatttttat gcatcgaaat ttggtgttgg    8340
taattctcca tttaggtgcg tagacaaaaa taatcgacta aaaaaaacag atacagctgt    8400
ctttgcttta tataataaag atgtgttttt tgatgttgga cttttttaatg aagtattaga    8460
tagaaatcaa gatattgatt ttcataagag agttttaagc aataatttgt cattatatac    8520
agataatagt ttatttgttg agtattatgt tagagataat tttaaagatt tcataaagaa    8580
aggttttctt gatggttttt gggttgttat gtctggagca tattatttta gacatatagt    8640
gccacttttt tttgtttttgt atttaattgt atctttttct cttttctttg ctactggtga    8700
ttatatatat ttatcttttt tatttttta ttttcttatt tctattttgt tttcaattcg     8760
agatgggcga agtttatag gtagagtatt tcttccttt atattttgt cttatcatat        8820
ttcttatgga tgtggatcgt tattatcttt tttgaaaagg tattttaaat gaaaatttt       8880
attccttttg cgttacctga aattggcgaa gaagaaattg cagaggtaat tgactcttta    8940
cgttcaggtt ggattacgac aggtcctaag gctaagcaat tgaacaaga attttctaat      9000
tacctaggag cgaacgttca atcattagct gttaactctg ctacgtcggg cttacatttg    9060
gctcttgaag ctgttggcgt aaagccggga gaccaagtta ttgtcccatc atatacattc    9120
```

```
actgctactg ccgaaattgt caggtacctt ggtgctgatc ctgtaattgt tgatgtagat    9180
cgtaaaacat ttaatatatc agttgatgcc attgagaagg ctattactaa tgaaacaaag    9240
gcgattattc cagtcacttt cgctggatta gcttgtgaca tggattcaat cttatcaatt    9300
gctaaaaaat atgacctaaa ggttgtcgag gatgccgctc atgcatttcc tacaacatat    9360
aaaggaagta agataggaac gcttgattca gatgctacgg ttttagctt ctacgccaat     9420
aaaactatga caaccggtga aggcggaatg gttgtttcaa aaaataaaga tataattgag    9480
cgttgtaagg taatgcgttt acatggaatc agtcgtgacg cttttgaccg gtaccagtct    9540
aaaactcctt cttggtttta tgaggttgta gctccagggt ttaaatacaa tatgcctgat    9600
atctgtgcgg caatcggtat tcatcaactt agaaagatcg atgattttca gaaaaaacgt    9660
caacgaatgg caaaaattta cgatgatgcg ttaaagaat tgccacttga attgcctgaa     9720
tggcctacta atgctagtga tattcatgct tggcatctat atcctatccg cttaaaaact    9780
gattcggcta ttaatcgcga tgattttatt aagaagttat cagatcttgg aattggttgt    9840
tctgtccatt ttataccgtt gcataagcaa ccggtttggc gtgatacata aatttgaac     9900
gccagtgact ttccagtttc tgaggagtgt tatttaaatg aaatatctat tcctcttat     9960
actaaaatga cggatcaaga tcagttgttc gttatcaaat cgattagaca attatttatg   10020
taatggtatt ttatattaaa tgaaacgtat ttttgatgtt atcgtggcag cttaggcct    10080
gcttttttcta tttcctgttt ttatcattgt gtcaatgtta attgttgctg attctaaagg   10140
ggggttttt tttaggcagt atagagttgg gagatttggg aaagatttta ggatacataa    10200
atttagaacg atgtttatcg attcagaaaa aaaaggacgg ataacagttg gtcaagatgc   10260
tcgggtaacc agagttggat ggtatttacg gaagtacaaa atcgatgagc ttcctcaatt   10320
gatagatgtt ctttctggaa caatgagttt ggttggccca agaccggaag tgagggagtt   10380
tattgatgag tatcctgatg atataaggga aaaagtttta tcggttaggc cagggataac   10440
tgacttagca tctatagaaa tggtagatga aaatgagatt ttgtctagtt atgatgaccc   10500
acgtagggct tatatagata taattcttcc aatcaagcaa agatattatt tagattatgt   10560
tgctaacaat tcagtaaagt atgattgtgt gataatttgg aaaactatta ttaagatttt   10620
gtcgcgataa taaggtagtg taggatgatt gatagaatat tggagctgcc aagaattgtt   10680
aagagaggta tcatcatctg cattgatgta gttatggtga tattctcatt ttggttgtct   10740
tattggttga ggcttgatga gcaaacggct tttcttagtg caccgatgtg gtttgctgca   10800
gctattctta ccatatttac cgtgtttata tttatcagga ttgggcttta tcgggcagtc   10860
ttacggtatg ttagtgcaaa gataatgttg ctaataccag ttggtattct ggcctcaacg   10920
ttatctcttg tcgttatatc atattcgcta tccataatgt tgccgcgcac tgttgtcgga   10980
attttatttt tggttttact tttactgaca tcaggctcta gattgctttt tagaatgata   11040
cttaactatg gagttaaggg tagtgcgcct gttttgattt atggcgctgg tgaatctggc   11100
cgacaattat tgccagcatt aatgcaggca aaagaatatt ttcctgtggc atttgtggat   11160
gataatcctc gcttgcataa ggctgtcatt catggtgtaa cagtttatcc ctcggataaa   11220
ctgagttacc ttgtagatcg ctatggtata aagaaaattc ttttggcgat gccgagcgtc   11280
agtaagtcac aaaggcagaa agtgattact cgtttagagc atctaccgtg tgaagttctc   11340
tctattccgg gtatggtcga tttagtcgaa ggtcgagcac aaatcagtaa tctaaaaaaa   11400
gtatcgattg atgacttact aggtcgtgat ccggttgctc ctgatgccaa attgatggcc   11460
gaaaacatta ctggcaaagc cgttatggtc actggggcgg gaggctcgat cggctctgag   11520
```

```
ctttgtcgtc aaattgttcg atataagccg gccaaattgg ttctatttga actgtctgaa    11580
tatgccctct acgctattga gaaagagctc tcggcgctgt gcgacaaaga agttttgaat    11640
gttccagtga tccctctgtt gggctcggtg cagcgtcaga atcgcttaca gatggtgatg    11700
aagtcctttg gtattcaaac ggtttatcat gcggccgctt ataaacatgt gcctctggtt    11760
gagcataatg tggtggaagg ggtacgtaat aacgtgtttg gtaccttgta ctgcgctgag    11820
tcagcgatcg aaagtggcgt tgaaactttt gtgttgattt ccaccgataa agcggtgcgc    11880
ccgaccaaca ctatggggac aactaagcgt ctggccgaat tggtattgca ggctttgtct    11940
gcacggcaaa gccaaactcg cttttgtatg gtgcgatttg gtaatgtact cggttcttcg    12000
ggctctgtcg tgccgttgtt tgaaaaacag attgcccaag gtgggccagt taccttgact    12060
catcgtgaca ttattcgcta tttcatgaca attccggaag catcacagtt ggtgattcaa    12120 gcggggcga tggggcatgg cggcgatgtc tttgtcttag acatgggcga tccggtcaag    12180
atttatgact tagccaaacg catgatccgg ttaagtggct tgagtgtacg ggatgataaa    12240
aatccagatg gcgatattgc cattgaagtt acgggattac gtccagggga gaaactgtat    12300
gaagaattac tgattggtga ttcagttcaa ggtacctctc atcccgaat tatgacggcc    12360 aacgaagtga tgctaccgtg gcaggatcta tcgctcttac ttaaagagct ggatcaagct    12420
tgtcatgact ttgatcatga gcgaattcgc agtttgttgt tacaagcacc agcggcattc    12480
aatccaactg atgatatttg cgatctagtt tggcagcaga aaaaatcgct gttatcacaa    12540
gcgagcaatg tcattcgcct gtgattgctt aggtttaacc ttccacacca attcttcacc    12600
tctcttacaa atccccgcta ggcggtacat cgtgaccgcc tttagcctga tgcctgctct    12660
ttaacaaaca ggacatcagt gtatgtttaa accttttagc gccgaatttt tcggcacttt    12720
ctggctggtt ctgggtggct gtggtagcgc cttgatctct gctgctttcc cacagttagg    12780
tataggcttt ttgggcgtgg cgttggcgtt tggtctgaca gtagtcacca tggcttatgc    12840
ggtcgggcac atctctggtg cgcatttaa ccccgcggtg accttgggtc tgtgggccgg    12900
tggacgcttc ccagcagcgc gcgtgttacc ttacattatc gctcaggtta tcggcggtat    12960
tgccgctgcg gcagtgctgt atggtatcgc cagcggtaag gctgggtttg atgcgacaac    13020
cagcggtttt gcggctaatg gttatggcct ccattcacct ggcggctatg cgttaagcgc    13080
ctgtatgctg agcgagttg tcctcagtgc gttttttgtc cggagcgaca gaaaaacgcg    13140
ctcctgcggg ctttgcgcca ctggcgattg gtctggtaat caccccgtaa attaaccagc    13200
gtcaaaagta gaattttctc gtaccataaa cgcaggagat tctttatgca aacatcaaaa    13260
tttaccgaca agcaaatcat ggcgatcctc aaatgaaccc ccccgggaat cctggagact    13320
aaacttcctg agaaagaggt aaacaggatg actaaaaata ctcgtttttc ccccgaagtc    13380
cgtcaacggg cagtccgtat ggttctggaa agtcagggcg aatatgactc acaatgggcg    13440
acaatttgtt ccattgctcc aaagattggc tgtacgccgg agactctgcg tgtccgggtt    13500
cgccagtatg agcgggatac cggggcggt gatggagggc tcaccaccgc tgaacgtcag    13560
cgtctgaaag agctggagcg tgaaaatcgt gaactgcgcc gcagtaacga tatccttcgc    13620
caagcttccg cttatttgc gaaggcggag ttcgaccgcc tctggaaaaa atgatgccac    13680
tgctggataa gctgcgtgag cagtacgggg tcggaccgct atgcagcgaa ctgcatattg    13740
ccccgtcaac gtattaggga tttgaagccc aaccgtacga aaacgtacgc taagttcatt    13800
tcttgaacaa cctggctgac tctatgtatt tgtacagcgt tggcctcgat atccccatca    13860
acacacaaat ctgcgcaact gtatgttttt tctcgttata gagttgaaca gcaagggcct    13920
```

| | |
|---|---:|
| gtttatcctt actcagtgtt ttcggcctgc cgcccttacg tcctctggct cgtgctgctt | 13980 |
| gaagcccgac ctgagttctc tctcttgtca ggttgcgttc atcgatagga attaaaaccc | 14040 |
| caaaaagatt aaaaaaacac cacaaaacgg atgtttcttc aacaccactt ttgctccata | 14100 |
| tgaacggaac cgacgattaa actggatggc tctgattgat tcagggtatg aatggcggtt | 14160 |
| ttttgctccg tttccctcaa aatggacgca acttcccctc tgcggctctc agccgcacca | 14220 |
| ccgcatccgg gccaagcagc tcatgcatca ggacctgctc tgccagacgg tagccccgct | 14280 |
| tcagccccgt aaaacgcatc tgactcccgc acagcacgca cttcagcggg tcaaccttca | 14340 |
| gtaacctctg atacatccct ctccaggtga tttgcatcgc cgttttctc actgtctccg | 14400 |
| ttatgatgta caccacttct tccagtaacc gccgtttcgc cggactcaaa aaccgtagt | 14460 |
| acctcaccat acgaaccccc ttatccgcca catgccagga gaacctttcc atgaactcat | 14520 |
| ctccactcat caacaggtat tcttcccgtt ttgttcggtg actgttgtaa cgcagaccga | 14580 |
| tttcatcctg accggcataa tgctccgac gactcatcgg cactggtggc tttttcaggt | 14640 |
| aagagccaaa gtacaccgcc acatgggtgg cattatccat caccgggat acgttgacat | 14700 |
| tccagccacg gcgtaatgc gtgtccagga agcgattcca ttcccgttta ctgcttcctt | 14760 |
| ctgctgccag cgcatccggc atcaccaggt cagggtattt ccgtgacagc aaccgtgtta | 14820 |
| tccggtagcg ccacatgctc atcaccttac gggcgtaaaa atgaagattt ttccaggtgt | 14880 |
| ggcccgacgt cacaccaccg gcagttgtcg ataaatggat atgcggatgc cactgctggt | 14940 |
| cacgcccca tgtgtggatc accgtgaata tccccgactc acatctgcc tgatggcaga | 15000 |
| tttccagtat cacatccgct gcaatgcggc tcatctctgt cagtaaccac cggttgtgga | 15060 |
| acaccaggga ccagtactgg cagggaagtg tgaacacaat atgctgccac gggcagtcgg | 15120 |
| ggaccaggct cagcagatac tgtatccact gtgcgccagc cttcaccccg cagtgcgggc | 15180 |
| aggagcggct tttacaccgg aagcagacct tttttgtatg gcaacagtcc ggtgatgaac | 15240 |
| agcaccactg tgtataccc atcagtgtgg tcccgcacgc catgatttg gtcaccgact | 15300 |
| caatcaccac cggacgtact gccccttccg gctgcttctc cagccagtta agccagcggt | 15360 |
| ttccctgctg aaagatatcg gcaaaacggg gaagcatcag aagggcgggg cgactccgtc | 15420 |
| cggccagtga accgtgccac actccgggca gtacataccg ccggcgctga taccggaaag | 15480 |
| aatggtcgca aattcccgct ccgtgcagcg ggcgatttcc ggatacctt cgtcatcaac | 15540 |
| acgtacaaac cagaagacca gcttttgtt tcccgcatcc acaaagaacg gaatattcag | 15600 |
| gtctgcgcag cattcaacgg catcgtcaaa actatcaaag cgcagaactt ctgcgtcttc | 15660 |
| ttcgtcaaaa aaatcatctt cgtgaagctt | 15690 |

<210> SEQ ID NO 2
<211> LENGTH: 13627
<212> TYPE: DNA
<213> ORGANISM: Shigella sonnei
<220> FEATURE:
<223> OTHER INFORMATION: 13.7 kb HindIII fragment from AF294823 (SEQ
     ID NO:7 positions 1310-14936) encoding Shigella sonnei O antigen
     gene cluster

<400> SEQUENCE: 2

| | |
|---|---:|
| aagcttgatc aaatagctca tattcagcga gatttaacaa ctgcggaaca agccggaatc | 60 |
| attgattatc gctctagcaa aggcggcttc gataatgcgc aaagtagcta taagttcttg | 120 |
| ctcggcgaaa aactgttatc agcagagcta aaagcaacta aagatgcgcc aattatttac | 180 |
| ccatttagat attacgaagt gaaacgtcaa attgatgagt tagaaggaat gttacgcgat | 240 |

```
aacattcagg cgcaagcata tcgatatcaa atgaagccat ctgagccagt tataaaagac     300
aaacccaaca aagcattaat tttgattctt ggtgcattac caggggcaat gtttgctata     360
gttggtacat tagtttatgc gacattaaaa gataaaacca agttagatta aactgggtta     420
cgtattgttg tgtcaatgcg aaatagatgt tctatgtgca ctttatgatg gataagaaaa     480
tgaaattcga tactttgaat gcgaaaattg ggattatagg ccttggttat gttggattgc     540
ctcttgctgt tgagtttgga aagaaagtaa cgacgattgg atttgatatt aataagtctc     600
gtattgatga attacgaaat ggtcacgata gtacattaga gtgctcaaat ttagagttgt     660
tagaagcaac taaattgacg tacgcctgtt cattagatgc actaaaagag tgtaatgtat     720
ttattgtaac tgttccaact ccaattgata aacataaaca gccagatcta acacctctaa     780
ttaaagcatc tgaaacattg ggtaagataa taaagaaagg cgatgttatt atttatgagt     840
caacagttta ccctggagcg acagaagaag attgtatacc agttgtagag aaagtatcag     900
gtcttaagtt taatattgat tttttgccg gttattcacc tgagcgtatt aatcctgggg     960
ataaagagca tcgtgtaact aatatcctta aggtgaccag tggatctaca ccggatgttg    1020
ctgagtatgt agatcagcta tataaattaa taattactgt cggtacgcat aaagcatcat    1080
cgataaaagt agcagaggct gcaaaagtaa ttgaaaacac gcagcgagat gtcaatattg    1140
cattgattaa tgagttatct attatattta ataagttagg gattgatacc ttagaggttc    1200
ttgaggctgc aggtacgaag tggaattttt tacctttttag gcccggttta gtaggtggcc    1260
actgtatagg tgtagatcct tattatctta cacataaagc gcaaagtgtc ggctatcatc    1320
cggagatgat tttagccgga cgtcgtttaa atgatagtat ggggcagtat gtcgtttccc    1380
agttagtcaa aaaaatgttg aaacaacgga ttcaagttga aggggcgaat gtgttagtga    1440
tggggcttac atttaaagag aattgcccag atctacgaaa cactaaagtg attgatatta    1500
tttcagagtt aaaagaatac aatatcaata tagatattat agatccatgg tgttctaccg    1560
atgaggcaca acatgaatat ggattaactt tatgtgaaga tcctaaagtt aatcattatg    1620
atgcaataat tatcgctgtt gcacacaatg agtttcgcga gatgggagag agcgctattc    1680
gtgcattagg taaagacgag cacgttttgt tcgatttaaa atatgtgctt gataaaaaaa    1740
gtatcgatat gcgcttgtaa gagtgattaa aaaaatcaaa tcctctttga tatgatacac    1800
ctcagcattt tatgctaggt ttagcacttg attaatatac atggatattt atatgtctcg    1860
ctatgaagag attacacagc agttaatttt ttcaccgaaa acttggttaa ttactggtgt    1920
cgctggcttt ataggatcaa atcttttaga aaagttactt aaattaaacc aggttgttat    1980
tgggttagat aacttttcca cgggacatca atataatctt gatgaagtta aaacattagt    2040
ttccactgaa cagtggagtc gattttgctt tatagaaggt gatattcgag atctcactac    2100
ctgtgagcaa ttatgaaag gtgttgatca tgtcttacat caggctgcgc taggttctgt    2160
acctcgttca attgttgatc ctataacaac caatgcaact aatattactg gattttttgaa    2220 tatcttacat gcggctaaaa atgcacaagt acaaagtttt acttatgctg catcaagctc    2280
aacttatgga gatcatcccg cactaccaaa agtagaggaa acattggta atccactttc    2340 tccttatgca gttactaaat atgttaacga gatttatgct caggtatatg ctcgaacata    2400
tggttttaaa actattggat tacgttattt taatgtattt ggtcgtcgtc aagatcctaa    2460
tggagcttat gctgcagtaa ttccaaaatg gacagcagca atgcttaaag gtgatgacgt    2520
atatattaat ggcgatggtg aaacgagtcg tgatttttgt tatatagata atgttataca    2580
aatgaatata ttatctgcat tagcgaagga cagtgctaaa gataatatat ataatgttgc    2640
```

```
agttggtgat agaacaacgt taaatgaatt atctggttac atttatgatg agcttaattt    2700
aattcaccat atcgataaat tgagcattaa gtatagagag tttagatctg gagatgttag    2760
gcattctcag gctgatgtta ctaaggctat agatttacta aagtatagac caaatataaa    2820
aatcagagag ggattacgac tttcaatgcc gtggtatgtg agatttttaa aaggctaaat    2880
tatattaaca tgaataaata atctatttca cctctgttat taatgcaggg gtgaaaatcc    2940
atgtatttat tctaaatggt cagtgtatgt ttagaaaaat gattgatgca ggtggtacat    3000
ttttacttaa agcaatattt caaataggag ttttttgttta tttcacacat gtgtcagata    3060
ttactacatt tggtattatt agttatgtgt ttactgttta ttggtttgtg cttaacttct    3120
ctgattatgg atttagaaca aaattagtga agatatttc tgataatagt tattctgcat    3180
cagaattatt atcaagaagt gatggagtta aaacatatgt ttttttcttc attttttataa    3240 tcttcatgtt ttattcttat gtttctgatt caatttcatt aactctgctt gtttatattt    3300
catctgcata ttttgtttgt atttcaagtg gtagatttag cttgctacag gctgttggtc    3360
ggtttagatg tgaattatat ataaatatct actcaacaat tatatatatt gggtgtaatt    3420 tattttttatc tctgtttatc gaacctctat attatagtgc gatatcaata ttcatatact    3480
caatttcgct tttggttttc tcatcacata aatgcaatgt gccatgtttt catataaaaa    3540
gaccaagtat tttagtttat aaagattttt tggatgcaac tccgttcgct attctggtgt    3600
tactaaatgt tgttttatct agtattgacc tttttatatt aaaagaatat ttctcttata    3660
atagtgttgc tatatatcag gtggtaacta gggttaatac cggtctaata atagtgttta    3720 atgttatta tactgtttta ttgccttcat tttcttatta tctgaaaaat tctgaatggg    3780
gtaatataag gaaattacaa cgatatatat cactgttagt cttattacta tgtttatgct    3840 attattttt tggcatctat ttcgtaggga tattgtttgg tgatgagtat aaggtaatat    3900
cttctgcaac attttttgata atgtttatgg ctcttattaa atataatttt tggctaataa    3960
atgaacttta tcttgtgtgt agtggaaatc aaagcgagcg agttaaatcg tattgtattg    4020
gtgtggtcat ttcaatggcg gttttctttt attttatacc tcggtatgga tggagtgggg    4080 cggttttttgg aagtgccatt gcaacattag taattggaat attttatatt atttctgtga    4140
aaaaagattg tgggaaaatt cttcatgata agtattcact aatgatgatc tttgtcccaa    4200
ttttctttta ttttattatt aatggtcagc agcggttgtt atattaatat gttgtggttt    4260
tatatcgttc cattaatatg tttagactcg attggaagcc taataaaggt taagtatgtt    4320
aatataccta tatcctgtac ttttgttatt taatatcctt ccggtttttt tttatggaca    4380
aatgaactct gatttagagc gtttttttgg agttcctatt ggctatattc cagatctaat    4440 attttattc tttgttgttt taacatctat aataacgttg aggtttcacg tttctctgtg    4500
gacaaagaaa ttattatttt taggcatcat attcctgatt tatatcagca ttcagatgtt    4560
gttgttatca gcggatatat caggtgtcgt aatttttatta tcgttttttt ctaatttat    4620 agctttggtt cttttggtgt cattttgcat tggtaaagat gagctttatt taactcattc    4680
ggttagaaat ataatgttg taatgtgttt tggtattatc tgtggagttg taaaattatt    4740
tattggttat tctgaagata gtaatttat agtttattta aatagaaatg ccaccgcaat    4800
tatagtagtg tgcttttatt gtgtatattc atactttat cgtggtcgaa agtcttggta    4860
tgtctcatct gtattgtact ctctgttctt tcttttttctg gatagccgag caggaataat    4920
atcatttgct atatcgttgt tttttgtttt tcttcagtta acaaagaagg aaaagttatt    4980
aatatcattg ttttttgttc ctcttctaac tttaggtatt tcttttactg atataggcac    5040
```

```
tcgtcttgaa cgaatgctgt cttcgtcaca ggttatattc tctggtggta acactcttac    5100
aaaaagtcag aatgattatc gtcgagttga gttagtattt attggggttg atgttttaaa    5160
agaaaattat ttaattggca ctggattagg tgttgcaaat tatgtaaagg ctatagataa    5220
aaagttttta ggaagtacca actttgggtt ggcgcataat ttttatttat cttattcggc    5280
tcagttaggg attattggtt ttattttgct tatttctgta ttttatataa tgctgtctcc    5340 aattttaaa tgcggagggt atattggtaa aggatgcgtt tttgctttgg ctttctatgt     5400
cttttttaat gagtatatat tgacgccagc gatatatatt tatatttcta ttttttatc    5460 ggtggttttt atacgtaatt ctaaatagct gcgcggaata gtagatcact ttgagggaac    5520
ttagcccgga ttgtgcgatc tgatcaatcg ccaaatcaaa acaaatcacc aaccggactg    5580
agcaatgccg atcatagcac caatttcccg tgacgaacga cgcctgatgc agaaagccat    5640
ccataaaaca cacgataaaa attatgcccg cagactgact gccatgctga tgctgcaccg    5700
gggcgaccgt gtcagcgacg ttgccagaac gctctgctgc gcccgttcct ctgttggacg    5760
ctggattaac tggttcacgc agtcgggtgt tgagggactg aaatcattac ctgccgggcg    5820
tgcccgtcgc tggccgtttg agcatatctg cacactgtta cgtgagctgg taaaacattc    5880
tcccggcgac tttggctacc agcgttcacg ctggagtaca gaactgctgg caataaaaat    5940
caatgagata accggttgcc agttaaatgc cggaaccgtt cgccgctggt tgccgtctgc    6000
ggggattgtg tggcgaaggg ctgcgccaac tctgcgtatc cgtgacccgc ataaagatga    6060
aaagatggca gcaatccata aagcactgga cgaatgcagc gcagagcatc cggtcttta    6120 tgaagatgaa gtggatatcc atcttaatcc caaaatcggt gcggactggc aactgcgcgg    6180
acagcaaaaa cgggtggtca cgccgggaca gaatgaaaaa tattatctgg ccggagcgct    6240
gcacagcggg acaggtaaag tcagctgtgt gggcggcaac agcaaaagtt cggcgctgtt    6300
catcagcctg ctgaagcggc ttaaagcgac ataccgtcgg gcgaaaacca tcacgctgat    6360
cgtggacaac tacattatcc acaaaagccg ggaaacacag agctggctga aggagaaccc    6420
gaagttcagg gtcatttatc agccggttta ctcgccatgg atgaatcatg ttgaacggct    6480
atggcaggca cttcacgaca caataacgcg taatcatcag tgcagctcaa tgtggcaact    6540
gttgaaaaaa gttcgccatt ttatggaaac cgtcagccca ttccccggag gcaaacatgg    6600
gctggcaaaa gtgtagcggt attaagcgca gctatttagg atgagaatat gttgttagaa    6660
tatgttgaaa gaaaaatttc cttagccttg agtaagtatc ctaaggtaag ggatgttatt    6720
aagttctttt atttatatat cgcatcatta ttcggaatta ttttgaataa aaataagacg    6780
gttattcaat caaaaatata cgagatttca attgatgatt ctgaagaatc attttttggc    6840
tattatgacc atagtccaat gagctctaat gggcggtacg tattgttcca ctctagtgcg    6900
tttagcacta acgacatcc aaagaaagtt aagtatatat ctatttgcgt aaaagacctt     6960
cttaataaca aagtttataa gctatatgat acgcgagcat ttaattggca gcagggaagc    7020
cgattaatgt ggattgatga tgacaatata ttttttaatg actatgaaaa taatggatac    7080
attagtgttg tctattcttt gtctttgatg aaggttataa aaaaaataaa ctatccgatt    7140
tatgatgtga ataattacaa ggctgtgacg ttagatttct catggctggc taaatatgat    7200
agcgattatg gttattataa taaaaaatca ttttctacag atatttcaat cattaatttg    7260
aatacggggg gaatagaatt attttttatcc ttagacgaaa tgctaaagag aactaatttt    7320
aaatgtaata ttgatgttga acatgtggtc aatcatttta tgtttgctcc cgatggacgt    7380
tccgttatgt tcatacatcg atactataca cctaaaggaa agcgtgaaag gttaatacat    7440
```

```
tggaatttaa taaatgataa tgttcgagtc ctaataaatg aatcgattat tagtcattgt    7500
tgttggaatg ggaatgatga aattataggt tttttttggtg cagaaataga ttcgctaaat    7560
tattatagat tgtcaattga atcctgtaat acagagaaat tgttttttga tgcaagaaaa    7620
tattctgatg gacatcctac tatagttcat aatagatata ttatatctga tacttaccca    7680
gataaaaata gaattaaaaa gttgtttgtt tatgaccttg tcaaaaatga ttatcgcgag    7740
cttggattat tttatgagtc aatgagtttt ttttcttatt ctcgatgtga cttacatcca    7800
aggatctcgg ttgataatag attttttgttt gttgattcag ttcactcagg gaaaagaaaa    7860
ctatatttta tgaggagtgg tatttgtgag tgatgttcta gtatctttaa ttatagtttg    7920
ctttaatgca gagaagtata ttgaaaaatc tcttttggca tttattaatc aagatgttgg    7980
attagataaa tttgaattga ttattgtaga tggggattca tctgataata caatatctat    8040
tgttcaggat gttttttcta aacatagcaa cattaagcat aaaattatca ataataaaaa    8100
aagaactctt gctacgggtt ggaatattgg ggtgctagaa gctaatggta agtttgtgtg    8160
tagagttgat gcacatagtg atattccaaa taactatata tctaaattat tagatgatta    8220
ttttaatatt atgcagtttg atgatagcgt tgttggtgtt ggaggtgtat taactaattc    8280
ttataaaact aagtttggtt caattgtagc ggattttat gcatcgaaat ttggtgttgg    8340
taattctcca tttaggtgcg tagacaaaaa taatcgacta aaaaaaacag atacagctgt    8400
ctttgcttta tataataaag atgtgttttt tgatgttgga cttttttaatg aagtattaga    8460 tagaaatcaa gatattgatt ttcataagag agttttaagc aataatttgt cattatatac    8520
agataatagt ttatttgttg agtattatgt tagagataat tttaaagatt tcataaagaa    8580
aggttttctt gatggttttt gggttgttat gtctggagca tattatttta gacatatagt    8640
gccacttttt tttgttttgt atttaattgt atcttttct cttttctttg ctactggtga    8700
ttatatatat ttatctttt tatttttta ttttcttatt tctatttttgt tttcaattcg    8760 agatgggcga agttttatag gtagagtatt tcttccttt atattttgt cttatcatat    8820 ttcttatgga tgtggatcgt tattatcttt tttgaaaagg tatttttaaat gaaaaatttt    8880 attccttttg cgttacctga aattggcgaa gaagaaattg cagaggtaat tgactcttta    8940
cgttcaggtt ggattacgac aggtcctaag gctaagcaat tgaacaaga attttctaat    9000 tacctaggag cgaacgttca atcattagct gttaactctg ctacgtcggg cttacatttg    9060
gctcttgaag ctgttggcgt aaagccggga gaccaagtta ttgtcccatc atatacattc    9120
actgctactg ccgaaattgt caggtacctt ggtgctgatc ctgtaattgt tgatgtagat    9180
cgtaaaacat ttaatatatc agttgatgcc attgagaagg ctattactaa tgaaacaaag    9240
gcgattattc cagtacactt cgctggatta gcttgtgaca tggattcaat cttatcaatt    9300 gctaaaaat atgacctaaa ggttgtcgag gatgccgctc atgcattcc tacaacatat    9360 aaaggaagta agataggaac gcttgattca gatgctacgg ttttagctt ctacgccaat    9420 aaaactatga caaccggtga aggcggaatg gttgtttcaa aaaataaaga tataattgag    9480
cgttgtaagg taatgcgttt acatggaatc agtcgtgacg cttttgaccg gtaccagtct    9540
aaaactcctt cttggtttta tgaggttgta gctccagggt ttaaatacaa tatgcctgat    9600
atctgtgcgg caatcggtat tcatcaactt agaaagatcg atgattttca gaaaaaacgt    9660
caacgaatgg caaaaattta cgatgatgcg ttaaagaat tgccacttga attgcctgaa    9720
tggcctacta atgctagtga tattcatgct tggcatctat atcctatccg cttaaaaact    9780
gattcggcta ttaatcgcga tgattttatt aagaagttat cagatcttgg aattggttgt    9840
```

-continued

```
tctgtccatt ttataccgtt gcataagcaa ccggtttggc gtgatacata taatttgaac    9900
gccagtgact ttccagtttc tgaggagtgt tatttaaatg aaatatctat tcctctttat    9960
actaaaatga cggatcaaga tcagttgttc gttatcaaat cgattagaca attatttatg    10020
taatggtatt ttatattaaa tgaaacgtat ttttgatgtt atcgtggcag gcttaggcct    10080 gcttttcta tttcctgttt ttatcattgt gtcaatgtta attgttgctg attctaaagg    10140
gggggttttt tttaggcagt atagagttgg gagatttggg aaagatttta ggatacataa    10200
atttagaacg atgtttatcg attcagaaaa aaaggacgg ataacagttg gtcaagatgc    10260
tcgggtaacc agagttggat ggtatttacg gaagtacaaa atcgatgagc ttcctcaatt    10320
gatagatgtt ctttctggaa caatgagttt ggttggccca agaccggaag tgagggagtt    10380
tattgatgag tatcctgatg atataaggga aaaagtttta tcggttaggc cagggataac    10440
tgacttagca tctatagaaa tggtagatga aaatgagatt ttgtctagtt atgatgaccc    10500
acgtagggct tatatagata taattcttcc aatcaagcaa agatattatt tagattatgt    10560
tgctaacaat tcagtaaagt atgattgtgt gataatttgg aaaactatta ttaagatttt    10620
gtcgcgataa taaggtagtg taggatgatt gatagaatat tggagctgcc aagaattgtt    10680
aagagaggta tcatcatctg cattgatgta gttatggtga tattctcatt ttggttgtct    10740
tattggttga ggcttgatga gcaaacggct tttcttagtg caccgatgtg gtttgctgca    10800
gctattctta ccatatttac cgtgtttata tttatcagga ttgggcttta tcgggcagtc    10860
ttacggtatg ttagtgcaaa gataatgttg ctaataccag ttggtattct ggcctcaacg    10920
ttatctcttg tcgttatatc atattcgcta tccataatgt tgccgcgcac tgttgtcgga    10980 atttatttt tggttttact tttactgaca tcaggctcta gattgctttt tagaatgata    11040
cttaactatg gagttaaggg tagtgcgcct gttttgattt atggcgctgg tgaatctggc    11100
cgacaattat tgccagcatt aatgcaggca aaagaatatt ttcctgtggc atttgtggat    11160
gataatcctc gcttgcataa ggctgtcatt catggtgtaa cagtttatcc ctcggataaa    11220
ctgagttacc ttgtagatcg ctatggtata aagaaaattc ttttggcgat gccgagcgtc    11280
agtaagtcac aaaggcagaa agtgattact cgtttagagc atctaccgtg tgaagttctc    11340
tctattccgg gtatggtcga tttagtcgaa ggtcgagcac aaatcagtaa tctaaaaaaa    11400
gtatcgattg atgacttact aggtcgtgat ccggttgctc ctgatgccaa attgatggcc    11460
gaaaacatta ctggcaaagc cgttatggtc actggggcgg gaggctcgat cggctctgag    11520
ctttgtcgtc aaattgttcg atataagccg gccaaattgg ttctatttga actgtctgaa    11580
tatgccctct acgctattga gaaagagctc tcggcgctgt gcgacaaaga agttttgaat    11640
gttccagtga tccctctgtt gggctcggtg cagcgtcaga atcgcttaca gatggtgatg    11700
aagtcctttg gtattcaaac ggtttatcat gcggccgctt ataaacatgt gcctctggtt    11760
gagcataatg tggtggaagg ggtacgtaat aacgtgtttg gtaccttgta ctgcgctgag    11820
tcagcgatcg aaagtggcgt tgaaactttt gtgttgattt ccaccgataa agcggtgcgc    11880
ccgaccaaca ctatggggac aactaagcgt ctggccgaat tggtattgca ggctttgtct    11940
gcacggcaaa gccaaactcg cttttgtatg gtgcgatttg gtaatgtact cggttcttcg    12000
ggctctgtcg tgccgttgtt tgaaaaacag attgcccaag gtgggccagt taccttgact    12060
catcgtgaca ttattcgcta tttcatgaca attccggaag catcacagtt ggtgattcaa    12120
gcgggggcga tggggcatgg cggcgatgtc tttgtcttag acatgggcga tccggtcaag    12180
atttatgact tagccaaacg catgatccgg ttaagtggct tgagtgtacg ggatgataaa    12240
```

-continued

```
aatccagatg gcgatattgc cattgaagtt acgggattac gtccagggga gaaactgtat    12300
gaagaattac tgattggtga ttcagttcaa ggtacctctc atccacgaat tatgacggcc    12360
aacgaagtga tgctaccgtg gcaggatcta tcgctcttac ttaaagagct ggatcaagct    12420
tgtcatgact ttgatcatga gcgaattcgc agtttgttgt tacaagcacc agcggcattc    12480
aatccaactg atgatatttg cgatctagtt tggcagcaga aaaaatcgct gttatcacaa    12540
gcgagcaatg tcattcgcct gtgattgctt aggtttaacc ttccacacca attcttcacc    12600
tctcttacaa atccccgcta ggcggtacat cgtgaccgcc tttagcctga tgcctgctct    12660
ttaacaaaca ggacatcagt gtatgtttaa accttttagc gccgaatttt tcggcacttt    12720
ctggctggtt ctgggtggct gtggtagcgc cttgatctct gctgctttcc cacagttagg    12780
tataggcttt ttgggcgtgg cgttggcgtt tggtctgaca gtagtcacca tggcttatgc    12840
ggtcgggcac atctctggtg cgcattttaa ccccgcggtg accttgggtc tgtgggccgg    12900
tggacgcttc ccagcagcgc gcgtgttacc ttacattatc gctcaggtta tcggcggtat    12960
tgccgctgcg gcagtgctgt atggtatcgc cagcggtaag gctgggtttg atgcgacaac    13020
cagcggtttt gcggctaatg gttatggcct ccattcacct ggcggctatg cgttaagcgc    13080
ctgtatgctg agcgagtttg tcctcagtgc gttttttgtc cggagcgaca gaaaaacgcg    13140
ctcctgcggg ctttgcgcca ctggcgattg gtctggtaat caccccgtaa attaaccagc    13200
gtcaaaagta gaattttctc gtaccataaa cgcaggagat tctttatgca acatcaaaa     13260 tttaccgaca agcaaatcat ggcgatcctc aaatgaaccc ccccgggaat cctggagact    13320
aaacttcctg agaaagaggt aaacaggatg actaaaaata ctcgttttc cccccgaagtc    13380 cgtcaacggg cagtccgtat ggttctggaa agtcagggcg aatatgactc acaatgggcg    13440
acaatttgtt ccattgctcc aaagattggc tgtacgccgg agactctgcg tgtccgggtt    13500
cgccagtatg agcgggatac cggggggcggt gatggagggc tcaccaccgc tgaacgtcag    13560
cgtctgaaag agctggagcg tgaaaatcgt gaactgcgcc gcagtaacga tatccttcgc    13620
caagctt                                                              13627
```

<210> SEQ ID NO 3
<211> LENGTH: 13307
<212> TYPE: DNA
<213> ORGANISM: Shigella sonnei
<220> FEATURE:
<223> OTHER INFORMATION: 13.3 kb HindIII-SmaI fragment from AF294823
     (SEQ ID NO:7 positions 1310-14616) encoding Shigella sonnei O
     antigen gene cluster

<400> SEQUENCE: 3

```
aagcttgatc aaatagctca tattcagcga gatttaacaa ctgcggaaca agccggaatc     60
attgattatc gctctagcaa aggcggcttc gataatgcgc aaagtagcta aagttcttg    120 ctcggcgaaa aactgttatc agcagagcta aagcaacta agatgcgcc aattatttac     180 ccatttagat attacgaagt gaaacgtcaa attgatgagt tagaaggaat gttacgcgat    240
aacattcagg cgcaagcata tcgatatcaa atgaagccat ctgagccagt tataaaagac    300
aaacccaaca aagcattaat tttgattctt ggtgcattac caggggcaat gtttgctata    360
gttggtacat tagtttatgc gacattaaaa gataaaacca agttagatta aactgggtta    420
cgtattgttg tgtcaatgcg aaatagatgt tctatgtgca ctttatgatg gataagaaaa    480
tgaaattcga tactttgaat gcgaaaattg ggattatagg ccttggttat gttggattgc    540
ctcttgctgt tgagtttgga agaaagtaa cgacgattgg atttgatatt aataagtctc    600
```

-continued

```
gtattgatga attacgaaat ggtcacgata gtacattaga gtgctcaaat ttagagttgt    660
tagaagcaac taaattgacg tacgcctgtt cattagatgc actaaaagag tgtaatgtat    720
ttattgtaac tgttccaact ccaattgata aacataaaca gccagatcta acacctctaa    780
ttaaagcatc tgaaacattg ggtaagataa taaagaaagg cgatgttatt atttatgagt    840
caacagttta ccctggagcg acagaagaag attgtatacc agttgtagag aaagtatcag    900
gtcttaagtt taatattgat ttttttgccg gttattcacc tgagcgtatt aatcctgggg    960
ataaagagca tcgtgtaact aatatcctta aggtgaccag tggatctaca ccggatgttg   1020
ctgagtatgt agatcagcta tataaattaa taattactgt cggtacgcat aaagcatcat   1080
cgataaaagt agcagaggct gcaaagtaa ttgaaaacac gcagcgagat gtcaatattg   1140
cattgattaa tgagttatct attatattta ataagttagg gattgatacc ttagaggttc   1200
ttgaggctgc aggtacgaag tggaattttt tacctttag gcccggttta gtaggtggcc   1260
actgtataga tgtagatcct tattatctta cacataaagc gcaaagtgtc ggctatcatc   1320
cggagatgat tttagccgga cgtcgtttaa atgatagtat ggggcagtat gtcgtttccc   1380
agttagtcaa aaaaatgttg aaacaacgga ttcaagttga aggggcgaat gtgttagtga   1440
tggggcttac atttaaagag aattgcccag atctacgaaa cactaaagtg attgatatta   1500
tttcagagtt aaaagaatac aatatcaata tagatattat agatccatgg tgttctaccg   1560
atgaggcaca acatgaatat ggattaactt tatgtgaaga tcctaaagtt aatcattatg   1620
atgcaataat tatcgctgtt gcacacaatg agtttcgcga gatgggagag agcgctattc   1680
gtgcattagg taaagacgag cacgttttgt tcgatttaaa atatgtgctt gataaaaaaa   1740
gtatcgatat gcgcttgtaa gagtgattaa aaaaatcaaa tcctctttga tatgatacac   1800
ctcagcattt tatgctaggt ttagcacttg attaatatac atggatattt atatgtctcg   1860
ctatgaagag attacacagc agttaatttt ttcaccgaaa acttggttaa ttactggtgt   1920
cgctggcttt ataggatcaa atcttttaga aaagttactt aaattaaacc aggttgttat   1980
tgggttagat aacttttcca cgggacatca atataatctt gatgaagtta aaacattagt   2040
ttccactgaa cagtggagtc gattttgctt tatagaaggt gatattcgag atctcactac   2100
ctgtgagcaa gttatgaaag gtgttgatca tgtcttacat caggctgcgc taggttctgt   2160
acctcgttca attgttgatc ctataacaac caatgcaact aatattactg gatttttgaa   2220
tatcttacat gcggctaaaa atgcacaagt acaaagtttt acttatgctg catcaagctc   2280
aacttatgga gatcatcccg cactaccaaa agtagaggaa aacattggta atccactttc   2340
tccttatgca gttactaaat atgttaacga gatttatgct caggtatatg ctcgaacata   2400
tggttttaaa actattggat tacgttattt taatgtattt ggtcgtcgtc aagatcctaa   2460
tggagcttat gctgcagtaa ttccaaaatg gacagcagca atgcttaaag gtgatgacgt   2520
atatattaat ggcgatggtg aaacgagtcg tgattttgt tatatagata tgttataca   2580 aatgaatata ttatctgcat tagcgaagga cagtgctaaa gataatatat ataatgttgc   2640
agttggtgat agaacaacgt taaatgaatt atctggttac atttatgatg agcttaattt   2700
aattcaccat atcgataaat tgagcattaa gtatagagag tttagatctg gagatgttag   2760
gcattctcag gctgatgtta ctaaggctat agatttacta agtatagac caaatataaa   2820 aatcagagag ggattacgac tttcaatgcc gtggtatgtg agattttaa aaggctaaat   2880 tatattaaca tgaataaata atctatttca cctctgttat taatgcaggg gtgaaaatcc   2940
atgtatttat tctaaatggt cagtgtatgt ttagaaaaat gattgatgca ggtggtacat   3000
```

```
ttttacttaa agcaatattt caaataggag tttttgttta tttcacacat gtgtcagata    3060
ttactacatt tggtattatt agttatgtgt ttactgttta ttggtttgtg cttaacttct    3120
ctgattatgg atttagaaca aaattagtga agatatttc tgataatagt tattctgcat    3180
cagaattatt atcaagaagt gatggagtta aaacatatgt ttttttcttc attttttataa   3240 tcttcatgtt ttattcttat gtttctgatt caatttcatt aactctgctt gtttatattt    3300
catctgcata ttttgtttgt atttcaagtg gtagatttag cttgctacag gctgttggtc    3360
ggtttagatg tgaattatat ataaatatct actcaacaat tatatatatt gggtgtaatt    3420
tatttttatc tctgtttatc gaacctctat attatagtgc gatatcaata ttcatatact    3480
caatttcgct tttggttttc tcatcacata aatgcaatgt gccatgtttt catataaaaa    3540
gaccaagtat tttagtttat aaagattttt tggatgcaac tccgttcgct attctggtgt    3600
tactaaatgt tgttttatct agtattgacc tttttatatt aaagaatat ttctcttata     3660 atagtgttgc tatatatcag gtggtaacta gggttaatac cggtctaata atagtgttta    3720
atgttattta tactgtttta ttgccttcat tttcttatta tctgaaaaat tctgaatggg    3780
gtaatataag gaaattacaa cgatatatat cactgttagt cttattacta tgtttatgct    3840
attatttttt tggcatctat ttcgtaggga tattgtttgg tgatgagtat aaggtaatat    3900
cttctgcaac attttttgata atgtttatgg ctcttattaa atataatttt tggctaataa   3960
atgaacttta tcttgtgtgt agtggaaatc aaagcgagcg agttaaatcg tattgtattg    4020
gtgtggtcat ttcaatggcg gttttctttt atttttatacc tcggtatgga tggagtgggg   4080 cggttttttgg aagtgccatt gcaacattag taattggaat attttatatt atttctgtga   4140
aaaaagattg tgggaaaatt cttcatgata agtattcact aatgatgatc tttgtcccaa    4200
ttttctttta ttttattatt aatggtcagc agcggttgtt atattaatat gttgtggttt    4260
tatatcgttc cattaaatatg tttagactcg attggaagcc taataaaggt taagtatgtt   4320
aatataccta tatcctgtac ttttgttatt taatatcctt ccggtttttt tttatggaca    4380
aatgaactct gatttagagc gttttttttgg agttcctatt ggctatattc cagatctaat   4440 atttttatttc tttgttgttt taacatctat aataacgttg aggtttcacg tttctctgtg   4500
gacaaagaaa ttattatttt taggcatcat attcctgatt tatatcagca ttcagatgtt    4560
gttgttatca gcggatatat caggtgtcgt aatttttatta tcgtttttttt ctaattttat   4620 agctttggtt cttttggtgt cattttgcat tggtaaagat gagctttatt taactcattc    4680
ggttagaaat ataaatgttg taatgtgttt tggtattatc tgtggagttg taaaattatt    4740
tattggttat tctgaagata gtaatttttat agtttattta aatagaaatg ccaccgcaat    4800
tatagtagtg tgcttttatt gtgtatattc atactttat cgtggtcgaa agtcttggta     4860
tgtctcatct gtattgtact ctctgttctt tcttttttctg gatagccgag caggaataat    4920
atcatttgct atatcgttgt ttttttgtttt tcttcagtta acaaagaagg aaaagttatt    4980
aatatcattg ttttttgttc ctcttctaac tttaggtatt tcttttactg atataggcac    5040
tcgtcttgaa cgaatgctgt cttcgtcaca ggttatattc tctggtggta acactcttac    5100
aaaaagtcag aatgattatc gtcgagttga gttagtatttt attggggttg atgttttaaa   5160
agaaaattat ttaattggca ctggattagg tgttgcaaat tatgtaaagg ctatagataa    5220 aaagtttttta ggaagtacca actttgggtt ggcgcataat ttttatttat cttattcggc   5280
tcagttaggg attattggtt ttattttgct tattctgta ttttatataa tgctgtctcc     5340
aatttttaaa tgcggagggt atattggtaa aggatgcgtt tttgctttgg ctttctatgt    5400
```

-continued

```
cttttttaat gagtatatat tgacgccagc gatatatatt tatatttcta ttttttttatc      5460 ggtggttttt atacgtaatt ctaaatagct gcgcggaata gtagatcact ttgagggaac      5520
ttagcccgga ttgtgcgatc tgatcaatcg ccaaatcaaa acaaatcacc aaccggactg      5580
agcaatgccg atcatagcac caatttcccg tgacgaacga cgcctgatgc agaaagccat      5640
ccataaaaca cacgataaaa attatgcccg cagactgact gccatgctga tgctgcaccg      5700
gggcgaccgt gtcagcgacg ttgccagaac gctctgctgc gcccgttcct ctgttggacg      5760
ctggattaac tggttcacgc agtcgggtgt tgagggactg aaatcattac ctgccgggcg      5820
tgcccgtcgc tggccgtttg agcatatctg cacactgtta cgtgagctgg taaaacattc      5880
tcccggcgac tttggctacc agcgttcacg ctggagtaca gaactgctgg caataaaaat      5940
caatgagata accggttgcc agttaaatgc cggaaccgtt cgccgctggt tgccgtctgc      6000
ggggattgtg tggcgaaggg ctgcgccaac tctgcgtatc cgtgacccgc ataaagatga      6060
aaagatggca gcaatccata aagcactgga cgaatgcagc gcagagcatc cggtcttttta     6120 tgaagatgaa gtggatatcc atcttaatcc caaaatcggt gcggactggc aactgcgcgg      6180
acagcaaaaa cgggtggtca cgccgggaca gaatgaaaaa tattatctgg ccggagcgct      6240
gcacagcggg acaggtaaag tcagctgtgt gggcggcaac agcaaaagtt cggcgctgtt      6300
catcagcctg ctgaagcggc ttaaagcgac ataccgtcgg gcgaaaacca tcacgctgat      6360
cgtggacaac tacattatcc acaaaagccg ggaaacacag agctggctga aggagaaccc      6420
gaagttcagg gtcatttatc agccggttta ctcgccatgg atgaatcatg ttgaacggct      6480
atggcaggca cttcacgaca caataacgcg taatcatcag tgcagctcaa tgtggcaact      6540
gttgaaaaaa gttcgccatt ttatggaaac cgtcagccca ttccccggag gcaaacatgg      6600
gctggcaaaa gtgtagcggt attaagcgca gctatttagg atgagaatat gttgttagaa      6660
tatgttgaaa gaaaaatttc cttagccttg agtaagtatc ctaaggtaag ggatgttatt      6720
aagttctttt atttatatat cgcatcatta ttcggaatta ttttgaataa aaataagacg      6780
gttattcaat caaaaatata cgagatttca attgatgatt ctgaagaatc atttttttggc     6840 tattatgacc atagtccaat gagctctaat gggcggtacg tattgttcca ctctagtgcg      6900
tttagcacta aacgacatcc aaagaaagtt aagtatatat ctatttgcgt aaaagacctt      6960
cttaataaca aagtttataa gctatatgat acgcgagcat ttaattggca gcagggaagc      7020
cgattaatgt ggattgatga tgacaatata attttttaatg actatgaaaa taatggatac      7080
attagtgttg tctattcttt gtctttgatg aaggttataa aaaaaataaa ctatccgatt      7140
tatgatgtga ataattacaa ggctgtgacg ttagatttct catggctggc taaatatgat      7200
agcgattatg gttattataa taaaaaatca ttttctacag atatttcaat cattaatttg      7260
aatacggggg gaatagaatt attttttatcc ttagacgaaa tgctaaagag aactaatttt     7320
aaatgtaata ttgatgttga acatgtggtc aatcatttta tgtttgctcc cgatggacgt      7380
tccgttatgt tcatacatcg atactataca cctaaaggaa agcgtgaaag gttaatacat      7440 tggaattttaa taaatgataa tgttcgagtc ctaataaatg aatcgattat tagtcattgt     7500
tgttggaatg ggaatgatga aattataggt ttttttggtg cagaaataga ttcgctaaat      7560
tattatagat tgtcaattga atcctgtaat acagagaaat tgtttttttga tgcaagaaaa     7620 tattctgatg gacatcctac tatagttcat aatagatata ttatatctga tacttaccca      7680
gataaaaata gaattaaaaa gttgtttgtt tatgaccttg tcaaaaatga ttatcgcgag      7740
cttggattat tttatgagtc aatgagtttt ttttcttatt ctcgatgtga cttacatcca      7800
```

```
aggatctcgg ttgataatag attttttgttt gttgattcag ttcactcagg gaaaagaaaa    7860
ctatatttta tgaggagtgg tatttgtgag tgatgttcta gtatcttttaa ttatagtttg    7920 ctttaatgca gagaagtata ttgaaaaatc tcttttggca tttattaatc aagatgttgg    7980
attagataaa tttgaattga ttattgtaga tggggattca tctgataata caatatctat    8040
tgttcaggat gttttttcta aacatagcaa cattaagcat aaaattatca ataataaaaa    8100
aagaactctt gctacgggtt ggaatattgg ggtgctagaa gctaatggta agtttgtgtg    8160
tagagttgat gcacatagtg atattccaaa taactatata tctaaattat tagatgatta    8220
ttttaatatt atgcagtttg atgatagcgt tgttggtgtt ggaggtgtat taactaattc    8280
ttataaaact aagtttggtt caattgtagc ggattttat gcatcgaaat ttggtgttgg    8340
taattctcca tttaggtgcg tagacaaaaa taatcgacta aaaaaaacag atacagctgt    8400 ctttgctttta tataataaag atgtgttttt tgatgttgga cttttttaatg aagtattaga    8460 tagaaatcaa gatattgatt ttcataagag agttttaagc aataaatttgt cattatatac    8520 agataatagt ttatttgttg agtattatgt tagagataat tttaaagatt tcataaagaa    8580
aggttttctt gatggttttt gggttgttat gtctggagca tattatttta gacatatagt    8640 gccactttttt tttgttttgt atttaattgt atcttttttct cttttctttg ctactggtga    8700
ttatatatat ttatctttttt tatttttttta ttttcttatt tctatttttgt tttcaattcg    8760 agatgggcga agttttatag gtagagtatt tcttcctttt atattttgt cttatcatat    8820 ttcttatgga tgtggatcgt tattatcttt tttgaaaagg tattttaaat gaaaaatttt    8880
attccttttg cgttacctga aattggcgaa gaagaaattg cagaggtaat tgactcttta    8940
cgttcaggtt ggattacgac aggtcctaag gctaagcaat ttgaacaaga atttttctaat    9000 tacctaggag cgaacgttca atcattagct gttaactctg ctacgtcggg cttacatttg    9060
gctcttgaag ctgttggcgt aaagccggga gaccaagtta ttgtcccatc atatacattc    9120
actgctactg ccgaaattgt caggtacctt ggtgctgatc ctgtaattgt tgatgtagat    9180
cgtaaaacat ttaatatatc agttgatgcc attgagaagg ctattactaa tgaaacaaag    9240
gcgattattc cagtacactt cgctggatta gcttgtgaca tggattcaat cttatcaatt    9300
gctaaaaaat atgacctaaa ggttgtcgag gatgccgctc atgcattttcc tacaacatat    9360 aaaggaagta agataggaac gcttgattca gatgctacgg ttttttagctt ctacgccaat    9420 aaaactatga caaccggtga aggcggaatg gttgtttcaa aaaataaaga tataattgag    9480
cgttgtaagg taatgcgttt acatggaatc agtcgtgacg cttttgaccg gtaccagtct    9540
aaaactcctt cttggttttta tgaggttgta gctccagggt ttaaatacaa tatgcctgat    9600
atctgtgcgg caatcggtat tcatcaactt agaaagatcg atgattttca gaaaaaacgt    9660
caacgaatgg caaaaatttta cgatgatgcg ttaaaagaat tgccacttga attgcctgaa    9720
tggcctacta atgctagtga tattcatgct tggcatctat atcctatccg cttaaaaact    9780
gattcggcta ttaatcgcga tgattttatt aagaagttat cagatcttgg aattggttgt    9840
tctgtccatt ttataccgtt gcataagcaa ccggtttggc gtgatacata taatttgaac    9900
gccagtgact ttccagtttc tgaggagtgt tatttaaatg aaatatctat tcctctttat    9960
actaaaatga cggatcaaga tcagttgttc gttatcaaat cgattagaca attatttatg   10020
taatggtatt ttatattaaa tgaaacgtat ttttgatgtt atcgtggcag gcttaggcct   10080 gcttttttcta tttcctgttt ttatcattgt gtcaatgtta attgttgctg attctaaagg   10140
gggggttttt tttaggcagt atagagttgg gagatttggg aaagattttta ggatacataa   10200
```

```
atttagaacg atgtttatcg attcagaaaa aaaaggacgg ataacagttg gtcaagatgc    10260
tcgggtaacc agagttggat ggtatttacg gaagtacaaa atcgatgagc ttcctcaatt    10320
gatagatgtt ctttctggaa caatgagttt ggttggccca agaccggaag tgagggagtt    10380
tattgatgag tatcctgatg atataaggga aaaagtttta tcggttaggc cagggataac    10440
tgacttagca tctatagaaa tggtagatga aaatgagatt ttgtctagtt atgatgaccc    10500
acgtagggct tatatagata taattcttcc aatcaagcaa agatattatt tagattatgt    10560
tgctaacaat tcagtaaagt atgattgtgt gataatttgg aaaactatta ttaagatttt    10620
gtcgcgataa taaggtagtg taggatgatt gatagaatat tggagctgcc aagaattgtt    10680
aagagaggta tcatcatctg cattgatgta gttatggtga tattctcatt ttggttgtct    10740
tattggttga ggcttgatga gcaaacggct tttcttagtg caccgatgtg gtttgctgca    10800
gctattctta ccatatttac cgtgtttata tttatcagga ttgggcttta tcgggcagtc    10860
ttacggtatg ttagtgcaaa gataatgttg ctaataccag ttggtattct ggcctcaacg    10920
ttatctcttg tcgttatatc atattcgcta tccataatgt tgccgcgcac tgttgtcgga    10980
atttattttt tggttttact tttactgaca tcaggctcta gattgctttt tagaatgata    11040
cttaactatg gagttaaggg tagtgcgcct gttttgattt atggcgctgg tgaatctggc    11100
cgacaattat tgccagcatt aatgcaggca aaagaatatt ttcctgtggc atttgtggat    11160
gataatcctc gcttgcataa ggctgtcatt catggtgtaa cagtttatcc ctcggataaa    11220
ctgagttacc ttgtagatcg ctatggtata aagaaaattc ttttggcgat gccgagcgtc    11280
agtaagtcac aaaggcagaa agtgattact cgtttagagc atctaccgtg tgaagttctc    11340
tctattccgg gtatggtcga tttagtcgaa ggtcgagcac aaatcagtaa tctaaaaaaa    11400
gtatcgattg atgacttact aggtcgtgat ccggttgctc ctgatgccaa attgatggcc    11460
gaaaacatta ctggcaaagc cgttatggtc actggggcgg gaggctcgat cggctctgag    11520
cttttgtcgtc aaattgttcg atataagccg gccaaattgg ttctatttga actgtctgaa    11580
tatgccctct acgctattga gaaagagctc tcggcgctgt gcgacaaaga agttttgaat    11640
gttccagtga tccctctgtt gggctcggtg cagcgtcaga atcgcttaca gatggtgatg    11700
aagtcctttg gtattcaaac ggtttatcat gcggccgctt ataaacatgt gcctctggtt    11760
gagcataatg tggtggaagg ggtacgtaat aacgtgtttg gtaccttgta ctgcgctgag    11820
tcagcgatcg aaagtggcgt tgaaactttt gtgttgattt ccaccgataa agcggtgcgc    11880
ccgaccaaca ctatggggac aactaagcgt ctggccgaat tggtattgca ggctttgtct    11940
gcacggcaaa gccaaactcg cttttgtatg gtgcgatttg gtaatgtact cggttcttcg    12000
ggctctgtcg tgccgttgtt tgaaaaacag attgcccaag gtgggccagt taccttgact    12060
catcgtgaca ttattcgcta tttcatgaca attccggaag catcacagtt ggtgattcaa    12120
gcgggggcga tggggcatgg cggcgatgtc tttgtcttag acatgggcga tccggtcaag    12180
atttatgact tagccaaacg catgatccgg ttaagtggct tgagtgtacg ggatgataaa    12240
aatccagatg gcgatattgc cattgaagtt acgggattac gtccaggga gaaactgtat    12300
gaagaattac tgattggtga ttcagttcaa ggtacctctc atccacgaat tatgacggcc    12360
aacgaagtga tgctaccgtg gcaggatcta tcgctcttac ttaaagagct ggatcaagct    12420
tgtcatgact ttgatcatga gcgaattcgc agtttgttgt tacaagcacc agcggcattc    12480
aatccaactg atgatatttg cgatctagtt tggcagcaga aaaaatcgct gttatcacaa    12540
gcgagcaatg tcattcgcct gtgattgctt aggtttaacc ttccacacca attcttcacc    12600
```

-continued

```
tctcttacaa atccccgcta ggcggtacat cgtgaccgcc tttagcctga tgcctgctct      12660
ttaacaaaca ggacatcagt gtatgtttaa acctttttagc gccgaatttt tcggcacttt     12720
ctggctggtt ctgggtggct gtggtagcgc cttgatctct gctgctttcc cacagttagg      12780
tataggcttt ttgggcgtgg cgttggcgtt tggtctgaca gtagtcacca tggcttatgc      12840
ggtcgggcac atctctggtg cgcattttaa ccccgcggtg accttgggtc tgtgggccgg      12900
tggacgcttc ccagcagcgc gcgtgttacc ttacattatc gctcaggtta tcggcggtat      12960
tgccgctgcg gcagtgctgt atggtatcgc cagcggtaag gctgggtttg atgcgacaac      13020
cagcggtttt gcggctaatg gttatggcct ccattcacct ggcggctatg cgttaagcgc      13080
ctgtatgctg agcgagtttg tcctcagtgc gttttttgtc cggagcgaca gaaaaacgcg      13140
ctcctgcggg ctttgcgcca ctggcgattg gtctggtaat caccccgtaa attaaccagc      13200
gtcaaaagta gaattttctc gtaccataaa cgcaggagat tctttatgca aacatcaaaa      13260
tttaccgaca agcaaatcat ggcgatcctc aaatgaaccc ccccggg                    13307
```

<210> SEQ ID NO 4
<211> LENGTH: 12692
<212> TYPE: DNA
<213> ORGANISM: Shigella sonnei
<220> FEATURE:
<223> OTHER INFORMATION: 12.7 kb HindIII-PmeI fragment from AF294823
      (SEQ ID NO:7 positions 1310-14001) encoding Shigella sonnei O
      antigen gene cluster

<400> SEQUENCE: 4

```
aagcttgatc aaatagctca tattcagcga gatttaacaa ctgcggaaca agccggaatc        60
attgattatc gctctagcaa aggcggcttc gataatgcgc aaagtagcta taagttcttg       120
ctcggcgaaa aactgttatc agcagagcta aaagcaacta agatgcgcc aattatttac        180 ccatttagat attacgaagt gaaacgtcaa attgatgagt tagaaggaat gttacgcgat       240
aacattcagg cgcaagcata tcgatatcaa atgaagccat ctgagccagt tataaaagac       300
aaacccaaca agcattaat tttgattctt ggtgcattac caggggcaat gtttgctata       360
gttggtacat tagtttatgc gacattaaaa gataaaacca agttagatta aactgggtta       420
cgtattgttg tgtcaatgcg aaatagatgt tctatgtgca ctttatgatg gataagaaaa       480
tgaaattcga tactttgaat gcgaaaattg ggattatagg ccttggttat gttggattgc       540
ctcttgctgt tgagtttgga aagaaagtaa cgacgattgg atttgatatt aataagtctc       600
gtattgatga attacgaaat ggtcacgata gtacattaga gtgctcaaat ttagagttgt       660
tagaagcaac taaattgacg tacgcctgtt cattagatgc actaaaagag tgtaatgtat       720
ttattgtaac tgttccaact ccaattgata aacataaaca gccagatcta acacctctaa       780
ttaaagcatc tgaaacattg ggtaagataa taagaaagg cgatgttatt atttatgagt       840
caacagttta ccctggagcg acagaagaag attgtatacc agttgtagag aaagtatcag       900
gtcttaagtt taatattgat ttttttgccg ttattcacc tgagcgtatt aatcctgggg       960
ataaagagca tcgtgtaact aatatccta aggtgaccag tggatctaca ccggatgttg      1020
ctgagtatgt agatcagcta tataaattaa taattactgt cggtacgcat aaagcatcat      1080
cgataaaagt agcagaggct gcaaagtaa ttgaaaacac gcagcgagat gtcaatattg      1140
cattgattaa tgagttatct attatattta ataagttagg gattgatacc ttagaggttc      1200
ttgaggctgc aggtacgaag tggaattttt tacctttttag gcccggttta gtaggtggcc      1260
actgtatagg tgtagatcct tattatctta cacataaagc gcaaagtgtc ggctatcatc      1320
```

```
cggagatgat tttagccgga cgtcgtttaa atgatagtat ggggcagtat gtcgtttccc    1380
agttagtcaa aaaaatgttg aaacaacgga ttcaagttga agggggcgaat gtgttagtga    1440
tggggcttac atttaaagag aattgcccag atctacgaaa cactaaagtg attgatatta    1500
tttcagagtt aaaagaatac aatatcaata tagatattat agatccatgg tgttctaccg    1560
atgaggcaca acatgaatat ggattaactt tatgtgaaga tcctaaagtt aatcattatg    1620
atgcaataat tatcgctgtt gcacacaatg agtttcgcga gatgggagag agcgctattc    1680
gtgcattagg taaagacgag cacgttttgt tcgatttaaa atatgtgctt gataaaaaaa    1740
gtatcgatat gcgcttgtaa gagtgattaa aaaaatcaaa tcctctttga tatgatacac    1800
ctcagcattt tatgctaggt ttagcacttg attaatatac atggatattt atatgtctcg    1860
ctatgaagag attacacagc agttaatttt ttcaccgaaa acttggttaa ttactggtgt    1920
cgctggcttt ataggatcaa atcttttaga aaagttactt aaattaaacc aggttgttat    1980
tgggttagat aacttttcca cgggacatca atataatctt gatgaagtta aaacattagt    2040
ttccactgaa cagtggagtc gattttgctt tatagaaggt gatattcgag atctcactac    2100
ctgtgagcaa gttatgaaag gtgttgatca tgtcttacat caggctgcgc taggttctgt    2160
acctcgttca attgttgatc ctataacaac caatgcaact aatattactg gattttgaa    2220
tatcttacat gcggctaaaa atgcacaagt acaaagtttt acttatgctg catcaagctc    2280
aacttatgga gatcatcccg cactaccaaa agtagaggaa acattggta atccactttc    2340
tccttatgca gttactaaat atgttaacga gatttatgct caggtatatg ctcgaacata    2400
tggttttaaa actattggat tacgttattt taatgtattt ggtcgtcgtc aagatcctaa    2460
tggagcttat gctgcagtaa ttccaaaatg gacagcagca atgcttaaag gtgatgacgt    2520
atatattaat ggcgatggtg aaacgagtcg tgattttttgt tatatagata atgttataca    2580
aatgaatata ttatctgcat tagcgaagga cagtgctaaa gataatatat ataatgttgc    2640
agttggtgat agaacaacgt taaatgaatt atctggttac atttatgatg agcttaattt    2700
aattcaccat atcgataaat tgagcattaa gtatagagag tttagatctg gagatgttag    2760
gcattctcag gctgatgtta ctaaggctat agatttacta agtatagac caaatataaa    2820
aatcagagag ggattacgac tttcaatgcc gtggtatgtg agattttaa aaggctaaat    2880
tatattaaca tgaataaata atctatttca cctctgttat taatgcaggg gtgaaaatcc    2940
atgtatttat tctaaatggt cagtgtatgt ttagaaaaat gattgatgca ggtggtacat    3000
ttttacttaa agcaatattt caaataggag ttttttgttta tttcacacat gtgtcagata    3060
ttactacatt tggtattatt agttatgtgt ttactgtttat ttggttttgt g cttaacttct    3120
ctgattatgg atttagaaca aaattagtga aagatatttc tgataatagt tattctgcat    3180
cagaattatt atcaagaagt gatggagtta aaacatatgt tttttcttc atttttataa    3240
tcttcatgtt ttattcttat gtttctgatt caatttcatt aactctgctt gtttatattt    3300
catctgcata ttttgtttgt atttcaagtg gtagatttag cttgctacag gctgttggtc    3360
ggtttagatg tgaattatat ataaatatct actcaacaat tatatatatt gggtgtaatt    3420
tatttttatc tctgtttatc gaacctctat attatagtgc gatatcaata ttcatatact    3480
caatttcgct tttggttttc tcatcacata atgcaatgt gccatgtttt catataaaaa    3540
gaccaagtat tttagtttat aaagattttt tggatgcaac tccgttcgct attctggtgt    3600
tactaaatgt tgttttatct agtattgacc tttttatatt aaaagaatat ttctcttata    3660
atagtgttgc tatatatcag gtggtaacta gggttaatac cggtctaata atagtgttta    3720
```

```
atgttatttta tactgttttta ttgccttcat tttcttatta tctgaaaaat tctgaatggg    3780
gtaatataag gaaattacaa cgatatatat cactgttagt cttattacta tgtttatgct    3840
attatttttt tggcatctat ttcgtaggga tattgtttgg tgatgagtat aaggtaatat    3900
cttctgcaac attttttgata atgtttatgg ctcttattaa atataatttt tggctaataa    3960 atgaactttta tcttgtgtgt agtggaaatc aaagcgagcg agttaaatcg tattgtattg    4020
gtgtggtcat ttcaatggcg gttttctttt attttatacc tcggtatgga tggagtgggg    4080 cggttttttgg aagtgccatt gcaacattag taattggaat attttatatt atttctgtga    4140
aaaaagattg tgggaaaatt cttcatgata agtattcact aatgatgatc tttgtcccaa    4200
ttttctttta ttttattatt aatggtcagc agcggttgtt atattaatat gttgtggttt    4260
tatatcgttc cattaatatg tttagactcg attggaagcc taataaaggt taagtatgtt    4320
aatataccta tatcctgtac ttttgttatt taatatcctt ccggtttttt tttatggaca    4380
aatgaactct gatttagagc gttttttttgg agttcctatt ggctatattc cagatctaat    4440
attttatttc tttgttgttt taacatctat aataacgttg aggtttcacg tttctctgtg    4500
gacaaagaaa ttattatttt taggcatcat attcctgatt tatatcagca ttcagatgtt    4560
gttgttatca gcggatatat caggtgtcgt aattttatta tcgttttttt ctaattttat    4620
agctttggtt cttttggtgt cattttgcat tggtaaagat gagctttatt taactcattc    4680
ggttagaaat ataaatgttg taatgtgttt tggtattatc tgtggagttg taaaattatt    4740
tattggttat tctgaagata gtaattttat agtttattta aatagaaatg ccaccgcaat    4800
tatagtagtg tgcttttatt gtgtatattc atactttttat cgtggtcgaa agtcttggta    4860
tgtctcatct gtattgtact ctctgttctt tcttttttctg gatagccgag caggaataat    4920
atcatttgct atatcgttgt ttttttgtttt tcttcagtta acaaagaagg aaaagttatt    4980
aatatcattg ttttttgttc ctcttctaac tttaggtatt tcttttactg atataggcac    5040
tcgtcttgaa cgaatgctgt cttcgtcaca ggttatattc tctggtggta acactcttac    5100
aaaaagtcag aatgattatc gtcgagttga gttagtattt attggggttg atgttttaaa    5160
agaaaattat ttaattggca ctggattagg tgttgcaaat tatgtaaagg ctatagataa    5220
aaagttttta ggaagtacca actttgggtt ggcgcataat ttttattttat cttattcggc    5280 tcagttaggg attattggtt ttattttgct tatttctgta tttatataaa tgctgtctcc    5340 aattttttaaa tgcggagggt atattggtaa aggatgcgtt tttgctttgg ctttctatgt    5400
cttttttaat gagtatatat tgacgccagc gatatatatt tatatttcta tttttttatc    5460
ggtggttttt atacgtaatt ctaaatagct gcgcggaata gtagatcact ttgagggaac    5520
ttagcccgga ttgtgcgatc tgatcaatcg ccaaatcaaa acaaatcacc aaccggactg    5580
agcaatgccg atcatagcac caatttcccg tgacgaacga cgcctgatgc agaaagccat    5640
ccataaaaca cacgataaaa attatgcccg cagactgact gccatgctga tgctgcaccg    5700
gggcgaccgt gtcagcgacg ttgccagaac gctctgctgc gcccgttcct ctgttggacg    5760
ctggattaac tggttcacgc agtcgggtgt tgagggactg aaatcattac ctgccggggcg    5820 tgcccgtcgc tggccgtttg agcatatctg cacactgtta cgtgagctgg taaaacattc    5880
tcccggcgac tttggctacc agcgttcacg ctggagtaca gaactgctgg caataaaaat    5940
caatgagata accggttgcc agttaaatgc cggaaccgtt cgccgctggt tgccgtctgc    6000
ggggattgtg tggcgaaggg ctgcgccaac tctgcgtatc cgtgacccgc ataaagatga    6060
aaagatggca gcaatccata aagcactgga cgaatgcagc gcagagcatc cggtctttta    6120
```

```
tgaagatgaa gtggatatcc atcttaatcc caaaatcggt gcggactggc aactgcgcgg    6180
acagcaaaaa cgggtggtca cgccgggaca gaatgaaaaa tattatctgg ccggagcgct    6240
gcacagcggg acaggtaaag tcagctgtgt gggcggcaac agcaaaagtt cggcgctgtt    6300
catcagcctg ctgaagcggc ttaaagcgac ataccgtcgg gcgaaaacca tcacgctgat    6360
cgtggacaac tacattatcc acaaaagccg ggaaacacag agctggctga aggagaaccc    6420
gaagttcagg gtcatttatc agccggttta ctcgccatgg atgaatcatg ttgaacggct    6480
atggcaggca cttcacgaca caataacgcg taatcatcag tgcagctcaa tgtggcaact    6540
gttgaaaaaa gttcgccatt ttatggaaac cgtcagccca ttccccggag gcaaacatgg    6600
gctggcaaaa gtgtagcggt attaagcgca gctatttagg atgagaatat gttgttagaa    6660
tatgttgaaa gaaaaatttc cttagccttg agtaagtatc ctaaggtaag ggatgttatt    6720
aagttctttt atttatatat cgcatcatta ttcggaatta ttttgaataa aaataagacg    6780
gttattcaat caaaaatata cgagatttca attgatgatt ctgaagaatc attttttggc    6840
tattatgacc atagtccaat gagctctaat gggcggtacg tattgttcca ctctagtgcg    6900
tttagcacta aacgacatcc aaagaaagtt aagtatatat ctatttgcgt aaaagacctt    6960
cttaataaca aagtttataa gctatatgat acgcgagcat ttaattggca gcagggaagc    7020
cgattaatgt ggattgatga tgacaatata attttttaatg actatgaaaa taatggatac    7080
attagtgttg tctattcttt gtctttgatg aaggttataa aaaaaataaa ctatccgatt    7140
tatgatgtga ataattacaa ggctgtgacg ttagatttct catggctggc taaatatgat    7200
agcgattatg gttattataa taaaaaatca ttttctacag atatttcaat cattaatttg    7260
aatacggggg gaatagaatt atttttatcc ttagacgaaa tgctaaagag aactaatttt    7320
aaatgtaata ttgatgttga acatgtggtc aatcattttta tgtttgctcc cgatggacgt    7380
tccgttatgt tcatacatcg atactataca cctaaaggaa agcgtgaaag gttaatacat    7440
tggaatttaa taaatgataa tgttcgagtc ctaataaatg aatcgattat tagtcattgt    7500
tgttggaatg ggaatgatga aattataggt ttttttggtg cagaaataga ttcgctaaat    7560
tattatagat tgtcaattga atcctgtaat acagagaaat tgttttttga tgcaagaaaa    7620
tattctgatg gacatcctac tatagttcat aatagatata ttatatctga tacttaccca    7680
gataaaaata gaattaaaaa gttgtttgtt tatgaccttg tcaaaaatga ttatcgcgag    7740
cttggattat tttatgagtc aatgagtttt ttttcttatt ctcgatgtga cttacatcca    7800
aggatctcgg ttgataatag attttttgttt gttgattcag ttcactcagg gaaaagaaaa    7860 ctatattta tgaggagtgg tatttgtgag tgatgttcta gtatctttaa ttatagtttg    7920
ctttaatgca gagaagtata ttgaaaaaatc tcttttggca tttattaatc aagatgttgg    7980
attagataaa tttgaattga ttattgtaga tggggattca tctgataata caatatctat    8040
tgttcaggat gttttttcta aacatagcaa cattaagcat aaaattatca ataataaaaa    8100
aagaactctt gctacgggtt ggaatattgg ggtgctagaa gctaatggta agtttgtgtg    8160
tagagttgat gcacatagtg atattccaaa taactatata tctaaattat tagatgatta    8220
ttttaatatt atgcagtttg atgatagcgt tgttggtgtt ggaggtgtat taactaattc    8280
ttataaaact aagtttggtt caattgtagc ggattttat gcatcgaaat ttggtgttgg    8340
taattctcca tttaggtgcg tagacaaaaa taatcgacta aaaaaaacag atacagctgt    8400
ctttgcttta tataataaag atgtgttttt tgatgttgga ctttttaatg aagtattaga    8460
tagaaatcaa gatattgatt ttcataagag agttttaagc aataatttgt cattatatac    8520
```

```
agataatagt ttatttgttg agtattatgt tagagataat tttaaagatt tcataaagaa    8580
aggttttctt gatggttttt gggttgttat gtctggagca tattatttta gacatatagt    8640
gccacttttt tttgttttgt atttaattgt atcttttttct cttttctttg ctactggtga    8700
ttatatatat ttatcttttt tatttttttta ttttcttatt tctattttgt tttcaattcg    8760
agatgggcga agtttatag gtagagtatt tcttcctttt atattttgt cttatcatat      8820
ttcttatgga tgtggatcgt tattatcttt tttgaaaagg tattttaaat gaaaaatttt    8880
attcctttg cgttacctga aattggcgaa gagaaattg cagaggtaat tgactcttta     8940
cgttcaggtt ggattacgac aggtcctaag gctaagcaat tgaacaaga atttctaat     9000
tacctaggag cgaacgttca atcattagct gttaactctg ctacgtcggg cttacatttg    9060
gctcttgaag ctgttggcgt aaagccggga gaccaagtta ttgtcccatc atatacattc    9120
actgctactg ccgaaattgt caggtacctt ggtgctgatc ctgtaattgt tgatgtagat   9180
cgtaaaacat ttaatatatc agttgatgcc attgagaagg ctattactaa tgaaacaaag    9240
gcgattattc cagtacactt cgctggatta gcttgtgaca tggattcaat cttatcaatt    9300
gctaaaaaat atgacctaaa ggttgtcgag gatgccgctc atgcatttcc tacaacatat    9360
aaaggaagta agataggaac gcttgattca gatgctacgg ttttttagctt ctacgccaat    9420
aaaactatga caaccggtga aggcggaatg gttgtttcaa aaaataaaga tataattgag    9480
cgttgtaagg taatgcgttt acatggaatc agtcgtgacg cttttgaccg gtaccagtct    9540
aaaactcctt cttggttta tgaggttgta gctccagggt ttaaatacaa tatgcctgat    9600
atctgtgcgg caatcggtat tcatcaactt agaaagatcg atgattttca gaaaaaacgt    9660
caacgaatgg caaaaattta cgatgatgcg ttaaaagaat tgccacttga attgcctgaa    9720
tggcctacta atgctagtga tattcatgct tggcatctat atcctatccg cttaaaaact    9780
gattcggcta ttaatcgcga tgattttatt aagaagttat cagatcttgg aattggttgt    9840
tctgtccatt ttataccgtt gcataagcaa ccggtttggc gtgatacata taatttgaac    9900
gccagtgact ttccagtttc tgaggagtgt tatttaaatg aaatatctat tcctcttttat    9960
actaaaatga cggatcaaga tcagttgttc gttatcaaat cgattagaca attatttatg   10020
taatggtatt ttatattaaa tgaaacgtat ttttgatgtt atcgtggcag gcttaggcct   10080
gcttttttcta tttcctgttt ttatcattgt gtcaatgtta attgttgctg attctaaagg   10140
gggggttttt tttaggcagt atagagttgg gagatttggg aaagatttta ggatacataa   10200
atttagaacg atgtttatcg attcagaaaa aaaaggacgg ataacagttg gtcaagatgc   10260
tcgggtaacc agagttggat ggtatttacg gaagtacaaa atcgatgagc ttcctcaatt   10320
gatagatgtt ctttctggaa caatgagttt ggttggccca agaccggaag tgaggagtt    10380
tattgatgag tatcctgatg atataaggga aaagttttta tcggttaggc cagggataac   10440
tgacttagca tctatagaaa tggtagatga aaatgagatt ttgtctagtt atgatgcccc   10500
acgtagggct tatatagata taattcttcc aatcaagcaa agatattatt tagattatgt   10560
tgctaacaat tcagtaaagt atgattgtgt gataatttgg aaaactatta ttaagatttt   10620
gtcgcgataa taaggtagtg taggatgatt gatagaatat tggagctgcc aagaattgtt   10680
aagagaggta tcatcatctg cattgatgta gttatggtga tattctcatt ttggttgtct   10740
tattggttga ggcttgatga gcaaacggct tttcttagtg caccgatgtg gtttgctgca   10800
gctattctta ccatatttac cgtgttttata tttatcagga ttgggcttta tcgggcagtc   10860
ttacggtatg ttagtgcaaa gataatgttg ctaataccag ttggtattct ggcctcaacg   10920
```

-continued

```
ttatctcttg tcgttatatc atattcgcta tccataatgt tgccgcgcac tgttgtcgga    10980
atttatttt tggttttact tttactgaca tcaggctcta gattgctttt tagaatgata    11040
cttaactatg gagttaaggg tagtgcgcct gttttgattt atggcgctgg tgaatctggc    11100
cgacaattat tgccagcatt aatgcaggca aaagaatatt ttcctgtggc atttgtggat    11160
gataatcctc gcttgcataa ggctgtcatt catggtgtaa cagtttatcc ctcggataaa    11220
ctgagttacc ttgtagatcg ctatggtata aagaaaattc ttttggcgat gccgagcgtc    11280
agtaagtcac aaaggcagaa agtgattact cgtttagagc atctaccgtg tgaagttctc    11340
tctattccgg gtatggtcga tttagtcgaa ggtcgacac aaatcagtaa tctaaaaaaa    11400
gtatcgattg atgacttact aggtcgtgat ccggttgctc ctgatgccaa attgatggcc    11460
gaaaacatta ctggcaaagc cgttatggtc actggggcgg gaggctcgat cggctctgag    11520
ctttgtcgtc aaattgttcg atataagccg gccaaattgg ttctatttga actgtctgaa    11580
tatgccctct acgctattga gaaagagctc tcggcgctgt gcgacaaaga agttttgaat    11640
gttccagtga tccctctgtt gggctcggtg cagcgtcaga atcgcttaca gatggtgatg    11700
aagtcctttg gtattcaaac ggtttatcat gcggccgctt ataaacatgt gcctctggtt    11760
gagcataatg tggtggaagg ggtacgtaat aacgtgtttg gtaccttgta ctgcgctgag    11820
tcagcgatcg aaagtggcgt tgaaactttt gtgttgattt ccaccgataa agcggtgcgc    11880
ccgaccaaca ctatggggac aactaagcgt ctggccgaat tggtattgca ggctttgtct    11940
gcacggcaaa gccaaactcg cttttgtatg gtgcgatttg gtaatgtact cggttcttcg    12000
ggctctgtcg tgccgttgtt tgaaaaacag attgcccaag gtgggccagt taccttgact    12060
catcgtgaca ttattcgcta tttcatgaca attccggaag catcacagtt ggtgattcaa    12120
gcggggcga tggggcatgg cggcgatgtc tttgtcttag acatgggcga tccggtcaag    12180
atttatgact tagccaaacg catgatccgg ttaagtggct tgagtgtacg ggatgataaa    12240
aatccagatg gcgatattgc cattgaagtt acgggattac gtccagggga gaaactgtat    12300
gaagaattac tgattggtga ttcagttcaa ggtacctctc atccacgaat tatgacggcc    12360
aacgaagtga tgctaccgtg gcaggatcta tcgctcttac ttaaagagct ggatcaagct    12420
tgtcatgact ttgatcatga gcgaattcgc agtttgttgt tacaagcacc agcggcattc    12480
aatccaactg atgatatttg cgatctagtt tggcagcaga aaaaatcgct gttatcacaa    12540
gcgagcaatg tcattcgcct gtgattgctt aggtttaacc ttccacacca attcttcacc    12600
tctcttacaa atccccgcta ggcggtacat cgtgaccgcc tttagcctga tgcctgctct    12660
ttaacaaaca ggacatcagt gtatgtttaa ac                                  12692
```

<210> SEQ ID NO 5
<211> LENGTH: 12421
<212> TYPE: DNA
<213> ORGANISM: Shigella sonnei
<220> FEATURE:
<223> OTHER INFORMATION: 12.4 HindIII fragment from AF294823 (SEQ ID
     NO:7 positions 1310-13730) encoding a portion of the Shigella
     sonnei O antigen gene cluster.

<400> SEQUENCE: 5

```
aagcttgatc aaatagctca tattcagcga gatttaacaa ctgcggaaca agccggaatc      60
attgattatc gctctagcaa aggcggcttc gataatgcgc aaagtagcta taagttcttg     120
ctcggcgaaa aactgttatc agcagagcta aaagcaacta agatgcgcc aattatttac     180
ccatttagat attacgaagt gaaacgtcaa attgatgagt tagaaggaat gttacgcgat     240
```

```
aacattcagg cgcaagcata tcgatatcaa atgaagccat ctgagccagt tataaaagac    300
aaacccaaca aagcattaat tttgattctt ggtgcattac caggggcaat gtttgctata    360
gttggtacat tagtttatgc gacattaaaa gataaaacca agttagatta aactgggtta    420
cgtattgttg tgtcaatgcg aaatagatgt tctatgtgca ctttatgatg gataagaaaa    480
tgaaattcga tactttgaat gcgaaaattg ggattatagg ccttggttat gttggattgc    540
ctcttgctgt tgagtttgga aagaaagtaa cgacgattgg atttgatatt aataagtctc    600
gtattgatga attacgaaat ggtcacgata gtacattaga gtgctcaaat ttagagttgt    660
tagaagcaac taaattgacg tacgcctgtt cattagatgc actaaaagag tgtaatgtat    720
ttattgtaac tgttccaact ccaattgata aacataaaca gccagatcta acacctctaa    780
ttaaagcatc tgaaacattg ggtaagataa taaagaaagg cgatgttatt atttatgagt    840
caacagttta ccctggagcg acagaagaag attgtatacc agttgtagag aaagtatcag    900
gtcttaagtt taatattgat ttttttgccg gttattcacc tgagcgtatt aatcctgggg    960
ataaagagca tcgtgtaact aatatcctta aggtgaccag tggatctaca ccggatgttg   1020
ctgagtatgt agatcagcta tataaattaa taattactgt cggtacgcat aaagcatcat   1080
cgataaaagt agcagaggct gcaaaagtaa ttgaaaacac gcagcgagat gtcaatattg   1140
cattgattaa tgagttatct attatattta ataagttagg gattgatacc ttagaggttc   1200
ttgaggctgc aggtacgaag tggaattttt tacctttag gcccggttta gtaggtggcc    1260
actgtatagg tgtagatcct tattatctta cacataaagc gcaaagtgtc ggctatcatc   1320
cggagatgat tttagccgga cgtcgtttaa atgatagtat ggggcagtat gtcgtttccc   1380
agttagtcaa aaaaatgttg aaacaacgga ttcaagttga aggggcgaat gtgttagtga   1440
tggggcttac atttaaagag aattgcccag atctacgaaa cactaaagtg attgatatta   1500
tttcagagtt aaaagaatac aatatcaata tagatattat agatccatgg tgttctaccg   1560
atgaggcaca acatgaatat ggattaactt tatgtgaaga tcctaaagtt aatcattatg   1620
atgcaataat tatcgctgtt gcacacaatg agtttcgcga gatgggagag agcgctattc   1680
gtgcattagg taaagacgag cacgttttgt tcgatttaaa atatgtgctt gataaaaaaa   1740
gtatcgatat gcgcttgtaa gagtgattaa aaaaatcaaa tcctctttga tatgatacac   1800
ctcagcattt tatgctaggt ttagcacttg attaatatac atggatattt atatgtctcg   1860
ctatgaagag attacacagc agttaatttt ttcaccgaaa acttggttaa ttactggtgt   1920
cgctggcttt ataggatcaa atcttttaga aaagttactt aaattaaacc aggttgttat   1980
tgggttagat aacttttcca cgggacatca atataatctt gatgaagtta aaacattagt   2040
ttccactgaa cagtggagtc gattttgctt tatagaaggt gatattcgag atctcactac   2100
ctgtgagcaa ttatgaaag gtgttgatca tgtcttacat caggctgcgc taggttctgt    2160
acctcgttca attgttgatc ctataacaac caatgcaact aatattactg gattttgaa    2220 tatcttacat gcggctaaaa atgcacaagt acaaagtttt acttatgctg catcaagctc   2280
aacttatgga gatcatcccg cactaccaaa agtagaggaa acattggta atccactttc    2340 tccttatgca gttactaaat atgttaacga gatttatgct caggtatatg ctcgaacata   2400
tggttttaaa actattggat tacgttattt taatgtattt ggtcgtcgtc aagatcctaa   2460
tggagcttat gctgcagtaa ttccaaaatg gacagcagca atgcttaaag gtgatgacgt   2520
atatattaat ggcgatggtg aaacgagtcg tgattttgt tatatagata atgttataca    2580
aatgaatata ttatctgcat tagcgaagga cagtgctaaa gataatatat ataatgttgc   2640
```

```
agttggtgat agaacaacgt taaatgaatt atctggttac atttatgatg agcttaattt    2700
aattcaccat atcgataaat tgagcattaa gtatagagag tttagatctg gagatgttag    2760
gcattctcag gctgatgtta ctaaggctat agatttacta agtatagac caaatataaa    2820 aatcagagag ggattacgac tttcaatgcc gtggtatgtg agatttttaa aaggctaaat    2880
tatattaaca tgaataaata atctatttca cctctgttat taatgcaggg gtgaaaatcc    2940
atgtatttat tctaaatggt cagtgtatgt ttagaaaaat gattgatgca ggtggtacat    3000
ttttacttaa agcaatattt caaataggag ttttttgttta tttcacacat gtgtcagata    3060
ttactacatt tggtattatt agttatgtgt ttactgttta ttggtttgtg cttaacttct    3120
ctgattatgg atttagaaca aaattagtga agatatttc tgataatagt tattctgcat    3180
cagaattatt atcaagaagt gatggagtta aaacatatg tttttttcttc attttttataa   3240 tcttcatgtt ttattcttat gtttctgatt caatttcatt aactctgctt gtttatattt    3300
catctgcata ttttgtttgt atttcaagtg gtagatttag cttgctacag gctgttggtc    3360
ggtttagatg tgaattatat ataaatatct actcaacaat tatatatatt gggtgtaatt    3420 tattttttatc tctgtttatc gaacctctat attatagtgc gatatcaata ttcatatact   3480
caatttcgct tttggttttc tcatcacata aatgcaatgt gccatgtttt catataaaaa    3540
gaccaagtat tttagtttat aaagatttt tggatgcaac tccgttcgct attctggtgt    3600
tactaaatgt tgttttatct agtattgacc ttttttatatt aaaagaatat ttctcttata   3660
atagtgttgc tatatatcag gtggtaacta gggttaatac cggtctaata atagtgttta   3720 atgttatttta tactgttttta ttgccttcat tttcttatta tctgaaaaat tctgaatggg   3780
gtaatataag gaaattacaa cgatatatat cactgttagt cttattacta tgtttatgct    3840
attatttttt tggcatctat ttcgtaggga tattgtttgg tgatgagtat aaggtaatat    3900
cttctgcaac ttttttgata atgtttatgg ctcttattaa atataatttt tggctaataa    3960
atgaacttta tcttgtgtgt agtggaaatc aaagcgagcg agttaaatcg tattgtattg    4020
gtgtggtcat ttcaatggcg gttttctttt attttataccc tcggtatgga tggagtgggg   4080 cggttttttgg aagtgccatt gcaacattag taattggaat attttatatt atttctgtga   4140
aaaaagattg tgggaaaatt cttcatgata agtattcact aatgatgatc tttgtcccaa    4200 ttttcttttta ttttattatt aatggtcagc agcggttgtt atattaatat gttgtggttt    4260
tatatcgttc cattaatatg tttagactcg attggaagcc taataaaggt taagtatgtt    4320
aatataccta tatcctgtac ttttgttatt taatatcctt ccggtttttt tttatggaca    4380
aatgaactct gatttagagc gttttttttgg agttcctatt ggctatattc cagatctaat   4440
attttatttc tttgttgttt taacatctat aataacgttg aggtttcacg tttctctgtg    4500
gacaaagaaa ttattatttt taggcatcat attcctgatt tatatcagca ttcagatgtt    4560
gttgttatca gcggatatat caggtgtcgt aatttttatta tcgttttttt ctaatttttat   4620 agctttggtt cttttggtgt cattttgcat tggtaaagat gagctttatt taactcattc    4680
ggttagaaat ataaatgttg taatgtgttt tggtattatc tgtggagttg taaaattatt    4740
tattggttat tctgaagata gtaatttat agtttattta aatagaaatg ccaccgcaat    4800
tatagtagtg tgcttttatt gtgtatattc atactttat cgtggtcgaa agtcttggta     4860
tgtctcatct gtattgtact ctctgttctt tcttttttctg gatagccgag caggaataat    4920
atcatttgct atatcgttgt ttttttgtttt tcttcagtta acaaagaagg aaaagttatt    4980
aatatcattg ttttttgttc ctcttctaac tttaggtatt tcttttactg ataraggcac     5040
```

```
tcgtcttgaa cgaatgctgt cttcgtcaca ggttatattc tctggtggta acactcttac   5100
aaaaagtcag aatgattatc gtcgagttga gttagtattt attggggttg atgttttaaa   5160
agaaaattat ttaattggca ctggattagg tgttgcaaat tatgtaaagg ctatagataa   5220
aaagttttta ggaagtacca actttgggtt ggcgcataat ttttatttat cttattcggc   5280
tcagttaggg attattggtt ttattttgct tatttctgta ttttatataa tgctgtctcc   5340
aatttttaaa tgcggagggt atattggtaa aggatgcgtt tttgctttgg ctttctatgt   5400
cttttttaat gagtatatat tgacgccagc gatatatatt tatatttcta tttttttatc   5460
ggtggttttt atacgtaatt ctaaatagct gcgcggaata gtagatcact ttgagggaac   5520
ttagcccgga ttgtgcgatc tgatcaatcg ccaaatcaaa acaaatcacc aaccggactg   5580
agcaatgccg atcatagcac caatttcccg tgacgaacga cgcctgatgc agaaagccat   5640
ccataaaaca cacgataaaa attatgcccg cagactgact gccatgctga tgctgcaccg   5700
gggcgaccgt gtcagcgacg ttgccagaac gctctgctgc gcccgttcct ctgttggacg   5760
ctggattaac tggttcacgc agtcgggtgt tgagggactg aaatcattac ctgccgggcg   5820
tgcccgtcgc tggccgtttg agcatatctg cacactgtta cgtgagctgg taaaacattc   5880
tcccggcgac tttggctacc agcgttcacg ctggagtaca gaactgctgg caataaaaat   5940
caatgagata accggttgcc agttaaatgc cggaaccgtt cgccgctggt tgccgtctgc   6000
ggggattgtg tggcgaaggg ctgcgccaac tctgcgtatc cgtgacccgc ataaagatga   6060
aaagatggca gcaatccata aagcactgga cgaatgcagc gcagagcatc cggtctttta   6120
tgaagatgaa gtggatatcc atcttaatcc caaaatcggt gcggactggc aactgcgcgg   6180
acagcaaaaa cgggtggtca cgccgggaca gaatgaaaaa tattatctgg ccggagcgct   6240
gcacagcggg acaggtaaag tcagctgtgt gggcggcaac agcaaaagtt cggcgctgtt   6300
catcagcctg ctgaagcggc ttaaagcgac ataccgtcgg gcgaaaacca tcacgctgat   6360
cgtggacaac tacattatcc acaaaagccg ggaaacacag agctggctga aggagaaccc   6420
gaagttcagg gtcatttatc agccggttta ctcgccatgg atgaatcatg ttgaacggct   6480
atggcaggca cttcacgaca caataacgcg taatcatcag tgcagctcaa tgtggcaact   6540
gttgaaaaaa gttcgccatt ttatggaaac cgtcagccca ttccccggag gcaaacatgg   6600
gctggcaaaa gtgtagcggt attaagcgca gctatttagg atgagaatat gttgttagaa   6660
tatgttgaaa gaaaaatttc cttagccttg agtaagtatc ctaaggtaag ggatgttatt   6720
aagttctttt atttatatat cgcatcatta ttcggaatta ttttgaataa aaataagacg   6780
gttattcaat caaaaatata cgagatttca attgatgatt ctgaagaatc atttttttggc   6840 tattatgacc atagtccaat gagctctaat gggcggtacg tattgttcca ctctagtgcg   6900
tttagcacta acgacatcc aaagaaagtt aagtatatat ctatttgcgt aaaagacctt   6960
cttaataaca aagtttataa gctatatgat acgcgagcat ttaattggca gcagggaagc   7020
cgattaatgt ggattgatga tgacaatata atttttaatg actatgaaaa taatggatac   7080
attagtgttg tctattcttt gtctttgatg aaggttataa aaaaaataaa ctatccgatt   7140
tatgatgtga ataattacaa ggctgtgacg ttagatttct catggctggc taaatatgat   7200
agcgattatg gttattataa taaaaaatca ttttctacag atatttcaat cattaatttg   7260
aatacggggg gaatagaatt attttttatcc ttagacgaaa tgctaaagag aactaatttt   7320
aaatgtaata ttgatgttga acatgtggtc aatcattta tgtttgctcc cgatggacgt   7380
tccgttatgt tcatacatcg atactataca cctaaaggaa agcgtgaaag gttaatacat   7440
```

```
tggaatttaa taaatgataa tgttcgagtc ctaataaatg aatcgattat tagtcattgt  7500
tgttggaatg ggaatgatga aattataggt tttttttggtg cagaaataga ttcgctaaat  7560
tattatagat tgtcaattga atcctgtaat acagagaaat tgttttttga tgcaagaaaa  7620
tattctgatg gacatcctac tatagttcat aatagatata ttatatctga tacttaccca  7680
gataaaaata gaattaaaaa gttgtttgtt tatgaccttg tcaaaaatga ttatcgcgag  7740
cttggattat tttatgagtc aatgagtttt ttttcttatt ctcgatgtga cttacatcca  7800
aggatctcgg ttgataatag attttttgttt gttgattcag ttcactcagg gaaaagaaaa  7860 ctatattta tgaggagtgg tatttgtgag tgatgttcta gtatctttaa ttatagtttg  7920
ctttaatgca gagaagtata ttgaaaaatc tcttttggca tttattaatc aagatgttgg  7980
attagataaa tttgaattga ttattgtaga tggggattca tctgataata caatatctat  8040
tgttcaggat gtttttttcta aacatagcaa cattaagcat aaaattatca ataataaaaa  8100
aagaactctt gctacgggtt ggaatattgg ggtgctagaa gctaatggta agtttgtgtg  8160
tagagttgat gcacatagtg atattccaaa taactatata tctaaattat tagatgatta  8220
ttttaatatt atgcagtttg atgatagcgt tgttggtgtt ggaggtgtat taactaattc  8280
ttataaaact aagtttggtt caattgtagc ggattttttat gcatcgaaat ttggtgttgg  8340
taattctcca tttaggtgcg tagacaaaaa taatcgacta aaaaaaacag atacagctgt  8400
ctttgcttta tataataaag atgtgttttt tgatgttgga ctttttaatg aagtattaga  8460
tagaaatcaa gatattgatt ttcataagag agttttaagc aataaatttgt cattatatac  8520 agataatagt ttatttgttg agtattatgt tagagataat tttaaagatt tcataaagaa  8580
aggttttctt gatggttttt gggttgttat gtctggagca tattatttta gacatatagt  8640 gccactttt tttgttttgt atttaattgt atcttttttct cttttctttg ctactggtga  8700
ttatatatat ttatcttttt tatttttta ttttcttatt tctatttgt tttcaattcg  8760 agatgggcga agttttatag gtagagtatt tcttccttt atatttttgt cttatcatat  8820
ttcttatgga tgtggatcgt tattatcttt tttgaaaagg tattttaaat gaaaaatttt  8880 attcctttg cgttacctga aattggcgaa gaagaaattg cagaggtaat tgactcttta  8940
cgttcaggtt ggattacgac aggtcctaag gctaagcaat ttgaacaaga attttctaat  9000
tacctaggag cgaacgttca atcattagct gttaactctg ctacgtcggg cttacatttg  9060
gctcttgaag ctgttggcgt aaagccggga gaccaagtta ttgtcccatc atatacattc  9120
actgctactg ccgaaattgt caggtacctt ggtgctgatc ctgtaattgt tgatgtagat  9180
cgtaaaacat ttaatatatc agttgatgcc attgagaagg ctattactaa tgaaacaaag  9240
gcgattattc cagtacactt cgctggatta gcttgtgaca tggattcaat cttatcaatt  9300
gctaaaaaat atgacctaaa ggttgtcgag gatgccgctc atgcatttcc tacaacatat  9360
aaaggaagta agataggaac gcttgattca gatgctacgg ttttttagctt ctacgccaat  9420 aaaactatga caaccggtga aggcggaatg gttgtttcaa aaaataaaga tataattgag  9480
cgttgtaagg taatgcgttt acatggaatc agtcgtgacg cttttgaccg gtaccagtct  9540
aaaactcctt cttggtttta tgaggttgta gctccagggt ttaaatacaa tatgcctgat  9600
atctgtgcgg caatcggtat tcatcaactt agaaagatcg atgattttca gaaaaaacgt  9660
caacgaatgg caaaaattta cgatgatgcg ttaaaagaat tgccacttga attgcctgaa  9720
tggcctacta atgctagtga tattcatgct tggcatctat atcctatccg cttaaaaact  9780
gattcggcta ttaatcgcga tgattttatt aagaagttat cagatcttgg aattggttgt  9840
```

```
tctgtccatt ttataccgtt gcataagcaa ccggtttggc gtgatacata taatttgaac    9900
gccagtgact ttccagtttc tgaggagtgt tatttaaatg aaatatctat tcctctttat    9960
actaaaatga cggatcaaga tcagttgttc gttatcaaat cgattagaca attatttatg   10020
taatggtatt ttatattaaa tgaaacgtat ttttgatgtt atcgtggcag gcttaggcct   10080
gcttttctta tttcctgttt ttatcattgt gtcaatgtta attgttgctg attctaaagg   10140
gggggttttt tttaggcagt atagagttgg gagatttggg aaagatttta ggatacataa   10200
atttagaacg atgtttatcg attcagaaaa aaaaggacgg ataacagttg gtcaagatgc   10260
tcgggtaacc agagttggat ggtatttacg gaagtacaaa atcgatgagc ttcctcaatt   10320
gatagatgtt ctttctggaa caatgagttt ggttggccca agaccggaag tgagggagtt   10380
tattgatgag tatcctgatg atataaggga aaaagtttta tcggttaggc cagggataac   10440
tgacttagca tctatagaaa tggtagatga aaatgagatt ttgtctagtt atgatgaccc   10500
acgtagggct tatatagata taattcttcc aatcaagcaa agatattatt tagattatgt   10560
tgctaacaat tcagtaaagt atgattgtgt gataaatttgg aaaactatta ttaagatttt   10620
gtcgcgataa taaggtagtg taggatgatt gatagaatat tggagctgcc aagaattgtt   10680
aagagaggta tcatcatctg cattgatgta gttatggtga tattctcatt ttggttgtct   10740
tattggttga ggcttgatga gcaaacggct tttcttagtg caccgatgtg gtttgctgca   10800
gctattctta ccatatttac cgtgtttata tttatcagga ttgggcttta tcgggcagtc   10860
ttacggtatg ttagtgcaaa gataatgttg ctaataccag ttggtattct ggcctcaacg   10920
ttatctcttg tcgttatatc atattcgcta tccataatgt tgccgcgcac tgttgtcgga   10980 atttatttt tggttttact tttactgaca tcaggctcta gattgctttt tagaatgata   11040
cttaactatg gagttaaggg tagtgcgcct gttttgattt atggcgctgg tgaatctggc   11100
cgacaattat tgccagcatt aatgcaggca aaagaatatt ttcctgtggc atttgtggat   11160
gataatcctc gcttgcataa ggctgtcatt catggtgtaa cagtttatcc ctcggataaa   11220
ctgagttacc ttgtagatcg ctatggtata aagaaaattc ttttggcgat gccgagcgtc   11280
agtaagtcac aaaggcagaa agtgattact cgtttagagc atctaccgtg tgaagttctc   11340
tctattccgg gtatggtcga tttagtcgaa ggtcgagcac aaatcagtaa tctaaaaaaa   11400
gtatcgattg atgacttact aggtcgtgat ccggttgctc ctgatgccaa attgatggcc   11460
gaaaacatta ctggcaaagc cgttatggtc actggggcgg gaggctcgat cggctctgag   11520 cttttgtcgtc aaattgttcg atataagccg gccaaattgg ttctatttga actgtctgaa   11580
tatgccctct acgctattga gaaagagctc tcggcgctgt gcgacaaaga agttttgaat   11640
gttccagtga tccctctgtt gggctcggtg cagcgtcaga atcgcttaca gatggtgatg   11700
aagtcctttg gtattcaaac ggtttatcat gcggccgctt ataaacatgt gcctctggtt   11760
gagcataatg tggtggaagg ggtacgtaat aacgtgtttg gtaccttgta ctgcgctgag   11820
tcagcgatcg aaagtggcgt tgaaactttt gtgttgattt ccaccgataa agcggtgcgc   11880
ccgaccaaca ctatggggac aactaagcgt ctggccgaat tggtattgca ggctttgtct   11940
gcacggcaaa gccaaactcg cttttgtatg gtgcgatttg gtaatgtact cggttcttcg   12000
ggctctgtcg tgccgttgtt tgaaaaacag attgcccaag gtgggccagt taccttgact   12060
catcgtgaca ttattcgcta tttcatgaca attccggaag catcacagtt ggtgattcaa   12120
gcgggggcga tggggcatgg cggcgatgtc tttgtcttag acatgggcga tccggtcaag   12180
atttatgact tagccaaacg catgatccgg ttaagtggct tgagtgtacg ggatgataaa   12240
```

-continued

```
aatccagatg gcgatattgc cattgaagtt acgggattac gtccagggga gaaactgtat    12300
gaagaattac tgattggtga ttcagttcaa ggtacctctc atccacgaat tatgacggcc    12360
aacgaagtga tgctaccgtg gcaggatcta tcgctcttac ttaaagagct ggatcaagct    12420
t                                                                   12421
```

<210> SEQ ID NO 6
<211> LENGTH: 11022
<212> TYPE: DNA
<213> ORGANISM: Shigella sonnei
<220> FEATURE:
<223> OTHER INFORMATION: O antigen

<400> SEQUENCE: 6

```
aagcttgatc aaatagctca tattcagcga gatttaacaa ctgcggaaca agccggaatc      60
attgattatc gctctagcaa aggcggcttc gataatgcgc aaagtagcta taagttcttg     120
ctcggcgaaa aactgttatc agcagagcta aaagcaacta agatgcgcc aattatttac      180 ccatttagat attacgaagt gaaacgtcaa attgatgagt tagaaggaat gttacgcgat     240
aacattcagg cgcaagcata tcgatatcaa atgaagccat ctgagccagt tataaaagac     300
aaacccaaca aagcattaat tttgattctt ggtgcattac caggggcaat gtttgctata     360
gttggtacat tagtttatgc gacattaaaa gataaaacca agttagatta aactgggtta     420
cgtattgttg tgtcaatgcg aaatagatgt tctatgtgca ctttatgatg gataagaaaa     480
tgaaattcga tactttgaat gcgaaaattg ggattatagg ccttggttat gttggattgc     540
ctcttgctgt tgagtttgga aagaaagtaa cgacgattgg atttgatatt aataagtctc     600
gtattgatga attcgaaaat ggtcacgata gtacattaga gtgctcaaat ttagagttgt     660
tagaagcaac taaattgacg tacgcctgtt cattagatgc actaaaagag tgtaatgtat     720
ttattgtaac tgttccaact ccaattgata aacataaaca gccagatcta acacctctaa     780
ttaaagcatc tgaaacattg ggtaagataa taaagaaagg cgatgttatt atttatgagt     840
caacagttta ccctggagcg acagaagaag attgtatacc agttgtagag aaagtatcag     900
gtcttaagtt taatattgat ttttttgccg gttattcacc tgagcgtatt aatcctgggg     960
ataaagagca tcgtgtaact aatatcctta aggtgaccag tggatctaca ccggatgttg    1020
ctgagtatgt agatcagcta tataaattaa taattactgt cggtacgcat aaagcatcat    1080
cgataaaagt agcagaggct gcaaaagtaa ttgaaaacac gcagcgagat gtcaatattg    1140
cattgattaa tgagttatct attatattta ataagttagg gattgatacc ttagaggttc    1200
ttgaggctgc aggtacgaag tggaatttt tacctttag gcccggttta gtaggtggcc     1260
actgtatagg tgtagatcct tattatctta cacataaagc gcaaagtgtc ggctatcatc    1320
cggagatgat tttagccgga cgtcgtttaa atgatagtat ggggcagtat gtcgtttccc    1380
agttagtcaa aaaaatgttg aaacaacgga ttcaagttga aggggcgaat gtgttagtga    1440
tggggcttac attaaagag aattgcccag atctacgaaa cactaaagtg attgatatta    1500
tttcagagtt aaaagaatac aatatcaata tagatattat agatccatgg tgttctaccg    1560
atgaggcaca acatgaatat ggattaactt tatgtgaaga tcctaaagtt aatcattatg    1620
atgcaataat tatcgctgtt gcacacaatg agtttcgcga gatgggagag agcgctattc    1680
gtgcattagg taaagacgag cacgtttttgt tcgatttaaa atatgtgctt gataaaaaaa    1740
gtatcgatat gcgcttgtaa gagtgattaa aaaaatcaaa tcctctttga tatgatacac    1800
ctcagcattt tatgctaggt ttagcacttg attaatatac atggatattt atatgtctcg    1860
```

```
ctatgaagag attacacagc agttaatttt ttcaccgaaa acttggttaa ttactggtgt    1920
cgctggcttt ataggatcaa atcttttaga aaagttactt aaattaaacc aggttgttat    1980
tgggttagat aacttttcca cgggacatca atataatctt gatgaagtta aaacattagt    2040
ttccactgaa cagtggagtc gattttgctt tatagaaggt gatattcgag atctcactac    2100
ctgtgagcaa gttatgaaag gtgttgatca tgtcttacat caggctgcgc taggttctgt    2160
acctcgttca attgttgatc ctataacaac caatgcaact aatattactg gattttttgaa    2220 tatcttacat gcggctaaaa atgcacaagt acaaagtttt acttatgctg catcaagctc    2280
aacttatgga gatcatcccg cactaccaaa agtagaggaa acattggta atccactttc    2340 tccttatgca gttactaaat atgttaacga gatttatgct caggtatatg ctcgaacata    2400
tggttttaaa actattggat tacgttattt taatgtattt ggtcgtcgtc aagatcctaa    2460
tggagcttat gctgcagtaa ttccaaaatg gacagcagca atgcttaaag gtgatgacgt    2520
atatattaat ggcgatggtg aaacgagtcg tgattttgt tatatagata tgttataca     2580 aatgaatata ttatctgcat tagcgaagga cagtgctaaa gataatatat ataatgttgc    2640
agttggtgat agaacaacgt taaatgaatt atctggttac attatgatg agcttaattt    2700 aattcaccat atcgataaat tgagcattaa gtatagagag tttagatctg gagatgttag    2760
gcattctcag gctgatgtta ctaaggctat agatttacta aagtatagac caaatataaa    2820
aatcagagag ggattacgac tttcaatgcc gtggtatgtg agattttttaa aaggctaaat   2880 tatattaaca tgaataaata atctatttca cctctgttat taatgcaggg gtgaaaatcc    2940
atgtatttat tctaaatggt cagtgtatgt ttagaaaaat gattgatgca ggtggtacat    3000
ttttacttaa agcaatattt caaataggag tttttgttta tttcacacat gtgtcagata    3060
ttactacatt tggtattatt agttatgtgt ttactgttta ttggtttgtg cttaacttct    3120
ctgattatgg atttagaaca aaattagtga aagatatttc tgataatagt tattctgcat    3180
cagaattatt atcaagaagt gatggagtta aaacatatgt ttttttcttc attttttataa   3240 tcttcatgtt ttattcttat gtttctgatt caatttcatt aactctgctt gtttatattt    3300
catctgcata ttttgtttgt atttcaagtg gtagatttag cttgctacag gctgttggtc    3360
ggtttagatg tgaattatat ataaatatct actcaacaat tatatatatt gggtgtaatt    3420
tatttttatc tctgtttatc gaacctctat attatagtgc gatatcaata ttcatatact    3480
caatttcgct tttggttttc tcatcacata atgcaatgt gccatgtttt catataaaaa     3540
gaccaagtat tttagtttat aaagattttt tggatgcaac tccgttcgct attctggtgt    3600
tactaaatgt tgttttatct agtattgacc tttttatatt aaaagaatat ttctcttata    3660
atagtgttgc tatatatcag gtggtaacta gggttaatac cggtctaata atagtgttta    3720
atgttattta tactgttta ttgccttcat tttcttatta tctgaaaaat tctgaatggg      3780
gtaatataag gaaattacaa cgatatatat cactgttagt cttattacta tgtttatgct    3840 attattttt tggcatctat ttcgtaggga tattgtttgg tgatgagtat aaggtaatat     3900
cttctgcaac atttttgata atgtttatgg ctccttattaa atataatttt tggctaataa   3960
atgaacttta tcttgtgtgt agtggaaatc aaagcgagcg agttaaatcg tattgtattg    4020
gtgtggtcat ttcaatggcg gttttctttt attttatacc tcggtatgga tggagtgggg    4080 cggttttttgg aagtgccatt gcaacattag taattggaat attttatatt atttctgtga   4140
aaaaagattg tgggaaaatt cttcatgata agtattcact aatgatgatc tttgtcccaa    4200
ttttctttta ttttattatt aatggtcagc agcggttgtt atattaatat gttgtggttt    4260
```

```
tatatcgttc cattaatatg tttagactcg attggaagcc taataaaggt taagtatgtt    4320
aatataccta tatcctgtac ttttgttatt taatatcctt ccggttttt  tttatggaca    4380 aatgaactct gatttagagc gttttttttgg agttcctatt ggctatattc cagatctaat   4440 atttatttc  tttgttgttt taacatctat aataacgttg aggtttcacg tttctctgtg    4500
gacaaagaaa ttattatttt taggcatcat attcctgatt tatatcagca ttcagatgtt    4560
gttgttatca gcggatatat caggtgtcgt aattttatta tcgttttttt ctaattttat    4620
agctttggtt cttttggtgt cattttgcat tggtaaagat gagctttatt taactcattc    4680
ggttagaaat ataaatgttg taatgtgttt tggtattatc tgtggagttg taaaattatt    4740
tattggttat tctgaagata gtaatttat  agtttattta aatagaaatg ccaccgcaat    4800
tatagtagtg tgcttttatt gtgtatattc atactttat  cgtggtcgaa agtcttggta    4860
tgtctcatct gtattgtact ctctgttctt tcttttctg  gatagccgag caggaataat    4920
atcatttgct atatcgttgt tttttgtttt tcttcagtta acaaagaagg aaaagttatt    4980
aatatcattg tttttgttc  ctcttctaac tttaggtatt tcttttactg atataggcac    5040
tcgtcttgaa cgaatgctgt cttcgtcaca ggtatattc  tctggtggta acactcttac    5100
aaaaagtcag aatgattatc gtcgagttga gttagtattt attggggttg atgttttaaa    5160
agaaaattat ttaattggca ctggattagg tgttgcaaat tatgtaaagg ctatagataa    5220
aaagttttta ggaagtacca actttgggtt ggcgcataat ttttatttat cttattcggc    5280
tcagttaggg attattggtt ttattttgct tatttctgta ttttatataa tgctgtctcc    5340 aattttaaa  tgcggagggt atattggtaa aggatgcgtt tttgctttgg cttctatgt    5400 cttttttaat gagtatatat tgacgccagc gatatatatt tatatttcta ttttttatc    5460 ggtggttttt atacgtaatt ctaaatagct gcgcggaata gtagatcact ttgagggaac    5520
ttagcccgga ttgtgcgatc tgatcaatcg ccaaatcaaa acaaatcacc aaccggactg    5580
agcaatgccg atcatagcac caatttcccg tgacgaacga cgcctgatgc agaaagccat    5640
ccataaaaca cacgataaaa attatgcccg cagactgact gccatgctga tgctgcaccg    5700
gggcgaccgt gtcagcgacg ttgccagaac gctctgctgc gcccgttcct ctgttggacg    5760
ctggattaac tggttcacgc agtcgggtgt tgagggactg aaatcattac ctgccgggcg    5820
tgcccgtcgc tggccgtttg agcatatctg cacactgtta cgtgagctgg taaaacattc    5880
tcccggcgac tttggctacc agcgttcacg ctggagtaca gaactgctgg caataaaaat    5940
caatgagata accggttgcc agttaaatgc cggaaccgtt cgccgctggt tgccgtctgc    6000
ggggattgtg tggcgaaggg ctgcgccaac tctgcgtatc cgtgacccgc ataaagatga    6060
aaagatggca gcaatccata aagcactgga cgaatgcagc gcagagcatc cggtctttta    6120
tgaagatgaa gtggatatcc atcttaatcc caaaatcggt gcggactggc aactgcgcgg    6180
acagcaaaaa cgggtggtca cgccgggaca gaatgaaaaa tattatctgg ccggagcgct    6240
gcacagcggg acaggtaaag tcagctgtgt gggcggcaac agcaaaagtt cggcgctgtt    6300
catcagcctg ctgaagcggc ttaaagcgac ataccgtcgg gcgaaaacca tcacgctgat    6360
cgtggacaac tacattatcc acaaaagccg ggaaacacag agctggctga aggagaaccc    6420
gaagttcagg gtcattttatc agccggttta ctcgccatgg atgaatcatg ttgaacggct    6480
atggcaggca cttcacgaca caataacgcg taatcatcag tgcagctcaa tgtggcaact    6540
gttgaaaaaa gttcgccatt ttatggaaac cgtcagccca ttccccggag caaacatgg    6600 gctggcaaaa gtgtagcggt attaagcgca gctatttagg atgagaatat gttgttagaa    6660
```

```
tatgttgaaa gaaaaatttc cttagccttg agtaagtatc ctaaggtaag ggatgttatt      6720
aagttctttt atttatatat cgcatcatta ttcggaatta ttttgaataa aaataagacg      6780
gttattcaat caaaaatata cgagatttca attgatgatt ctgaagaatc attttttggc      6840
tattatgacc atagtccaat gagctctaat gggcggtacg tattgttcca ctctagtgcg      6900
tttagcacta aacgacatcc aaagaaagtt aagtatatat ctatttgcgt aaaagacctt      6960
cttaataaca aagtttataa gctatatgat acgcgagcat ttaattggca gcagggaagc      7020
cgattaatgt ggattgatga tgacaatata attttttaatg actatgaaaa taatggatac      7080
attagtgttg tctattcttt gtctttgatg aaggttataa aaaaaataaa ctatccgatt      7140
tatgatgtga ataattacaa ggctgtgacg ttagatttct catggctggc taaatatgat      7200
agcgattatg gttattataa taaaaaatca ttttctacag atatttcaat cattaatttg      7260
aatacggggg gaatagaatt attttttatcc ttagacgaaa tgctaaagag aactaattt      7320 aaatgtaata ttgatgttga acatgtggtc aatcattta tgtttgctcc cgatggacgt      7380
tccgttatgt tcatacatcg atactataca cctaaaggaa agcgtgaaag gttaatacat      7440 tggaattttaa taaatgataa tgttcgagtc ctaataaatg aatcgattat tagtcattgt      7500
tgttggaatg ggaatgatga aattataggt ttttttggtg cagaaataga ttcgctaaat      7560
tattatagat tgtcaattga atcctgtaat acagagaaat tgttttttga tgcaagaaaa      7620
tattctgatg gacatcctac tatagttcat aatagatata ttatatctga tacttaccca      7680
gataaaaata gaattaaaaa gttgtttgtt tatgaccttg tcaaaaatga ttatcgcgag      7740
cttggattat tttatgagtc aatgagtttt tttttcttatt ctcgatgtga cttacatcca      7800
aggatctcgg ttgataatag attttttgttt gttgattcag ttcactcagg aaaagaaaa      7860 ctatatttta tgaggagtgg tatttgtgag tgatgttcta gtatctttaa ttatagtttg      7920
ctttaatgca gagaagtata ttgaaaaatc tcttttggca tttattaatc aagatgttgg      7980
attagataaa tttgaattga ttattgtaga tggggattca tctgataata caatatctat      8040
tgttcaggat gttttttcta aacatagcaa cattaagcat aaaattatca ataataaaaa      8100
aagaactctt gctacgggtt ggaatattgg ggtgctagaa gctaatggta agtttgtgtg      8160
tagagttgat gcacatagtg atattccaaa taactatata tctaaattat tagatgatta      8220
ttttaatatt atgcagtttg atgatagcgt tgttggtgtt ggaggtgtat taactaattc      8280
ttataaaact aagtttggtt caattgtagc ggattttat gcatcgaaat ttggtgttgg      8340
taattctcca tttaggtgcg tagacaaaaa taatcgacta aaaaaaacag atacagctgt      8400
ctttgcttta tataataaag atgtgttttt tgatgttgga cttttttaatg aagtattaga      8460 tagaaatcaa gatattgatt ttcataagag agttttaagc aataatttgt cattatatac      8520
agataatagt ttatttgttg agtattatgt tagagataat tttaaagatt tcataaagaa      8580
aggttttctt gatggttttt gggttgttat gtctggagca tattatttta gacatatagt      8640 gccactttttt tttgttttgt atttaattgt atctttttct cttttctttg ctactggtga      8700
ttatatatat ttatctttttt tatttttta ttttcttatt tctattttgt tttcaattcg      8760
agatgggcga agtttatag gtagagtatt tcttcctttt atattttgt cttatcatat      8820 ttcttatgga tgtggatcgt tattatcttt tttgaaaagg tattttaaat gaaaaatttt      8880
attccttttg cgttacctga aattggcgaa gaagaaattg cagaggtaat tgactcttta      8940
cgttcaggtt ggattacgac aggtcctaag gctaagcaat ttgaacaaga attttctaat      9000
tacctaggag cgaacgttca atcattagct gttaactctg ctacgtcggg cttacatttg      9060
```

-continued

```
gctcttgaag ctgttggcgt aaagccggga gaccaagtta ttgtcccatc atatacattc   9120
actgctactg ccgaaattgt caggtacctt ggtgctgatc ctgtaattgt tgatgtagat   9180
cgtaaaacat ttaatatatc agttgatgcc attgagaagg ctattactaa tgaaacaaag   9240
gcgattattc cagtacactt cgctggatta gcttgtgaca tggattcaat cttatcaatt   9300
gctaaaaaat atgacctaaa ggttgtcgag gatgccgctc atgcatttcc tacaacatat   9360
aaaggaagta agataggaac gcttgattca gatgctacgg tttttagctt ctacgccaat   9420
aaaactatga caaccggtga aggcggaatg gttgtttcaa aaaataaaga tataattgag   9480
cgttgtaagg taatgcgttt acatggaatc agtcgtgacg cttttgaccg gtaccagtct   9540
aaaactcctt cttggtttta tgaggttgta gctccagggt ttaaatacaa tatgcctgat   9600
atctgtgcgg caatcggtat tcatcaactt agaaagatcg atgattttca gaaaaaacgt   9660
caacgaatgg caaaaattta cgatgatgcg ttaaaagaat tgccacttga attgcctgaa   9720
tggcctacta atgctagtga tattcatgct tggcatctat atcctatccg cttaaaaact   9780
gattcggcta ttaatcgcga tgattttatt aagaagttat cagatcttgg aattggttgt   9840
tctgtccatt ttataccgtt gcataagcaa ccggtttggc gtgatacata taatttgaac   9900
gccagtgact ttccagtttc tgaggagtgt tatttaaatg aaatatctat tcctctttat   9960
actaaaatga cggatcaaga tcagttgttc gttatcaaat cgattagaca attatttatg  10020
taatggtatt ttatattaaa tgaaacgtat ttttgatgtt atcgtggcag gcttaggcct  10080
gctttttcta tttcctgttt ttatcattgt gtcaatgtta attgttgctg attctaaagg  10140
gggggttttt tttaggcagt atagagttgg gagatttggg aaagatttta ggatacataa  10200
atttagaacg atgtttatcg attcagaaaa aaaaggacgg ataacagttg gtcaagatgc  10260
tcgggtaacc agagttggat ggtatttacg gaagtacaaa atcgatgagc ttcctcaatt  10320
gatagatgtt ctttctggaa caatgagttt ggttggccca agaccggaag tgagggagtt  10380
tattgatgag tatcctgatg atataaggga aaaagtttta tcggttaggc cagggataac  10440
tgacttagca tctatagaaa tggtagatga aaatgagatt ttgtctagtt atgatgaccc  10500
acgtagggct tatatagata taattcttcc aatcaagcaa agatattatt tagattatgt  10560
tgctaacaat tcagtaaagt atgattgtgt gataatttgg aaaactatta ttaagatttt  10620
gtcgcgataa taaggtagtg taggatgatt gatagaatat tggagctgcc aagaattgtt  10680
aagagaggta tcatcatctg cattgatgta gttatggtga tattctcatt ttggttgtct  10740
tattggttga ggcttgatga gcaaacggct tttcttagtg caccgatgtg gtttgctgca  10800
gctattctta ccatatttac cgtgtttata tttatcagga ttgggcttta tcgggcagtc  10860
ttacggtatg ttagtgcaaa gataatgttg ctaataccag ttggtattct ggcctcaacg  10920
ttatctcttg tcgttatatc atattcgcta tccataatgt tgccgcgcac tgttgtcgga  10980
atttattttt tggttttact tttactgaca tcaggctcta ga                      11022
```

<210> SEQ ID NO 7
<211> LENGTH: 17986
<212> TYPE: DNA
<213> ORGANISM: Shigella sonnei
<220> FEATURE:
<223> OTHER INFORMATION: GenBank Accession No. AF294823, Shigella sonnei O protein, Shigella sonnei O antigen gene cluster, complete sequence

```
<400> SEQUENCE: 7
ggtaatggct ccaacttatt gatagtgttt tatgttcaga taatgcccga tgactttgtc    60
atgcagctcc accgattttg agaacgacag cgacttccgt cccagccgtg ccaggtgctg   120
cctcagattc aggttatgcc gctcaattcg ctgcgtatat cgcttgctga ttacgtgcag   180
cttccccttc aggcgggatt catacagcgg ccagccatcc gtcatccata tcaccacgtc   240
aaagggtgac agcaggctca taagacgccc cagcgtcgcc atagtgcgtt caccgaatac   300
gtgcgcaaca accgtcttcc ggagactgtc atacgcgtaa aacagccagc gctggcgcga   360
tttagccccg acatagcccc actgttcgtc catttccgcg cagacgatga cgtcactgcc   420
cggctgtatg cgcgaggtta ccgactgcgg cctgagtttt taagtgacg taaaatcgtg    480
ttgaggccaa cgcccataat gcgtgcagtt gcccggcatc caacgccatt catggccata   540
tcaatgattt tctggtgcgt accgggttgg gaagcggtgt aagtgaactg cagttgccat   600
gttttacggc agtgagagca gagatagcgc tgatgtccgg cagtgctttt gccgttacgc   660
accacccgt cagtagctga acaggaggga cagctgatag aaacagaagc cactggagca    720
cctcaaaaac accatcatac actaaatcag taagttggca gcatcaccga ctacggggtt   780
agcagcagtg tatgccttta ccgcaaaaga gcagtggacg gctaaaacct atattcaagc   840
accacgtatt gctgaattag gcagctatct taaatttcac caagcgtatg cccgaatatt   900
aaatcaaccg ttagatacga atgcgttggc taatggattg ttttccgatt tgattttgat   960
tgctgaatcg ccagacacca aagttaaatt tctagagagt actgagtatt ataaaaagga  1020
aacaaataat ttatctactg accaagataa gaaaatttgg ttagctgagc aagcgaataa  1080
aggtcttgtg attacgccac caaaggaaaa gggaaataca agttactaca taatacaagc  1140
atcggcagac tcagcgcaag aggcatataa actactgcag ggatatctaa agaatgttaa  1200
taatcaagct gtaacattaa gtcttgatga gtttggtcaa aatgttaata ctcttttggt  1260
taatctaaat aaagaaatta ttgacataga tttccagaga aaatcagaaa agcttgatca  1320
aatagctcat attcagcgag atttaacaac tgcggaacaa gccggaatca ttgattatcg  1380
ctctagcaaa ggcggcttcg ataatgcgca aagtagctat aagttcttgc tcggcgaaaa  1440
actgttatca gcagagctaa aagcaactaa agatgcgcca attatttacc catttagata  1500
ttacgaagtg aaacgtcaaa ttgatgagtt agaaggaatg ttacgcgata acattcaggc  1560
gcaagcatat cgatatcaaa tgaagccatc tgagccagtt ataaaagaca aacccaacaa  1620
agcattaatt ttgattcttg gtgcattacc agggcaatg tttgctatag ttggtacatt   1680
agtttatgcg acattaaaag ataaaaccaa gttagattaa actgggttac gtattgttgt  1740
gtcaatgcga aatagatgtt ctatgtgcac tttatgatgg ataagaaaat gaaattcgat  1800
actttgaatg cgaaaattgg gattataggc cttggttatg ttggattgcc tcttgctgtt  1860
gagtttggaa agaaagtaac gacgattgga tttgatatta ataagtctcg tattgatgaa  1920
ttacgaaatg gtcacgatag tacattagag tgctcaaatt tagagttgtt agaagcaact  1980
aaattgacgt acgcctgttc attagatgca ctaaaagagt gtaatgtatt tattgtaact  2040
gttccaactc caattgataa acataaacag ccagatctaa cacctctaat taaagcatct  2100
gaaacattgg gtaagataat aaagaaaggc gatgttatta tttatgagtc aacagtttac  2160
cctggagcga cagaagaaga ttgtatacca gttgtagaga aagtatcagg tcttaagttt  2220
aatattgatt ttttgccgg ttattcacct gagcgtatta tcctggggga taaagagcat  2280
cgtgtaacta atatccttaa ggtgaccagt ggatctacac cggatgttgc tgagtatgta  2340
```

-continued

```
gatcagctat ataaattaat aattactgtc ggtacgcata aagcatcatc gataaaagta    2400
gcagaggctg caaaagtaat tgaaaacacg cagcgagatg tcaatattgc attgattaat    2460
gagttatcta ttatatttaa taagttaggg attgatacct tagaggttct tgaggctgca    2520
ggtacgaagt ggaattttt acctttagg cccggtttag taggtggcca ctgtataggt     2580
gtagatcctt attatcttac acataaagcg caaagtgtcg gctatcatcc ggagatgatt    2640
ttagccggac gtcgtttaaa tgatagtatg ggcagtatg tcgtttccca gttagtcaaa    2700
aaaatgttga aacaacggat tcaagttgaa ggggcgaatg tgttagtgat ggggcttaca    2760
tttaaagaga attgcccaga tctacgaaac actaaagtga ttgatattat tcagagtta    2820 aaagaataca atatcaatat agatattata gatccatggt gttctaccga tgaggcacaa    2880
catgaatatg gattaacttt atgtgaagat cctaaagtta atcattatga tgcaataatt    2940
atcgctgttg cacacaatga gtttcgcgag atgggagaga gcgctattcg tgcattaggt    3000
aaagacgagc acgttttgtt cgattaaaa tatgtgcttg ataaaaaaag tatcgatatg     3060
cgcttgtaag agtgattaaa aaaatcaaat cctctttgat atgatacacc tcagcatttt    3120
atgctaggtt tagcacttga ttaatataca tggatattta tatgtctcgc tatgaagaga    3180
ttacacagca gttaatttt tcaccgaaaa cttggttaat tactggtgtc gctggcttta    3240
taggatcaaa tcttttagaa aagttactta aattaaacca ggttgttatt gggttagata    3300
acttttccac gggacatcaa tataatcttg atgaagttaa aacattagtt tccactgaac    3360
agtggagtcg atttgctt atagaaggtg atattcgaga tctcactacc tgtgagcaag     3420
ttatgaaagg tgttgatcat gtcttacatc aggctgcgct aggttctgta cctcgttcaa    3480
ttgttgatcc tataacaacc aatgcaacta atattactgg attttgaat atcttacatg     3540 cggctaaaaa tgcacaagta caaagtttta cttatgctgc atcaagctca acttatggag    3600
atcatcccgc actaccaaaa gtagaggaaa acattggtaa tccactttct ccttatgcag    3660
ttactaaata tgttaacgag atttatgctc aggtatatgc tcgaacatat ggttttaaaa    3720
ctattggatt acgttatttt aatgtatttg gtcgtcgtca agatcctaat ggagcttatg    3780
ctgcagtaat tccaaaatgg acagcagcaa tgcttaaagg tgatgacgta tatattaatg    3840
gcgatggtga aacgagtcgt gattttgtt atatagataa tgttatacaa atgaatatat    3900
tatctgcatt agcgaaggac agtgctaaag ataaatatata taatgttgca gttggtgata    3960
gaacaacgtt aaatgaatta tctggttaca tttatgatga gcttaattta attcaccata    4020
tcgataaatt gagcattaag tatagagagt ttagatctgg agatgttagg cattctcagg    4080
ctgatgttac taaggctata gatttactaa agtatagacc aaatataaaa atcagagagg    4140
gattacgact ttcaatgccg tggtatgtga gattttaaa aggctaaatt atattaacat    4200
gaataaataa tctatttcac ctctgttatt aatgcagggg tgaaaatcca tgtatttatt    4260
ctaaatggtc agtgtatgtt tagaaaaatg attgatgcag gtggtacatt tttacttaaa    4320
gcaatatttc aaataggagt ttttgtttat ttcacacatg tgtcagatat tactacattt    4380
ggtattatta gttatgtgtt tactgtttat tggtttgtgc ttaacttctc tgattatgga    4440
tttagaacaa aattagtgaa agatatttct gataatagtt attctgcatc agaattatta    4500
tcaagaagtg atggagttaa aacatatgtt tttttcttca ttttataat cttcatgttt     4560 tattcttatg tttctgattc aatttcatta actctgcttg tttatatttc atctgcatat    4620
tttgtttgta tttcaagtgg tagatttagc ttgctacagg ctgttggtcg gtttagatgt    4680
gaattatata taaatatcta ctcaacaatt atatatattg ggtgtaattt attttttatct    4740
```

```
ctgtttatcg aacctctata ttatagtgcg atatcaatat tcatatactc aatttcgctt    4800
ttggttttct catcacataa atgcaatgtg ccatgttttc atataaaaag accaagtatt    4860
ttagtttata aagattttt ggatgcaact ccgttcgcta ttctggtgtt actaaatgtt    4920
gttttatcta gtattgacct ttttatatta aaagaatatt tctcttataa tagtgttgct    4980
atatatcagg tggtaactag ggttaatacc ggtctaataa tagtgtttaa tgttatttat    5040
actgttttat tgccttcatt ttcttattat ctgaaaaatt ctgaatgggg taatataagg    5100
aaattacaac gatatatatc actgttagtc ttattactat gtttatgcta ttattttttt    5160
ggcatctatt tcgtagggat attgtttggt gatgagtata aggtaatatc ttctgcaaca    5220
tttttgataa tgtttatggc tcttattaaa tataattttt ggctaataaa tgaactttat    5280
cttgtgtgta gtgaaatca aagcgagcga gttaaatcgt attgtattgg tgtggtcatt    5340
tcaatggcgg ttttcttta ttttatacct cggtatggat ggagtggggc ggttttgga    5400 agtgccattg caacattagt aattggaata ttttatatta tttctgtgaa aaagattgt    5460 gggaaaattc ttcatgataa gtattcacta atgatgatct tgtcccaat tttcttttat    5520 tttattatta atggtcagca gcggttgtta tattaatatg ttgtggtttt atatcgttcc    5580
attaatatgt ttagactcga ttggaagcct aataaaggtt aagtatgtta atatacctat    5640
atcctgtact tttgttattt aatatccttc cggtttttt ttatggacaa atgaactctg    5700
atttagagcg ttttttgga gttcctattg gctatattcc agatctaata ttttatttct    5760
ttgttgtttt aacatctata ataacgttga ggtttcacgt ttctctgtgg acaaagaaat    5820
tattattttt aggcatcata ttcctgattt atatcagcat tcagatgttg ttgttatcag    5880
cggatatatc aggtgtcgta attttattat cgttttttc taattttata gctttggttc    5940
ttttggtgtc attttgcatt ggtaaagatg agctttattt aactcattcg gttagaaata    6000
taaatgttgt aatgtgtttt ggtattatct gtggagttgt aaaattattt attggttatt    6060
ctgaagatag taattttata gtttatttaa atagaaatgc caccgcaatt atagtagtgt    6120
gcttttattg tgtatattca tactttttatc gtggtcgaaa gtcttggtat gtctcatctg    6180
tattgtactc tctgttctt cttttctgg atagccgagc aggaataata tcatttgcta    6240
tatcgttgtt ttttgttttt cttcagttaa caaagaagga aaagttatta atatcattgt    6300 ttttttgttcc tcttctaact ttaggtattt cttttactga tataggcact cgtcttgaac    6360
gaatgctgtc ttcgtcacag gttatattct ctggtggtaa cactcttaca aaaagtcaga    6420
atgattatcg tcgagttgag ttagtattta ttggggttga tgttttaaaa gaaaattatt    6480
taattggcac tggattaggt gttgcaaatt atgtaaaggc tatagataaa aagttttag    6540 gaagtaccaa ctttgggttg gcgcataatt tttatttatc ttattcggct cagttaggga    6600
ttattggttt tattttgctt atttctgtat tttatataat gctgtctcca attttttaaat    6660 gcggagggta tattggtaaa ggatgcgttt ttgctttggc tttctatgtc tttttaatg    6720 agtatatatt gacgccagcg atatatattt atatttctat tttttttatcg gtggttttta    6780 tacgtaattc taaatagctg cgcggaatag tagatcactt tgagggaact tagcccggat    6840
tgtgcgatct gatcaatcgc caaatcaaaa caaatcacca accggactga gcaatgccga    6900
tcatagcacc aatttcccgt gacgaacgac gcctgatgca gaaagccatc cataaaacac    6960
acgataaaaa ttatgcccgc agactgactg ccatgctgat gctgcaccgg ggcgaccgtg    7020
tcagcgacgt tgccagaacg ctctgctgcg cccgttcctc tgttgacgc tggattaact    7080 ggttcacgca gtcgggtgtt gagggactga aatcattacc tgccgggcgt gcccgtcgct    7140
```

```
ggccgtttga gcatatctgc acactgttac gtgagctggt aaaacattct cccggcgact    7200
ttggctacca gcgttcacgc tggagtacag aactgctggc aataaaaatc aatgagataa    7260
ccggttgcca gttaaatgcc ggaaccgttc gccgctggtt gccgtctgcg gggattgtgt    7320
ggcgaagggc tgcgccaact ctgcgtatcc gtgacccgca taaagatgaa aagatggcag    7380
caatccataa agcactggac gaatgcagcg cagagcatcc ggtctttat gaagatgaag     7440 tggatatcca tcttaatccc aaaatcggtg cggactggca actgcgcgga cagcaaaaac    7500
gggtggtcac gccgggacag aatgaaaaat attatctggc cggagcgctg cacagcggga    7560
caggtaaagt cagctgtgtg ggcggcaaca gcaaaagttc ggcgctgttc atcagcctgc    7620
tgaagcggct aaagcgaca taccgtcggg cgaaaaccat cacgctgatc gtggacaact    7680
acattatcca caaagccgg gaaacacaga gctggctgaa ggagaacccg aagttcaggg     7740
tcatttatca gccggtttac tcgccatgga tgaatcatgt tgaacggcta tggcaggcac    7800
ttcacgacac aataacgcgt aatcatcagt gcagctcaat gtggcaactg ttgaaaaaag    7860
ttcgccattt tatggaaacc gtcagcccat tccccggagg caaacatggg ctggcaaaag    7920
tgtagcggta ttaagcgcag ctatttagga tgagaatatg ttgttagaat atgttgaaag    7980
aaaaatttcc ttagccttga gtaagtatcc taaggtaagg gatgttatta agttcttta    8040 tttatatatc gcatcattat tcggaattat tttgaataaa aataagacgg ttattcaatc    8100
aaaaatatac gagatttcaa ttgatgattc tgaagaatca tttttttggct attatgacca    8160 tagtccaatg agctctaatg ggcggtacgt attgttccac tctagtgcgt ttagcactaa    8220
acgacatcca agaaagtta agtatatc tatttgcgta aaagaccttc ttaataacaa       8280
agtttataag ctatatgata cgcgagcatt taattggcag cagggaagcc gattaatgtg    8340
gattgatgat gacaatataa ttttttaatga ctatgaaaat aatggataca ttagtgttgt   8400
ctattctttg tctttgatga aggttataaa aaaaataaac tatccgattt atgatgtgaa    8460
taattacaag gctgtgacgt tagatttctc atggctggct aaatatgata gcgattatgg    8520
ttattataat aaaaaatcat tttctacaga tatttcaatc attaatttga atacgggggg    8580
aatagaatta ttttatcct tagacgaaat gctaaagaga actaattta aatgtaatat      8640 tgatgttgaa catgtggtca atcattttat gtttgctccc gatggacgtt ccgttatgtt    8700
catacatcga tactatacac ctaaaggaaa gcgtgaaagg ttaatacatt ggaatttaat    8760
aaatgataat gttcgagtcc taataaatga atcgattatt agtcattgtt gttggaatgg    8820
gaatgatgaa attataggtt tttttggtgc agaaatagat tcgctaaatt attatagatt    8880
gtcaattgaa tcctgtaata cagagaaatt gttttttgat gcaagaaaat attctgatgg    8940
acatcctact atagttcata atagatatat tatatctgat acttacccag ataaaaatag    9000
aattaaaaag ttgtttgttt atgaccttgt caaaaatgat tatcgcgagc ttggattatt    9060
ttatgagtca atgagttttt tttcttattc tcgatgtgac ttacatccaa ggatctcggt    9120
tgataataga tttttgtttg ttgattcagt tcactcaggg aaaagaaaac tatattttat    9180
gaggagtggt atttgtgagt gatgttctag tatctttaat tatagtttgc tttaatgcag    9240
agaagtatat tgaaaaatct cttttggcat ttattaatca agatgttgga ttagataaat    9300
ttgaattgat tattgtagat ggggattcat ctgataatac aatatctatt gttcaggatg    9360 tttttttctaa acatagcaac attaagcata aaattatcaa taataaaaaa agaactcttg    9420 ctacggggttg gaatattggg gtgctagaag ctaatggtaa gtttgtgtgt agagttgatg    9480
cacatagtga tattccaaat aactatatat ctaaattatt agatgattat tttaatatta    9540
```

```
tgcagtttga tgatagcgtt gttggtgttg gaggtgtatt aactaattct tataaaacta   9600
agtttggttc aattgtagcg gattttatg catcgaaatt tggtgttggt aattctccat    9660
ttaggtgcgt agacaaaaat aatcgactaa aaaaaacaga tacagctgtc tttgctttat   9720
ataataaaga tgtgtttttt gatgttggac tttttaatga agtattagat agaaatcaag   9780
atattgattt tcataagaga gttttaagca ataatttgtc attatataca gataatagtt   9840
tatttgttga gtattatgtt agagataatt ttaaagattt cataaagaaa ggttttcttg   9900
atggttttg ggttgttatg tctggagcat attattttag acatatagtg ccactttttt    9960
ttgttttgta tttaattgta tcttttttctc ttttctttgc tactggtgat tatatatatt  10020
tatctttttt attttttat tttcttattt ctattttgtt ttcaattcga gatgggcgaa    10080
gttttatagg tagagtattt cttcctttta tattttgtc ttatcatatt tcttatggat    10140
gtggatcgtt attatctttt ttgaaaaggt attttaaatg aaaaatttta ttccttttgc   10200
gttacctgaa attggcgaag aagaaattgc agaggtaatt gactcttac gttcaggttg    10260
gattacgaca ggtcctaagg ctaagcaatt tgaacaagaa ttttctaatt acctaggagc   10320
gaacgttcaa tcattagctg ttaactctgc tacgtcgggc ttacatttgg ctcttgaagc   10380
tgttggcgta aagccgggag accaagttat tgtcccatca tatacattca ctgctactgc   10440
cgaaattgtc aggtaccttg tgctgatcc tgtaattgtt gatgtagatc gtaaaacatt    10500
taatatatca gttgatgcca ttgagaaggc tattactaat gaaacaaagg cgattattcc   10560
agtacacttc gctggattag cttgtgacat ggattcaatc ttatcaattg ctaaaaaata   10620
tgacctaaag gttgtcgagg atgccgctca tgcatttcct acaacatata aaggaagtaa   10680
gataggaacg cttgattcag atgctacggt ttttagcttc tacgccaata aaactatgac   10740
aaccggtgaa ggcggaatgg ttgtttcaaa aaataaagat ataattgagc gttgtaaggt   10800
aatgcgttta catggaatca gtcgtgacgc ttttgaccgg taccagtcta aaactccttc   10860
ttggttttat gaggttgtag ctccagggtt taaatacaat atgcctgata tctgtgcggc   10920
aatcggtatt catcaactta gaaagatcga tgattttcag aaaaaacgtc aacgaatggc   10980
aaaaatttac gatgatgcgt taaaagaatt gccacttgaa ttgcctgaat ggcctactaa   11040
tgctagtgat attcatgctt ggcatctata tcctatccgc ttaaaaactg attcggctat   11100
taatcgcgat gattttatta agaagttatc agatcttgga attggttgtt ctgtccattt   11160
tataccgttg cataagcaac cggtttggcg tgatacatat aatttgaacg ccagtgactt   11220
tccagtttct gaggagtgtt attaaatga aatatctatt cctctcttata ctaaaatgac   11280
ggatcaagat cagttgttcg ttatcaaatc gattagacaa ttatttatgt aatggtattt   11340
tatattaaat gaaacgtatt tttgatgtta tcgtggcagg cttaggcctg cttttttctat  11400
ttcctgtttt tatcattgtg tcaatgttaa ttgttgctga ttctaaaggg ggggttttt    11460
ttaggcagta tagagttggg agattggga aagattttag gatacataaa tttgaaacga   11520
tgtttatcga ttcagaaaaa aaaggacgga taacagttgg tcaagatgct cgggtaacca   11580
gagttggatg gtatttacgg aagtacaaaa tcgatgagct tcctcaattg atagatgttc   11640
tttctggaac aatgagtttg gttggcccaa gaccggaagt gagggagttt attgatgagt   11700
atcctgatga tataagggaa aaagtttttat cggttaggcc agggataact gacttagcat   11760
ctatagaaat ggtagatgaa aatgagattt tgtctagtta tgatgaccca cgtagggctt   11820
atatagatat aattcttcca atcaagcaaa gatattattt agattatgtt gctaacaatt   11880
cagtaaagta tgattgtgtg ataatttgga aaactattat taagatttg tcgcgataat    11940
```

```
aaggtagtgt aggatgattg atagaatatt ggagctgcca agaattgtta agagaggtat   12000
catcatctgc attgatgtag ttatggtgat attctcattt tggttgtctt attggttgag   12060
gcttgatgag caaacggctt ttcttagtgc accgatgtgg tttgctgcag ctattcttac   12120
catatttacc gtgtttatat ttatcaggat tgggctttat cgggcagtct tacggtatgt   12180
tagtgcaaag ataatgttgc taataccagt tggtattctg gcctcaacgt tatctcttgt   12240
cgttatatca tattcgctat ccataatgtt gccgcgcact gttgtcggaa tttatttttt   12300
ggttttactt ttactgacat caggctctag attgcttttt agaatgatac ttaactatgg   12360
agttaagggt agtgcgcctg ttttgattta ggcgctggt gaatctggcc gacaattatt   12420
gccagcatta atgcaggcaa aagaatattt tcctgtggca tttgtggatg ataatcctcg   12480
cttgcataag gctgtcattc atggtgtaac agtttatccc tcggataaac tgagttacct   12540
tgtagatcgc tatggtataa agaaaattct tttggcgatg ccgagcgtca gtaagtcaca   12600
aaggcagaaa gtgattactc gtttagagca tctaccgtgt gaagttctct ctattccggg   12660
tatggtcgat ttagtcgaag gtcgagcaca aatcagtaat ctaaaaaaag tatcgattga   12720
tgacttacta ggtcgtgatc cggttgctcc tgatgccaaa ttgatggccg aaaacattac   12780
tggcaaagcc gttatggtca ctggggcggg aggctcgatc ggctctgagc tttgtcgtca   12840
aattgttcga tataagccgg ccaaattggt tctatttgaa ctgtctgaat atgccctcta   12900
cgctattgag aaagagctct cggcgctgtg cgacaaagaa gttttgaatg ttccagtgat   12960
ccctctgttg ggctcggtgc agcgtcagaa tcgcttacag atggtgatga agtcctttgg   13020
tattcaaacg gtttatcatg cggccgctta taaacatgtg cctctggttg agcataatgt   13080
ggtggaaggg gtacgtaata acgtgtttgg taccttgtac tgcgctgagt cagcgatcga   13140
aagtggcgtt gaaactttg tgttgatttc caccgataaa gcggtgcgcc cgaccaacac   13200 tatgggaca actaagcgtc tggccgaatt ggtattgcag gctttgtctg cacggcaaag   13260
ccaaactcgc ttttgtatgg tgcgatttgg taatgtactc ggttcttcgg gctctgtcgt   13320
gccgttgttt gaaaaacaga ttgcccaagg tgggccagtt accttgactc atcgtgacat   13380
tattcgctat ttcatgacaa ttccggaagc atcacagttg gtgattcaag cggggcgat   13440 ggggcatggc ggcgatgtct ttgtcttaga catgggcgat ccggtcaaga tttatgactt   13500
agccaaacgc atgatccggt taagtggctt gagtgtacgg gatgataaaa atccagatgg   13560
cgatattgcc attgaagtta cgggattacg tccaggggag aaactgtatg aagaattact   13620
gattggtgat tcagttcaag gtacctctca tccacgaatt atgacggcca acgaagtgat   13680
gctaccgtgg caggatctat cgctcttact taaagagctg gatcaagctt gtcatgactt   13740
tgatcatgag cgaattcgca gtttgttgtt acaagcacca gcggcattca atccaactga   13800
tgatatttgc gatctagttt ggcagcagaa aaaatcgctg ttatcacaag cgagcaatgt   13860
cattcgcctg tgattgctta ggtttaacct tccacaccaa ttcttcacct ctcttacaaa   13920
tccccgctag gcggtacatc gtgaccgcct ttagcctgat gcctgctctt aacaaacag   13980 gacatcagtg tatgtttaaa cctttagcg ccgaatttt cggcactttc tggctggttc   14040
tgggtggctg tggtagcgcc ttgatctctg ctgctttccc acagttaggt ataggctttt   14100
tgggcgtggc gttggcgttt ggtctgacag tagtcaccat ggcttatgcg gtcgggcaca   14160
tctctggtgc gcattttaac cccgcggtga ccttgggtct gtgggccggt ggacgcttcc   14220
cagcagcgcg cgtgttacct tacattatcg ctcaggttat cggcggtatt gccgctgcgg   14280
cagtgctgta tggtatcgcc agcggtaagg ctgggtttga tgcgacaacc agcggttttg   14340
```

```
cggctaatgg ttatggcctc cattcacctg gcggctatgc gttaagcgcc tgtatgctga    14400
gcgagtttgt cctcagtgcg tttttttgtcc ggagcgacag aaaaacgcgc tcctgcgggc    14460
tttgcgccac tggcgattgg tctggtaatc accccgtaaa ttaaccagcg tcaaaagtag    14520
aattttctcg taccataaac gcaggagatt ctttatgcaa acatcaaaat ttaccgacaa    14580
gcaaatcatg gcgatcctca aatgaacccc cccgggaatc ctggagacta aacttcctga    14640
gaaagaggta aacaggatga ctaaaaatac tcgttttttcc cccgaagtcc gtcaacgggc    14700
agtccgtatg gttctggaaa gtcagggcga atatgactca caatgggcga caatttgttc    14760
cattgctcca aagattggct gtacgccgga gactctgcgt gtccgggttc gccagtatga    14820
gcgggatacc gggggcggtg atggagggct caccaccgct gaacgtcagc gtctgaaaga    14880
gctggagcgt gaaaatcgtg aactgcgccg cagtaacgat atccttcgcc aagcttccgc    14940
ttattttgcg aaggcggagt tcgaccgcct ctggaaaaaa tgatgccact gctggataag    15000
ctgcgtgagc agtacggggt cggaccgcta tgcagcgaac tgcatattgc cccgtcaacg    15060
tattagggat ttgaagccca accgtacgaa aacgtacgct aagttcattt cttgaacaac    15120
ctggctgact ctatgtattt gtacagcgtt ggcctcgata tccccatcaa cacacaaatc    15180
tgcgcaactg tatgttttt ctcgttatag agttgaacag caagggcctg tttatcctta    15240
ctcagtgttt tcggcctgcc gcccttacgt cctctggctc gtgctgcttg aagcccgacc    15300
tgagttctct ctcttgtcag gttgcgttca tcgataggaa ttaaaacccc aaaaagatta    15360
aaaaaacacc acaaaacgga tgtttcttca acaccacttt tgctccatat gaacggaacc    15420
gacgattaaa ctggatggct ctgattgatt cagggtatga atggcggttt tttgctccgt    15480
ttccctcaaa atgacgcaa cttcccctct gcggctctca gccgcaccac cgcatccggg    15540
ccaagcagct catgcatcag gacctgctct gccagacggt agccccgctt cagcccgta    15600 aaacgcatct gactcccgca cagcacgcac ttcagcgggt caaccttcag taacctctga    15660
tacatccctc tccaggtgat ttgcatcgcc gttttttctca ctgtctccgt tatgatgtac    15720
accacttctt ccagtaaccg ccgtttcgcc ggactcaaaa aaccgtagta cctcaccata    15780
cggaacccct tatccgccac atgccaggag aaccttttcca tgaactcatc tccactcatc    15840
aacaggtatt cttcccgttt tgttcggtga ctgttgtaac gcagaccgat ttcatcctga    15900
ccggcataat gctccagacg actcatcggc actggtggct ttttcaggta agagccaaag    15960
tacaccgcca catgggtggc attatccatc acccgggata cgttgacatt ccagccacgg    16020
cggtaatgcg tgtccaggaa gcgattccat tcccgtttac tgcttccttc tgctgccagc    16080
gcatccggca tcaccaggtc agggtatttc cgtgacagca accgtgttat ccggtagcgc    16140
cacatgctca tcaccttacg ggcgtaaaaa tgaagatttt tccaggtgtg gcccgacgtc    16200
acaccaccgg cagttgtcga taaatggata tgcggatgcc actgctggtc acgcccccat    16260
gtgtggatca ccgtgaatat ccccgactcc acatctgcct gatggcagat ttccagtatc    16320
acatccgctg caatgcggct catctctgtc agtaaccacc ggttgtggaa caccagggac    16380
cagtactggc agggaagtgt gaacacaata tgctgccacg ggcagtcggg gaccaggctc    16440
agcagatact gtatccactg tgcgccagcc ttcaccccgc agtgcgggca ggagcggctt    16500
ttacaccgga agcagacctt ttttgtatgg caacagtccg gtgatgaaca gcaccactgt    16560 gtataccccca tcagtgtggt cccgcacgcc atgattttgg tcaccgactc aatcaccacc    16620
ggacgtactg ccccttccgg ctgcttctcc agccagttaa gccagcggtt tccctgctga    16680
aagatatcgg caaaacgggg aagcatcaga agggcggggc gactccgtcc ggccagtgaa    16740
```

-continued

```
ccgtgccaca ctccgggcag tacataccgc cggcgctgat accgaaaaga atggtcgcaa    16800
attcccgctc cgtgcagcgg gcgatttccg gatacccttc gtcatcaaca cgtacaaacc    16860
agaagaccag cttttttgttt cccgcatcca caaagaacgg aatattcagg tctgcgcagc    16920
attcaacggc atcgtcaaaa ctatcaaagc gcagaacttc tgcgtcttct tcgtcaaaaa    16980
aatcatcttc gtgaagcttc acgacatagc ggggaagttt gcttctttga gaggcgggtt    17040
tacgtttacg gggtttagct gaacgggcca tataaccacc acctgaaaga caatgacatt    17100
gcctgttttt ataacggtaa ttgcagacca tgacaagccg cagccgtcag gctgcctact    17160
cgggggttca tcgcagcagc tacagatact ggaaaaaccg tcctgaaaaa ccagacggca    17220
gacgggctgt attacgcagt caggtacttg agctacatgg catcagccac ggttcggccg    17280
gagcaagaag catcgccaca atggcaaccc ggagaggcta ccagatggga cgctggcttg    17340
ctggcaggct catgaaagag ctggggctgg tcagctgtca gcagccgact caccggtata    17400
aacgtggtgg tcatgaacat gttgctatcc ctaactacct tgaaaggcag ttcgccgtga    17460
ccgagccaaa tcaggtgtgg tgcggtgatg tgacctatat ctggacgggt aagcgctggg    17520
cgtacctcgc cgttgttctc gacctgttcg caagaaaacc agtgggctgg gccatgtcgt    17580
tctcgccgga cagcaggctc accatgaaag cgctggaaat ggcatgggaa acccgtggta    17640
agcccggcgg ggtgatgttc cacagcgatc agggcagtca ttatacgagc aggcagttcc    17700
ggcagttatt gtggcgatac cagatcagac agagtatgag ccggcgcgga aactgctggg    17760
ataacagccc aatggaacgc ttcttcagga gtctgaagaa cgaatggatg ccgatggtgg    17820
gttacgtaag cttcagagag gcagctcacg ccataacgga ctatatcgtt ggatattaca    17880
gcgcactaag accgcacgaa tataacggtg ggttacccccc aaacgaatcg gaaaatcgat    17940
actgaaaaaa ctctaactcg gtggccagtt tttgttgacc acttca                   17986
```

<210> SEQ ID NO 8
<211> LENGTH: 2964
<212> TYPE: DNA
<213> ORGANISM: Shigella sonnei
<220> FEATURE:
<223> OTHER INFORMATION: GenBank Accession No. AF455358, Shigella sonnei
      strain 53G Wzz (wzz) complete CDS

<400> SEQUENCE: 8

```
tgatgccatt ttatttcagg aaggaggtcc gttaaactca ggctacctca cggaatattc     60
agggtctgcg cagcattcaa cggcatcgtc aaaactatca aagcgcagaa cttctgcgtc    120
ttcttcgtca aaaaaatcat cttcgtgaag cttcacgaca tagcggggaa gtttgcttct    180
ttgagaggcg ggtttacgtt tacgggtttt agctgaacgg ccatataac cacctgaaag    240 acaatgacat tgcctgtttt tataacggta attgcagacc atgacaagcc gcagccgtca    300
ggctgcctac tcgatcagcc tgctgaagcg gcttaaagcg cataccgtc gggcgaaaac    360 catcacgctg atcgtggaca actacattat ccacaaaagc cgggaaacac agagctggct    420
gaaggagaac ccgaagttca gggtcattta tcagccggtt tactcgccat gggtgaacca    480
tgttgaacgg ctatggcagg cacttcacga cacaataacg cgtaatcatc agtgcagctc    540
aatgtggcaa ctgttgaaaa aagttcgcca ttttatggaa accgtcagcc cattccccgg    600
aggcaaacat gggctggcaa aagtgtagcg gtattaagcg cagctagttt agcctcacag    660
aatttacaaa catacttgtt atcatttga aggcagattt ggtcttatac aggcattgct    720
ttataatctg cactccaaat tctgcgggct atccgccggt ttgcagcagg gaagtgtggg    780
```

```
actgtatatg tctcttcaca cggagtgttc tcgattatgt cctctaatcc cagatatcac    840
ttgttgtatc gcagttggct atatcctgtt tctgcgcagc gctttgggag ctgaaactca    900
agggcggtag cgtactttt tgtcaggctt attcttcatt tttattttta acccattgat     960
aaataatgga ttggtttcat gtcaaaagca tctgaaccac aacagacccc ttatctgatc   1020
ccgcaagggg tctatccaac ttatatgcca aaagcagagg atgaaatcga tcttttcgag   1080
cttttaggca ccttgtggaa gaaaaaatgg gttattttat gtgtcacgtt gctgactacg   1140
gggttagcag cagtgtatgc ctttaccgca aaagagcagt ggacggctaa aacctatatt   1200
caagcaccac gtattgctga attaggcagc tatcttaaat ttcaccaagc gtatgcccga   1260
atattaaatc aaccgttaga tacgaatgcg ttggctaatg gattgttttc cgatttgatt   1320
ttgattgctg aatcgccaga caccaaagtt aaatttctag agagtactga gtattataaa   1380
aaggaaacaa ataatttatc tactgaacaa gataagaaaa tttggttagc tgagcaagcg   1440
aataaaggtc ttgtgattac gccaccaaag gaaaagggaa atacaagtta ctacataata   1500
caagcatcgg cagactcagc gcaagaggca tataaactac tgcagggata tctaaagaat   1560
gttaataatc aagctgtaac attaagtctt gatgagtttg gtcaaaatgt taatactctt   1620
ttggttaatc taaataaaga aatcattgac atagatttcc agagaaaatc agaaaagctt   1680 gatcaaaatag ctcatattca gcgagattta acaactgcgg aacaagccgg aatcattgat   1740
tatcgctcta gcaaaggcgg cttcgataat gcgcaaagta gctataagtt cttgctcggc   1800
gaaaaactgt tatcagcaga gctaaaagca actaaagatg cgccaattat ttacccattt   1860
agatattacg aagtgaaacg tcaaattgat gagttagaag gaatgttacg cgataacatt   1920
caggcgcaag catatcgata tcaaatgaag ccatctgagc cagttataaa agacaaaccc   1980
aacaaagcat taatttttgat tcttggtgca ttaccagggg caatgtttgc tatagttggt   2040
acattagttt atgcgacatt aaaagataaa accaagttag attaaactgg gttacgtatt   2100
gttgtgtcaa tgcgaaatag atgttctatg tgcactttat gatggataag aaaatgaaat   2160
tcgatacttt gaatgcgaaa attgggatta taggccttgg ttatgttgga ttgcctcttg   2220
ctgttgagtt tggaaagaaa gtaacgacga ttggatttga tattaataag tctcgtattg   2280
atgaattacg aaatggtcac gatagtacat tagagtgctc aaatttagag ttgttagaag   2340
caactaaatt gacgtacgcc tgttcattag atgcactaaa agagtgtaat gtatttattg   2400
taactgttcc agctccaatt gataaacata aacagccaga tctaacacct ctaattaaag   2460
catctgaaac attgggtaag ataataaaga aaggcgatgt tattattat gagtcaacag   2520 tttaccctgg agcgacagaa gaagattgta taccagttgt agagaaagta tcaggtctta   2580
agtttaatat tgattttttt gccggttatt cacctgagcg tattaatcct ggggataaag   2640
agcatcgtgt aactaatatc cttaaggtgg ccagtggatc tacaccggat gttgctgagt   2700
atgtagatca gctatataaa ttaataatta ctgtcggtac gcataaagca tcatcgataa   2760
aagtagagag gctgcaaagt aatgtaaaca cgcagcgaga tgtcaatatt gcattgatta   2820
atgagttatc tattatattt aataagttag ggattgatac cttagaggtt cttgaggctg   2880
caggtacgaa gtggaatctt ttacctttta ggcccggttt agtaggtggc cactgtatag   2940
gtgtagatcc ttattatctt acac                                         2964
```

<210> SEQ ID NO 9
<211> LENGTH: 2069
<212> TYPE: DNA
<213> ORGANISM: Shigella sonnei
<220> FEATURE:
<223> OTHER INFORMATION: 2.1 kb HindIII fragment from AF294823 (SEQ ID
      NO:7 positions 14931-16999), obtained from Shigella sonnei O
      antigen gene cluster

<400> SEQUENCE: 9

```
aagcttccgc ttattttgcg aaggcggagt tcgaccgcct ctggaaaaaa tgatgccact     60
gctggataag ctgcgtgagc agtacggggt cggaccgcta tgcagcgaac tgcatattgc    120
cccgtcaacg tattagggat ttgaagccca accgtacgaa acgtacgct aagttcattt     180
cttgaacaac ctggctgact ctatgtattt gtacagcgtt ggcctcgata tccccatcaa    240
cacacaaatc tgcgcaactg tatgtttttt ctcgttatag agttgaacag caagggcctg    300
tttatcctta ctcagtgttt tcggcctgcc gccttacgt cctctggctc gtgctgcttg     360
aagcccgacc tgagttctct ctcttgtcag gttgcgttca tcgataggaa ttaaaacccc    420
aaaaagatta aaaaacacc acaaaacgga tgtttcttca acaccacttt tgctccatat     480
gaacggaacc gacgattaaa ctggatggct ctgattgatt cagggtatga atggcggttt    540
tttgctccgt ttccctcaaa atggacgcaa cttcccctct gcggctctca gccgcaccac    600
cgcatccggg ccaagcagct catgcatcag gacctgctct gccagacggt agcccgcctt    660
cagccccgta aaacgcatct gactcccgca cagcacgcac ttcagcgggt caaccttcag    720
taacctctga tacatccctc tccaggtgat ttgcatcgcc gttttctca ctgtctccgt     780
tatgatgtac accacttctt ccagtaaccg ccgtttcgcc ggactcaaaa accgtagta    840
cctcaccata cggaacccct tatccgccac atgccaggag aaccttttcca tgaactcatc    900
tccactcatc aacaggtatt cttcccgttt tgttcggtga ctgttgtaac gcagaccgat    960
ttcatcctga ccggcataat gctccagacg actcatcggc actggtggct ttttcaggta   1020
agagccaaag tacaccgcca catgggtggc attatccatc acccgggata cgttgacatt   1080
ccagccacgg cggtaatgcg tgtccaggaa gcgattccat tcccgtttac tgcttccttc   1140
tgctgccagc gcatccggca tcaccaggtc agggtatttc cgtgacagca accgtgttat   1200
ccggtagcgc cacatgctca tcaccttacg ggcgtaaaaa tgaagatttt tccaggtgtg   1260
gcccgacgtc acaccaccgg cagttgtcga taaatggata tgcggatgcc actgctggtc   1320
acgcccccat gtgtggatca ccgtgaatat ccccgactcc acatctgcct gatggcagat   1380
ttccagtatc acatccgctg caatgcggct catctctgtc agtaaccacc ggttgtggaa   1440
caccagggac cagtactggc agggaagtgt gaacacaata tgctgccacg ggcagtcggg   1500
gaccaggctc agcagatact gtatccactg tgcgccagcc ttcaccccgc agtgcgggca   1560
ggagcggctt ttacaccgga agcagacctt ttttgtatgg caacagtccg gtgatgaaca   1620
gcaccactgt gtataccca tcagtgtggt cccgcacgcc atgattttgg tcaccgactc     1680
aatcaccacc ggacgtactg ccccttccgg ctgcttctcc agccagttaa gccagcggtt   1740
tccctgctga aagatatcgg caaaacgggg aagcatcaga agggcggggc gactccgtcc   1800
ggccagtgaa ccgtgccaca ctccgggcag tacataccgc cggcgctgat accggaaaga   1860
atggtcgcaa attcccgctc cgtgcagcgg gcgatttccg gataccctc gtcatcaaca    1920
cgtacaaacc agaagaccag cttttttgttt cccgcatcca caaagaacgg aatattcagg   1980
tctgcgcagc attcaacggc atcgtcaaaa ctatcaaagc gcagaacttc tgcgtcttct   2040
tcgtcaaaaa aatcatcttc gtgaagctt                                     2069
```

-continued

<210> SEQ ID NO 10
<211> LENGTH: 1212
<212> TYPE: DNA
<213> ORGANISM: Shigella sonnei
<220> FEATURE:
<223> OTHER INFORMATION: 1.2 kb HindIII fragment from AF294823 (SEQ ID NO:7 positions 13725-14936) obtained from Shigella sonnei O antigen gene cluster.

<400> SEQUENCE: 10

```
aagcttgtca tgactttgat catgagcgaa ttcgcagttt gttgttacaa gcaccagcgg     60
cattcaatcc aactgatgat atttgcgatc tagtttggca gcagaaaaaa tcgctgttat    120
cacaagcgag caatgtcatt cgcctgtgat tgcttaggtt taaccttcca caccaattct    180
tcacctctct tacaaatccc cgctaggcgg tacatcgtga ccgcctttag cctgatgcct    240
gctctttaac aaacaggaca tcagtgtatg tttaaacctt ttagcgccga atttttcggc    300
actttctggc tggttctggg tggctgtggt agcgccttga tctctgctgc tttcccacag    360
ttaggtatag gctttttggg cgtggcgttg gcgtttggtc tgacagtagt caccatggct    420
tatgcggtcg ggcacatctc tggtgcgcat tttaaccccg cggtgacctt gggtctgtgg    480
gccggtggac gcttcccagc agcgcgcgtg ttaccttaca ttatcgctca ggttatcggc    540
ggtattgccg ctgcggcagt gctgtatggt atcgccagcg gtaaggctgg gtttgatgcg    600
acaaccagcg gttttgcggc taatggttat ggcctccatt cacctggcgg ctatgcgtta    660
agcgcctgta tgctgagcga gtttgtcctc agtgcgtttt ttgtccggag cgacagaaaa    720
acgcgctcct gcgggctttg cgccactggc gattggtctg gtaatcaccc cgtaaattaa    780
ccagcgtcaa aagtagaatt ttctcgtacc ataaacgcag gagattcttt atgcaaacat    840
caaaatttac cgacaagcaa atcatggcga tcctcaaatg aacccccccg ggaatcctgg    900
agactaaact tcctgagaaa gaggtaaaca ggatgactaa aaatactcgt ttttcccccg    960
aagtccgtca acgggcagtc cgtatggttc tggaaagtca gggcgaatat gactcacaat   1020
gggcgacaat ttgttccatt gctccaaaga ttggctgtac gccggagact ctgcgtgtcc   1080
gggttcgcca gtatgagcgg gataccgggg gcggtgatgg agggctcacc accgctgaac   1140
gtcagcgtct gaaagagctg gagcgtgaaa atcgtgaact gcgccgcagt aacgatatcc   1200
ttcgccaagc tt                                                       1212
```

<210> SEQ ID NO 11
<211> LENGTH: 1405
<212> TYPE: DNA
<213> ORGANISM: Shigella sonnei
<220> FEATURE:
<223> OTHER INFORMATION: 1.4 kb XbaI-HindIII fragment from AF294823 (SEQ ID NO:7 positions 12326-13730) obtained from Shigella sonnei O antigen gene cluster.

<400> SEQUENCE: 11

```
tctagattgc tttttagaat gatacttaac tatggagtta agggtagtgc gcctgttttg     60
atttatggcg ctggtgaatc tggccgacaa ttattgccag cattaatgca ggcaaaagaa    120
tattttcctg tggcatttgt ggatgataat cctcgcttgc ataaggctgt cattcatggt    180
gtaacagttt atccctcgga taaactgagt taccttgtag atcgctatgg tataaagaaa    240
attcttttgg cgatgccgag cgtcagtaag tcacaaaggc agaaagtgat tactcgttta    300
gagcatctac cgtgtgaagt tctctctatt ccgggtatgg tcgatttagt cgaaggtcga    360
gcacaaatca gtaatctaaa aaaagtatcg attgatgact tactaggtcg tgatccggtt    420
```

-continued

```
gctcctgatg ccaaattgat ggccgaaaac attactggca aagccgttat ggtcactggg    480
gcgggaggct cgatcggctc tgagctttgt cgtcaaattg ttcgatataa gccggccaaa    540
ttggttctat ttgaactgtc tgaatatgcc ctctacgcta ttgagaaaga gctctcggcg    600
ctgtgcgaca aagaagtttt gaatgttcca gtgatccctc tgttgggctc ggtgcagcgt    660
cagaatcgct tacagatggt gatgaagtcc tttggtattc aaacggttta tcatgcggcc    720
gcttataaac atgtgcctct ggttgagcat aatgtggtgg aaggggtacg taataacgtg    780
tttggtacct tgtactgcgc tgagtcagcg atcgaaagtg gcgttgaaac ttttgtgttg    840
atttccaccg ataaagcggt gcgcccgacc aacactatgg ggacaactaa gcgtctggcc    900
gaattggtat tgcaggcttt gtctgcacgg caaagccaaa ctcgcttttg tatggtgcga    960
tttggtaatg tactcggttc ttcgggctct gtcgtgccgt tgtttgaaaa acagattgcc   1020
caaggtgggc cagttacctt gactcatcgt gacattattc gctatttcat gacaattccg   1080
gaagcatcac agttggtgat tcaagcgggg gcgatgggc atggcggcga tgtctttgtc    1140
ttagacatgg gcgatccggt caagatttat gacttagcca aacgcatgat ccggttaagt   1200
ggcttgagtg tacgggatga taaaaatcca gatggcgata ttgccattga agttacggga   1260
ttacgtccag gggagaaact gtatgaagaa ttactgattg gtgattcagt tcaaggtacc   1320
tctcatccac gaattatgac ggccaacgaa gtgatgctac cgtggcagga tctatcgctc   1380
ttacttaaag agctggatca agctt                                         1405
```

<210> SEQ ID NO 12
<211> LENGTH: 27
<212> TYPE: DNA
<213> ORGANISM: Shigella sonnei
<220> FEATURE:
<223> OTHER INFORMATION: promoter consensus sequence of AF294823 (SEQ ID
    NO:7 positions 1645-1671), promoter and operator sequence
    immediately upstream (5') of wbgT gene

<400> SEQUENCE: 12

```
attaccaggg gcaatgtttg ctatagt                                          27
```

<210> SEQ ID NO 13
<211> LENGTH: 20
<212> TYPE: DNA
<213> ORGANISM: Shigella sonnei
<220> FEATURE:
<223> OTHER INFORMATION: transcription terminator sequence of AF294823
    (SEQ ID NO:7 positions 13930-13949), immediately
    downstream (3') of wbgZ gene

<400> SEQUENCE: 13

```
ggcggtacat cgtgaccgcc                                                  20
```

<210> SEQ ID NO 14
<211> LENGTH: 38
<212> TYPE: DNA
<213> ORGANISM: Shigella sonnei
<220> FEATURE:
<223> OTHER INFORMATION: JUMPstart sequence of AF294823 (SEQ ID NO:7
    positions 877-914)

<400> SEQUENCE: 14

```
cagcgctttg ggagctgaaa ctcaagggcg gtagcgta                              38
```

<210> SEQ ID NO 15
<211> LENGTH: 1032
<212> TYPE: DNA
<213> ORGANISM: Shigella sonnei
<220> FEATURE:
<223> OTHER INFORMATION: transposable element IS630 sequence of AF294823
      (SEQ ID NO:7 positions 6894-7925)

<400> SEQUENCE: 15

| | | | | | |
|---|---|---|---|---|---|
| atgccgatca | tagcaccaat | ttcccgtgac | gaacgacgcc | tgatgcagaa | agccatccat | 60 |
| aaaacacacg | ataaaaatta | tgcccgcaga | ctgactgcca | tgctgatgct | gcaccggggc | 120 |
| gaccgtgtca | gcgacgttgc | cagaacgctc | tgctgcgccc | gttcctctgt | tggacgctgg | 180 |
| attaactggt | tcacgcagtc | gggtgttgag | ggactgaaat | cattacctgc | cgggcgtgcc | 240 |
| cgtcgctggc | cgtttgagca | tatctgcaca | ctgttacgtg | agctggtaaa | acattctccc | 300 |
| ggcgactttg | gctaccagcg | ttcacgctgg | agtacagaac | tgctggcaat | aaaaatcaat | 360 |
| gagataaccg | gttgccagtt | aaatgccgga | accgttcgcc | gctggttgcc | gtctgcgggg | 420 |
| attgtgtggc | gaagggctgc | gccaactctg | cgtatccgtg | accgcataa | agatgaaaag | 480 |
| atggcagcaa | tccataaagc | actggacgaa | tgcagcgcag | agcatccggt | cttttatgaa | 540 |
| gatgaagtgg | atatccatct | taatcccaaa | atcggtgcgg | actggcaact | gcgcggacag | 600 |
| caaaaacggg | tggtcacgcc | gggacagaat | gaaaaatatt | atctggccgg | agcgctgcac | 660 |
| agcgggacag | gtaaagtcag | ctgtgtgggc | ggcaacagca | aaagttcggc | gctgttcatc | 720 |
| agcctgctga | gcggcttaa | agcgacatac | cgtcgggcga | aaaccatcac | gctgatcgtg | 780 |
| gacaactaca | ttatccacaa | aagccgggaa | acacagagct | ggctgaagga | gaacccgaag | 840 |
| ttcagggtca | tttatcagcc | ggtttactcg | ccatggatga | atcatgttga | acggctatgg | 900 |
| caggcacttc | acgacacaat | aacgcgtaat | catcagtgca | gctcaatgtg | gcaactgttg | 960 |
| aaaaaagttc | gccatttat | ggaaaccgtc | agcccattcc | ccggaggcaa | acatgggctg | 1020 |
| gcaaaagtgt | ag | | | | | 1032 |

<210> SEQ ID NO 16
<211> LENGTH: 13660
<212> TYPE: DNA
<213> ORGANISM: Shigella sonnei
<220> FEATURE:
<223> OTHER INFORMATION: GenBank Accession No. AF285971, Shigella sonnei
      Related Sequences, Shigella sonnei plasmid Pinv O antigen gene
      cluster, complete sequence

<400> SEQUENCE: 16

| | | | | | |
|---|---|---|---|---|---|
| atttttaacc | cattgataaa | taatggattg | gtttcatgtc | aaaagcatct | gaaccacaac | 60 |
| agaccccta | tctgatcccg | caaggggtct | atccaactta | tatgccaaaa | gcagaggatg | 120 |
| aaatcgatct | tttcgagctt | ttaggcacct | tgtggaagaa | aaaatgggtt | atttttatgtg | 180 |
| tcacgttgct | gactacgggg | ttagcagcag | tgtatgcctt | taccgcaaaa | gagcagtgga | 240 |
| cggctaaaac | ctatattcaa | gcaccacgta | ttgctgaatt | aggcagctat | cttaaatttc | 300 |
| accaagcgta | tgcccgaata | ttaaatcaac | cgttagatac | gaatgcgttg | gctaatggat | 360 |
| tgttttccga | tttgattttg | attgctgaat | cgccagacac | caaagttaaa | tttctagaga | 420 |
| gtactgagta | ttataaaaag | gaaacaaata | atttatctac | tgaacaagat | aagaaaattt | 480 |
| ggttagctga | gcaagcgaat | aaaggtcttg | tgattacgcc | accaaaggaa | aagggaaata | 540 |
| caagttacta | cataatacaa | gcatcggcag | actcagcgca | agaggcatat | aaactactgc | 600 |
| agggatatct | aaagaatgtt | aataatcaag | ctgtaacatt | aagtcttgat | gagtttggtc | 660 |

-continued

```
aaaatgttaa tactcttttg gttaatctaa ataaagaaat tattgacata gatttccaga    720
gaaaatcaga aaagcttgat caaatagctc atattcagcg agatttaaca actgcggaac    780
aagccggaat cattgattat cgctctagca aaggcggctt cgataatgcg caaagtagct    840
ataagttctt gctcggcgaa aaactgttat cagcagagct aaaagcaact aaagatgcgc    900
caattattta cccatttaga tattacgaag tgaaacgtca aattgatgag ttagaaggaa    960
tgttacgcga taacattcag gcgcaagcat atcgatatca aatgaagcca tctgagccag   1020
ttataaaaga caaacccaac aaagcattaa ttttgattct tggtgcatta ccaggggcaa   1080
tgtttgctat agttggtaca ttagtttatg cgacattaaa agataaaacc aagttagatt   1140
aaactgggtt acgtattgtt gtgtcaatgc gaaatagatg ttctatgtgc actttatgat   1200
ggataagaaa atgaaattcg atactttgaa tgcgaaaatt gggattatag ccttggtta    1260
tgttggattg cctcttgctg ttgagtttgg aaagaaagta acgacgattg gatttgatat   1320
taataagtct cgtattgatg aattacgaaa tggtcacgat agtacattag agtgctcaaa   1380
tttagagttg ttagaagcaa ctaaattgac gtacgcctgt tcattagatg cactaaaaga   1440
gtgtaatgta tttattgtaa ctgttccaac tccaattgat aaacataaac agccagatct   1500
aacacctcta attaaagcat ctgaaacatt gggtaagata taaagaaag gcgatgttat   1560
tatttatgag tcaacagttt accctggagc gacagaagaa gattgtatac cagttgtaga   1620
gaaagtatca ggtcttaagt ttaatattga ttttttttgcc ggttattcac ctgagcgtat   1680
taatcctggg gataaagagc atcgtgtaac taatatccct aaggtgacca gtggatctac   1740
accggatgtt gctgagtatg tagatcagct atataaatta ataattactg tcggtacgca   1800
taaagcatca tcgataaaag tagcagaggc tgcaaaagta attgaaaaca cgcagcgaga   1860
tgtcaatatt gcattgatta atgagttatc tattatatt aataagttag ggattgatac   1920
cttagaggtt cttgaggctg caggtacgaa gtggaatttt ttaccttta ggcccggttt   1980
agtaggtggc cactgtatag gtgtagatcc ttattatctt acacataaag cgcaaagtgt   2040
cggctatcat ccggagatga ttttagccgg acgtcgttta aatgatagta tggggcagta   2100
tgtcgtttcc cagttagtca aaaaaatgtt gaaacaacgg attcaagttg aagggcgaa    2160
tgtgttagtg atgggggctta catttaaaga gaattgccca gatctacgaa acactaaagt   2220
gattgatatt atttcagagt taaaagaata caatatcaat atagatatta tagatccatg   2280
gtgttctacc gatgaggcac aacatgaata tggattaact ttatgtgaag atcctaaagt   2340
taatcattat gatgcaataa ttatcgctgt tgcacacaat gagtttgcg agatgggaga    2400
gagcgctatt cgtgcattag gtaaagacga gcacgttttg ttcgatttaa aatatgtgct   2460
tgataaaaaa agtatcgata tgcgcttgta agagtgatta aaaaaatcaa atcctctttg   2520
atatgataca cctcagcatt ttatgctagg tttagcactt gattaatata catggatatt   2580
tatatgtctc gctatgaaga gattacacag cagttaattt tttcaccgaa aacttggtta   2640
attactggtg tcgctggctt tataggatca aatcttttag aaaagttact taaattaaac   2700
caggttgtta ttgggttaga taacttttcc acgggacatc aatataatct tgatgaagtt   2760
aaaacattag tttccactga acagtggagt cgattttgct ttatagaagg tgatattcga   2820
gatctcacta cctgtgagca agttatgaaa ggtgttgatc atgtcttaca tcaggctgcg   2880
ctaggttctg tacctcgttc aattgttgat cctataacaa ccaatgcaac taatattact   2940
ggattttga atatcttaca tgcggctaaa aatgcacaag tacaaagttt tacttatgct   3000
gcatcaagct caacttatgg agatcatccc gcactaccaa aagtagagga aaacattggt   3060
```

```
aatccacttt ctccttatgc agttactaaa tatgttaacg agattatgc tcaggtatat    3120 gctcgaacat atggtttaa aactattgga ttacgttatt ttaatgtatt tggtcgtcgt    3180
caagatccta atggagctta tgctgcagta attccaaaat ggacagcagc aatgcttaaa    3240
ggtgatgacg tatatattaa tggcgatggt gaaacgagtc gtgattttg ttatatagat    3300 aatgttatac aaatgaatat attatctgca ttagcgaagg acagtgctaa agataatata    3360
tataatgttg cagttggtga tagaacaacg ttaaatgaat tatctggtta catttatgat    3420
gagcttaatt taattcacca tatcgataaa ttgagcatta agtatagaga gtttagatct    3480
ggagatgtta ggcattctca ggctgatgtt actaaggcta tagatttact aaagtataga    3540
ccaaatataa aaatcagaga gggattacga ctttcaatgc cgtggtatgt gagatttta    3600 aaaggctaaa ttatattaac atgaataaat aatctatttc acctctgtta ttaatgcagg    3660
ggtgaaaatc catgtattta ttctaaatgg tcagtgtatg tttagaaaaa tgattgatgc    3720
aggtggtaca ttttactta aagcaatatt tcaaatagga gttttgttt atttcacaca     3780 tgtgtcagat attactacat ttggtattat tagttatgtg tttactgttt attggtttgt    3840
gcttaacttc tctgattatg gatttagaac aaaattagtg aaagatattt ctgataatag    3900
ttattctgca tcagaattat tatcaagaag tgatggagtt aaaacatatg ctttttttctt    3960 cattttata atcttcatgt tttattctta tgtttctgat tcaatttcat taactctgct    4020
tgtttatatt tcatctgcat attttgtttg tatttcaagt ggtagattta gcttgctaca    4080
ggctgttggt cggtttagat gtgaattata tataaatatc tactcaacaa ttatatatat    4140
tgggtgtaat ttattttttat ctctgtttat cgaacctcta tattatagtg cgatatcaat    4200
attcatatac tcaatttcgc ttttggtttt ctcatcacat aaatgcaatg tgccatgttt    4260
tcatataaaa agaccaagta ttttagttta taaagatttt ttggatgcaa ctccgttcgc    4320
tattctggtg ttactaaatg ttgttttatc tagtattgac cttttttatat taaaagaata    4380 tttctcttat aatagtgttg ctatatatca ggtggtaact agggttaata ccggtctaat    4440
aatagtgttt aatgttattt atactgtttt attgccttca ttttcttatt atctgaaaaa    4500
ttctgaatgg ggtaatataa ggaaattaca acgatatata tcactgttag tcttattact    4560
atgtttatgc tattattttt ttggcatcta tttcgtaggg atattgtttg gtgatgagta    4620
taaggtaata tcttctgcaa cattttttgat aatgtttatg gctcttatta aatataattt    4680
ttggctaata aatgaacttt atcttgtgtg tagtggaaat caaagcgagc gagttaaatc    4740
gtattgtatt ggtgtggtca tttcaatggc ggttttcttt tattttatac ctcggtatgg    4800
atggagtggg gcggttttg gaagtgccat tgcaacatta gtaattggaa tattttatat    4860
tatttctgtg aaaaaagatt gtgggaaaat tcttcatgat aagtattcac taatgatgat    4920
ctttgtccca attttctttt attttattat taatggtcag cagcggttgt tatattaata    4980
tgttgtggtt ttatatcgtt ccattaatat gtttagactc gattgaaagc ctaataaagg    5040
ttaagtatgt taatatacct atatcctgta cttttgttat ttaatatcct tccggttttt    5100
ttttatggac aaatgaactc tgatttagag cgttttttg gagttcctat tggctatatt    5160
ccagatctaa tattttattt ctttgttgtt ttaacatcta taataacgtt gaggtttcac    5220
gtttctctgt ggacaaagaa attattattt ttaggcatca tattcctgat ttatatcagc    5280
attcagatgt tgttgttatc agcggatata tcaggtgtcg taatttatt atcgtttttt    5340 tctaatttta tagcttttggt tcttttggtg tcatttgca ttggtaaaga tgagcttat    5400 ttaactcatt cggttagaaa tataaatgtt gtaatgtgtt ttggtattat ctgtggagtt    5460
```

```
gtaaaattat ttattggtta ttctgaagat agtaatttta tagtttattt aaatagaaat   5520
gccaccgcaa ttatagtagt gtgcttttat tgtgtatatt catacttttta tcgtggtcga   5580 aagtcttggt atgtctcatc tgtattgtac tctctgttct ttcttttttct ggatagccga   5640 gcaggaataa tatcatttgc tatatcgttg ttttttgttt ttcttcagtt aacaaagaag   5700
gaaaagttat taatatcatt gttttttgtt cctcttctaa ctttaggtat ttcttttact   5760
gatataggca ctcgtcttga acgaatgctg tcttcgtcac aggttatatt ctctggtggt   5820
aacactctta caaaaagtca gaatgattat cgtcgagttg agttagtatt tattggggtt   5880
gatgttttaa aagaaaatta tttaattggc actggattag gtgttgcaaa ttatgtaaag   5940
gctatagata aaaagttttt aggaagtacc aactttgggt tggcgcataa ttttttattta  6000 tcttattcgg ctcagttagg gattattggt tttattttgc ttatttctgt attttatata   6060
atgctgtctc caatttttaa atgcggaggg tatattggta aaggatgcgt ttttgctttg   6120
gctttctatg tctttttttaa tgagtatata ttgacgccag cgatatatat ttatatttct   6180
atttttttat cggtggtttt tatacgtaat tctaaatagc tgcgcggaat agtagatcac   6240
tttgagggaa cttagcccgg attgtgcgat ctgatcaatc gccaaatcaa acaaatcac    6300 caaccggact gagcaatgcc gatcatagca ccaatttccc gtgacgaacg acgcctgatg   6360
cagaaagcca tccataaaac acacgataaa aattatgccc gcagactgac tgccatgctg   6420
atgctgcacc ggggcgaccg tgtcagcgac gttgccagaa cgctctgctg cgcccgttcc   6480
tctgttggac gctggattaa ctggttcacg cagtcgggtg ttgagggact gaaatcatta   6540
cctgccgggc gtgcccgtcg ctggccgttt gagcatatct gcacactgtt acgtgagctg   6600
gtaaaacatt ctcccggcga cttttggctac ggttcacgct ggagtacaga actgctggca  6660
ataaaaatca atgagataac cggttgccag ttaaatgccg gaaccgttcg ccgctggttg   6720
ccgtctgcgg ggattgtgtg gcgaagggct gcgccaactc tgcgtatccg tgacccgcat   6780
aaagatgaaa agatggcagc aatccataaa gcactggacg aatgcagcgc agagcatccg   6840
gtcttttatg aagatgaagt ggatatccat cttaatccca aaatcggtgc ggactggcaa   6900
ctgcgcggac agcaaaaacg ggtggtcacg ccgggacaga atgaaaaata ttatctggcc   6960
ggagcgctgc acagcgggac aggtaaagtc agctgtgtgg gcggcaacag caaaagttcg   7020
gcgctgttca tcagcctgct gaagcggctt aaagcgacat accgtcgggc gaaaaccatc   7080
acgctgatcg tggacaacta cattatccac aaaagccggg aaacacagag ctggctgaag   7140
gagaacccga cgttcagggg tcatttatca gcggtttact cgccatggat gaatcatgtt   7200
gaacggctat ggcaggcact tcacgacaca ataacgcgta atcatcagtg cagctcaatg   7260
tggcaactgt tgaaaaaagt tcgccatttt atggaaaccg tcagcccatt ccccggaggc   7320
aaacatgggc tggcaaaagt gtagcggtat taagcgcagc catttaggat gagaatatgt   7380
tgttagaata tgttgaaaga aaatttcct tagccttgag taagtatcct aaggtaaggg    7440
atgttattaa gttctttttat ttatatatcg catcattatt cgcaattatt ttgaataaaa   7500
ataagacggt tattcaatca aaaatatacg agatttcaat tgatgattct gaagaatcat   7560
tttttggcta ttatgaccat agtccaatga gctctaatgg gcggtacgta ttgttccact   7620
ctagtgcgtt tagcactaaa cgacatccaa agaaagttaa gtatatatct atttgcgtaa   7680
aagaccttct taataacaaa gtttataagc tatatgatac gcgagcattt aattggcagc   7740
agggaagccg attaatgtgg attgatgatg acaatataat ttaatgac tatgaaaata    7800 atggatacat tagtgttgtc tattctttgt ctttgatgaa ggttataaaa aaaataaact   7860
```

```
atccgattta tgatgtgaat aattacaagg ctgtgacgtt agatttctca tggctggcta    7920
aatatgatag cgattatggt tattataata aaaaatcatt ttctacagat atttcaatca    7980
ttaatttgaa cacgggggga atagaattat ttttatcctt agacgaaatg ctaaagagaa    8040
ctaattttaa atgtaatatt gatgttgaac atgtggtcaa tcattttatg tttgctcccg    8100
atggacgttc cgttatgttc atacatcgat actatacacc taaaggaaag cgtgaaaggt    8160
taatacattg gaatttaata aatgataatg ttcgagtcct aataaatgaa tcgattatta    8220
gtcattgttg ttggaatggg aatgatgaaa ttataggttt ttttggtgca gaaatagatt    8280
cgctaaatta ttatagattg tcaattgaat cctgtaatac agagaaattg ttttttgatg    8340
caagaaaata ttctgatgga catcctacta tagttcataa tagatatatt atatctgata    8400
cttacccaga taaaaataga attaaaaagt tgtttgttta tgaccttgtc aaaaatgatt    8460
atcgcgagct tggattattt tatgagtcat tgagtttttt ttcttattct cgatgtgact    8520
tacatccaag gatctcggtt gataatagat ttttgtttgt tgattcagtt cactcaggga    8580
aaagaaaact atattttatg aggagtggta tttgtgagtg atgttctagt atctttaatt    8640
atagtttgct ttaatgcaga gaagtatatt gaaaaatctc ttttggcatt tattaatcaa    8700
gatgttggat tagataaatt tgaattgatt attgtagatg gggattcatc tgataataca    8760
atatctattg ttcaggatgt ttttttctaaa catagcaaca ttaagcataa aattatcaat    8820
aataaaaaaa gaactcttgc tacgggttgg aatattgggg tgctagaagc taatggtaag    8880
tttgtgtgta gagttgatgc acatagtgat attccaaata actatatatc taaattatta    8940
gatgattatt ttaatattat gcagtttgat gatagcgttg ttggtgttgg aggtgtatta    9000
actaattctt ataaaactaa gtttggttca attgtagcgg attttatgc atcgaaattt    9060 ggtgttggta attctccatt taggtgcgta gacaaaaata atcgactaaa aaaaacagat    9120
acggctgtct ttgctttata taataaagat gtgtttttg atgttggact ttttaatgaa    9180
gtattagata gaaatcaaga tattgatttt cataagagag ttttaagcaa taatttgtca    9240
ttatatacag ataatagttt atttgttgag tattatgtta gagataattt taaagatttc    9300
ataaagaaag gttttcttga tggttttttgg gttgttatgt ctggagcata ttattttaga    9360
catatagtgc cactttttttt tgttttgtat ttaattgtat cttttttctct tttctttgct    9420 actggtgatt atatatattt atcttttttta ttttttttatt ttcttatttc tattttgttt    9480
tcaattcgag atgggcgaag ttttataggt agagtatttc ttccttttat attttgtct    9540 tatcatattt cttatggatg tggatcgtta ttatcttttt tgaaaaggta ttttaaatga    9600
aaaattttat tcctttttgcg ttacctgaaa ttggcgaaga agaaattgca gaggtaattg    9660
actctttacg ttcaggttgg attacgacag gtcctaaggc taagcaattt gaacaagaat    9720
tttctaatta cctaggagcg aacgttcaat cattagctgt taactctgct acgtcgggct    9780
tacatttggc tcttgaagct gttggcgtaa agccggaga ccaagttatt gtcccatcat    9840
atacattcac tgctactgcc gaaattgtca ggtaccttgg tgctgatcct gtaattgttg    9900
atgtagatcg taaaacattt aatatatcag ttgatgccat tgagaaggct attactaatg    9960
aaacaaaggc gattattcca gtacacttcg ctggattagc ttgtgacatg gattcaatct    10020
tatcaattgc taaaaaatat gacctaaagg ttgtcgagga tgccgctcat gcatttccta    10080
caacatataa aggaagtaag ataggaacgc ttgattcaga tgctacggtt tttagcttct    10140
acgccaataa aactatgaca accggtgaag gcggaatggt tgtttcaaaa aataaagata    10200
taattgagcg ttgtaaggta atgcgtttac atggaatcag tcgtgacgct tttgaccggt    10260
```

```
accagtctaa aactccttct tggttttatg aggttgtagc tccagggttt aaatacaata    10320
tgcctgatat ctgtgcggca atcggtattc atcaacttag aaagatcgat gattttcaga    10380
aaaaacgtca acgaatggca aaaatttacg atgatgcgtt aaaagaattg ccacttgaat    10440
tgcctgaatg gcctactaat gctagtgata ttcatgcttg gcatctatat cctatccgct    10500
taaaaactga ttcggctatt aatcgcgatg attttattaa gaagttatca gatcttggaa    10560
ttggttgttc tgtccatttt ataccgttgc ataagcaacc ggtttggcgt gatacatata    10620
atttgaacgc cagtgacttt ccagtttctg aggagtgtta tttaaatgaa atatctattc    10680
ctctttatac taaaatgacg gatcaagatc agttgttcgt tatcaaatcg attagacaat    10740
tatttatgta atggtatttt atattaaatg aaacgtattt ttgatgttat cgtggcaggc    10800
ttaggcctgc tttttctatt tcctgttttt atcattgtgt caatgttaat tgttgctgat    10860
tctaaagggg gggttttttt taggcagtat agagttggga gatttgggaa agattttagg    10920
atacataaat ttagaacgat gtttatcgat tcagaaaaaa aaggacggat aacagttggt    10980
caagatgctc gggtaaccag agttggatgg tatttacgga agtacaaaat cgatgagctt    11040
cctcaattga tagatgttct ttctggaaca atgagtttgg ttggcccaag accggaagtg    11100
agggagttta ttgatgagta tcctgatgat ataagggaaa aagttttatc ggttaggcca    11160
gggataactg acttagcatc tatagaaatg gtagatgaaa atgagatttt gtctagttat    11220
gatgacccac gtagggctta tatagatata attcttccaa tcaagcaaag atattattta    11280
gattatgttg ctaacaattc agtaaagtat gattgtgtga taatttggaa aactattatt    11340
aagattttgt cgcgataata aggtagtgta ggatgattga tagaatattg gagctgccaa    11400
gaattgttaa gagaggtatc atcatctgca ttgatgtagt tatggtgata ttctcatttt    11460
ggttgtctta ttggttgagg cttgatgagc aaacggcttt tcttagtgca ccgatgtggt    11520
ttgctgcagc tattcttacc atatttaccg tgtttatatt tatcaggatt gggctttatc    11580
gggcagtctt acggtatgtt agtgcaaaga taatgttgct aataccagtt ggtattctgg    11640
cctcaacgtt atctcttgtc gttatatcat attcgctatc cataatgttg ccgcgcactg    11700
ttgtcggaat ttatttttg gttttacttt tactgacatc aggctctaga ttgcttttta    11760
gaatgatact taactatgga gttaagggta gtgcgcctgt tttgatttat ggcgctggtg    11820
aatctggccg acaattattg ccagcattaa tgcaggcaaa agaatatttt cctgtggcat    11880
ttgtggatga taatcctcgc ttgcataagg ctgtcattca tggtgtaaca gtttatccct    11940
cggataaact gagttacctt gtagatcgct atggtataaa gaaaattctt ttggcgatgc    12000
cgagcgtcag taagtcacaa aggcagaaag tgattactcg tttagagcat ctaccgtgtg    12060
aagttctctc tattccgggt atggtcgatt tagtcgaagg tcgagcacaa atcagtaatc    12120
taaaaaaagt atcgattgat gacttactag gtcgtgatcc ggttgctcct gatgccaaat    12180
tgatggccga aaacattact ggcaaagccg ttatggtcac tggggcggga ggctcgatcg    12240
gctctgagct ttgtcgtcaa attgttcgat ataagccggc caaattggtt ctatttgaac    12300
tgtctgaata tgccctctac gctattgaga aagagctctc ggcgctgtgt gacaaagaag    12360
ttttgaatgt tccagtgatc cctctgttgg gctcggtgca gcgtcagaat cgcttacaga    12420
tggtgatgaa gtcctttggt attcaaacgt tttatcatgc ggccgcttat aaacatgtgc    12480
ctctggttga gcataatgtg gtggaagggg tacgtaataa cgtgtttggt accttgtact    12540
gcgctgagtc agcgatcgaa agtggcgttg aaacttttgt gttgatttcc accgataaag    12600
cggtgcgccc gaccaacact atggggacaa ctaagcgtct ggccgaattg gtattgcagg    12660
```

-continued

```
ctttgtctgc acggcaaagc caaactcgct tttgtatggt gcgatttggt aatgtactcg    12720
gttcttcggg ctctgtcgtg ccgttgtttg aaaaacagat tgcccaaggt gggccagtta    12780
ccttgactca tcgtgacatt attcgctatt tcatgacaat tccggaagca tcacagttgg    12840
tgattcaagc gggggcgatg gggcatggcg gcgatgtctt tgtcttagac atgggcgatc    12900
cggtcaagat ttatgactta gccaaacgca tgatccggtt aagtggcttg agtgtacggg    12960
atgataaaaa tccagatggc gatattgcca ttgaagttac gggattacgt ccaggtgaga    13020
aactgtatga agaattactg attggtgatt cagttcaagg tacctctcat ccacgaatta    13080
tgacggccaa cgaagtgatg ctaccgtggc aggatctatc gctcttactt aaagagctgg    13140
atcaagcttg tcatgacttt gatcatgagc gaattcgcag tttgttgtta caagcaccag    13200
cggcattcaa tccaactgat gatatttgcg atcagtttg gcagcagaaa aaatcgctgt     13260
tatcacaagc gagcaatgtc attcgcctgt gattgcttag gtttaacctt ccacaccaat    13320
tcttcacctc tcttacaaat ccccgctagg cggtacatcg tgaccgcctt taccctgatg    13380
cctgctcttt aacaaacagg acatcagtgt atgtttaaac cttttagcgc cgaattttc    13440 ggcactttct ggctggttct gggtggctgt ggtagcgcct tgatctctgc tgctttccca    13500
cagttaggta taggcttttt gggcgtggcg ttggcgtttg gtctgacagt agtcaccatg    13560
gcttatgcgg tcgggcacat ctctggtgcg cattttaacc ccgcggtgac cttgggtctg    13620
tgggccggtg gacgctttcc tgcagcgcgc gtgttacctt                          13660
```

<210> SEQ ID NO 17
<211> LENGTH: 12540
<212> TYPE: DNA
<213> ORGANISM: Plesiomonas shigelloides
<220> FEATURE:
<223> OTHER INFORMATION: GenBank Accession No. AF285970, Plesiomonas shigelloides Related Sequences, Plesiomonas shigelloides O antigen gene cluster, complete sequence

<400> SEQUENCE: 17

```
attcttaaca cattgataag taatgggttt atttaatgtc aaaagcatct gaaccacaac      60
agactcctta tctgatccca caggggcttt atcccgtcta tatgccaaaa gcagaggatg    120
aaatcgatct tttcgagctt ttaagcacct tgtggaagaa aaagtgggtg attttatttg    180
tcacattgct gactacagga ttagcggcag tgtatgcctt taccgcaaaa gagcagtgga    240
cagcaaaaac ttatattcag gcaccacgta ttgctgaact agggagttat cttaaatttc    300
gtcaagcgta tgcccgaatt ttaaatcaac cgttagatac gagtgctttg gctaatgggt    360
tgttttctga tttgattttg attgctgaat caccagacac caaatttaaa tttttagagc    420
gaactgagta ttataaaaag gaaacacaga gtttatcctc tgagcaagat aagaaaattt    480
ggttagctga gcaagcgaaa aaaggccttg tgattacgcc accaaaggaa aagaaaata    540 taagttacta cacaatacaa gcatcggcag attcagcgca agaggcatat aaactactac    600
aggggtatct aaaggatgtt aataatcaag ctgtaacatt aagtcttgat gagtttgatc    660
aaaacatcaa cactctttta gttagtttaa agaaagaagt taatgatatc gatttccaga    720
aaaaagcaga aaaactggat cagatagcat atattcagcg agatttaact acagcagagc    780
aagcgggtat tactgattat cgttctagta aaaatggctt tgataatgcg caaagtagct    840
ataagttctt gctcggtgaa aaactgttgt cagcagagct gaaagcaact aaagacgctc    900
ctattattta tccttttaga tattatgaag tgaagcgtca aattgatgag ttagaaggga    960
tgttacgcga taatattcag gcacaagcat atcgatatca aatgaagcca tctgagccag   1020
```

-continued

```
ttataaaaga caaacccaac aaagcattaa ttttgattct tggtgcatta ctaggggcaa    1080
tgtttgctat agttggtaca ttagtttatg cgacattaaa agataaaacc aagttagatt    1140
aaactgggtt acgtattgtt gtgtcaatgc gaaatagatg ttctatgtgc actttataat    1200
ggataagaaa atgaaattcg atactttgaa tgcgaaaatt gggattatag gccttggtta    1260
tgttggattg cctcttgctg ttgagtttgg aaagaaagta acgacgattg gatttgatat    1320
taataagtct cgtattgatg aattgcgaaa tggtcacgat agtacattag agtgctcaaa    1380
tttagagttg ttagaagcaa ctaaattgac gtacgcctgt tcattagatg cactaaaaga    1440
gtgtaatgta tttattgtaa ctgttccaac tccaattgat aaacataaac agccagatct    1500
aacacctcta attaaagcat ctgaaacatt gggtaagata ataaagaaag gcgatgttat    1560
tatttatgag tcaacagttt accctggagc gacagaagaa gattgtatac cagttgtaga    1620
gaaagtatca ggtcttaagt ttaatattga tttttttgcc ggttattcac ctgagcgtat    1680
taatcctggg gataaagagc atcgtgtaac taatatcctt aaggtgacca gtggatctac    1740
accggatgtt gctgagtatg tagatcagct atataaatta ataattactg tcggtacgca    1800
taaagcatca tcgataaaag tagcagaggc tgcaaaagta attgaaaaca cgcagcgaga    1860
tgtcaatatt gcattgatta atgagttatc tattatattt aataagttag ggattgatac    1920
cttagaggtt cttgaggctg caggtacgaa gtggaatttt ttacctttta ggcccggttt    1980
agtaggtggc cactgtatag gtgtagatcc ttattatctt acacataaag cgcaaagtgt    2040
cggctatcat ccagagatga ttttagccgg acgtcgttta aatgatagta tggggcagta    2100
tgtcgtttcc cagttagtca aaaaaatgtt gaaacaacgg attcaagttg aagggcgaa    2160 tgtgttagtg atggggctta catttaaaga gaattgccca gatctacgaa acactaaagt    2220
gattgatatt atttcagagt taaaagaata caatatcaat atagatatta tagatccatg    2280
gtgttctacc gatgaggcac aacatgaata tggattaact ttatgtgaag atcctaaagt    2340
taatcattat gatgcaataa ttatcgctgt tgcacacaat gagtttcgcg agatgggaga    2400
gagcgctatt cgtgcattag gtaaagacga gcacgttttg ttcgatttaa aatatgtgct    2460
tgataaaaaa agtatcgata tgcgcttgta agagtgatta aaaaaatcaa atcctctttg    2520
atatgataca cctcagcatt ttatgctagg tttagcactt gattaatata catggatatt    2580
tatatgtctc gctatgaaga gattacacag cagttaattt tttcaccgaa aacttggtta    2640
attactggtg tcgctggctt tataggatca aatcttttag aaaagttact taaattaaac    2700
caggttgtta ttgggttaga taacttttcc acgggacatc aatataatct tgatgaagtt    2760
aaaacattag tttccactga acagtggagt cgattttgct ttatagaagg tgatattcga    2820
gatctcacta cctgtgagca agttatgaaa ggtgttgatc atgtcttaca tcaggctgcg    2880
ctaggttctg tacctcgttc aattgttgat cctataacaa ccaatgcaac taatattact    2940 ggattttttga atatcttaca tgcggctaaa aatgcacaag tacaaagttt tacttatgct    3000
gcatcaagct caacttatgg agatcatccc gcactaccaa agtagaggaa aaacattggt    3060
aatccacttt ctcctatgc agttactaaa tatgttaacg agatttatgc tcaggtatat    3120
gctcgaacat atggttttaa aactattgga ttacgttatt ttaatgtatt tggtcgtcgt    3180
caagatccta atggagctta tgctgcagta attccaaaat ggacagcagc aatgcttaaa    3240
ggtgatgacg tatatattaa tggcgatggt gaaacgagtc gtgatttttg ttatatagat    3300
aatgttatac aaatgaatat attatctgca ttagcgaagg acagtgctaa agataatata    3360
tataatgttg cagttggtga tagaacaacg ttaaatgaat tatctggtta catttatgat    3420
```

```
gagcttaatt taattcacca tatcgataaa ttgagcatta agtatagaga gtttagatct    3480
ggagatgtta ggcattctca ggctgatgtt actaaggcta tagatttact aaagtataga    3540
ccaaatataa aaatcagaga gggattacga ctttcaatgc cgtggtatgt gagatttta     3600 aaaggctaaa ttatattaac atgaataaat aatctatttc acctctgtta ttaatgcagg    3660
ggtgaaaatc catgtgttta ttctaaatgg tcagtgtatg tttagaaaaa tgattgatgc    3720
aggtggtaca ttttttactta aagcaatatt tcaaatagga gttttgttt atttcgcaca    3780 tgtgtcagat attactacat ttggtattat tagctatgtg tttactgttt attggtttgt    3840
gcttaacttc tctgattatg gatttagaac aaaattagtg aaagatattt ctgataatag    3900
ttattctgca tcagaattat tatccagaag tgatggagtt aaaacatatg ttttttttctt   3960 catttttata atcttcatgt tttattctta tgtttctgat tcaatttcat taactctgct    4020
tgtttatatt tcatctgcat attttgtttg tatttcaagt ggtagattta gcttgctaca    4080
ggctgttggt cggtttagat gtgaattata tataaatatc tactcaacaa ttatatatat    4140
tgggtgtaat ttattttttat ctctgtttat cgaacctcta tattatagtg cgatatcaat   4200
attcatatac tcaatttcgc ttttggtttt ctcatcacat aaatgcaatg tgccatgttt    4260
tcatataaaa agaccaagtc ttttagttta taaagatttt ttggatgcaa ctccgttcgc    4320
tattctggtg ttactaaatg ttgttttatc tagtattgac cttttatat taaaagaata     4380 tttctcttat aatagtgttg ctatatatca ggtggtaact agggttaata ccggtctaat    4440
gatagtgttt aatgttattt atactgtttt attgccttca ttttcttatt atctgaaaaa    4500
ttctgaatgg ggtaatataa ggaaattaca acgatatata tcactgttag tcttattact    4560
atgtttatgc tattattttt ttggcatcta tttcgtaggg atattgtttg gtgatgagta    4620
taaggtaata tcttctgcaa catttttgat aatgtttatg gctcttatta aatataatttt   4680 ttggctaata aatgaacttt atcttgtgtg tagtggaaat caaagcgagc gagttaaatc    4740
gtattgtatt ggtgtggtca tttcaatagc ggttttcttt tattttatac ctcggtatgg    4800
atggagtggg gcggttttg gaagtgccat tgcaacatta gtaattggaa tattttatat     4860
tatttctgtg aaaaaagatt gtgggaaaat tcttcatgat aagtattcac taatgatgat    4920
ctttgtccca ttttcttttt attttattat taatggtcag tagcggttgt tatattaatc    4980
tgttgttgtt ttatatcgtt ccattaatat gtttagactc gattggaagt ctaataaagg    5040
ttaagtatgt taatataccct atatcctgta cttttgttat ttaatatcct tccggttttt    5100
ttttatggac aaatgaactc tgatttagag cgttttttg gagttcctat tggctatatt     5160
tcagatctaa tattttatttt ctttgttgct ttaacatcta taataacgtt gaggtttcac   5220
gtttctctgt ggacaaagaa attattattt ttaggcatca tattcctgat ttatatcagc    5280
attcagatgt tgttgttatc agcggatatc tcaggtgtcg taattttatt atcgttttt     5340 tctaattttta tagctttggt tcttttggta tcatttttgca ttggtaaaga tgagcttat    5400 ttaactcatt cggttagaaa tataaatgtt gtaatgtgtt ttggtattat ctgtggagtt    5460
gtaaaattat ttattggtta ttctgaagat agtaattttta tagtttattt aaatagaaat   5520
gccaccgcaa ttatagtagt gtgctttat tgtgtatatt catactttta tcgtggtcga     5580
aagtcttggt atgtatcatc tgtattgtac tctctgttct ttcttttttct agatagccga   5640 gcaggaataa tatcatttgc tatatcgttg ttttttgttt ttcttcagtt aacaaagaag    5700
gaaaagttat taatatcatt gttttttgtt cctcttctaa ctttaggtat ttcttttact    5760
gatataggca ctcgtcttga acgaatgctg tcttcgtcac aggttatatt ctctggtggt    5820
```

```
aacactctta caaaaagtca gaatgattat cgtcgagttg agttagtatt tattggggtt    5880
gatgttttaa aagaaaatta tttaattggc actggattag gtgttgcaaa ttatgtaaag    5940
gctatagata aaaagttttt aggaagtacc aactttgggt tggcgcataa tttttattta    6000
tcttattcgg ctcagttagg gattattggt tttattttgc ttatttctgt attttatata    6060
atgctgtctc caattttaa atgcggaggg tatattggta aagggtgcgt ttttgctttg    6120
gctttctatg tctttttaa tgagtatata ttgacgccag cgatatatat ttatatttct    6180
atttttttat cggtggtttt tatacgtaat tctaggatga gaatatgttg ttagaatatg    6240
ttgaaagaaa aatttcctta gccttgagta agtatcctaa ggtaagggat gttattaagt    6300 tctttatt atatatcgca tcattattcg gaattatttt gaataaaaat aagacggtta    6360
ttcaatcaaa aatatacgag atttcaattg atgattctga agaatcattt tttggctatt    6420
atgaccatag tccaatgagc tctaatgggc ggtacgtatt gttccactct agtgcgttta    6480
gcactaaacg acacccaaag aaagttaagt atatatctat ttgcgtaaaa gaccttctta    6540
ataacaaagt ttataagcta tatgatacgc gagcatttaa ttggcagcag ggaagccgat    6600
taatgtggat tgatgatgac aatataattt ttaatgacta tgaaaataat ggatacatta    6660
gtgttgtcta ttctttgtct ttgatgaagg ttataaaaaa aataaactat ccgatttatg    6720
atgtgaataa ttcaaggct gtgacgttag atttctcatg gctggctaaa tatgatagcg    6780
attatggtta ttataataag aaatcatttt ctacagatat ttcaatcatt aatttgaaca    6840
cgggcggaat agaattattt ttatccttag acgaaatgct aaagagaact aattttaaat    6900
gtaatattga tgttgaacat gtggtcaatc attttatgtt tgctcccgat ggacgttccg    6960
ttatgttcat acatcgatac tatacaccta aggaaagcg tgaaaggtta atacattgga    7020
atttaataaa tgataatgtt cgagtcctaa taatgaatc gattattagt cattgttgtt    7080
ggaatgggaa tgatgaaatt ataggttttt ttggtgcaga aatagattcg cttaattatt    7140
atagattgtc aattgaatcc tgtaatacag agaaattgtt ttttgatgca agaaaatatt    7200
ctgatggaca tcctactata gttcataata gatatattat atctgatact tacccagata    7260
aaaatagaat taaaaagttg tttgtttatg accttgtcaa aaatgattat cgcgagcttg    7320
gattgtttta tgagtcaatg agtttttttt cttattctcg atgtgactta catccaagga    7380
tctcggttga taatagattt ttgtttgttg attcagttca ctcagggaaa agaaaactat    7440
attttatgag gagtggtatt tgtgagtgat gttctagtat ctttaattat agtttgcttt    7500
aatgcagaga agtatattga aaaatctctt ttggcattta ttaatcaaga tgttggatta    7560
gataaatttg aattgattat tgtagatggg gattcatctg ataatacaat atctattgtt    7620
caggatgttt tttctaaaca tagtaacatt aagcataaaa ttatcaataa taaaaaaaga    7680
actcttgcta cgggttggaa tattggggtg ctagaagcta atggtaagtt tgtgtgtaga    7740
gttgatgcac atagtgatat tccaaataac tatatatcta aattattaga tgattatttt    7800
aatattatgc agtttgatga tagcgttgtt ggtgttggag gtgtattaac taattcttat    7860
aaaactaagt ttggttcaat tgtagcggat ttttatgcat ctaaatttgg tgttggtaat    7920
tctccattta ggtgcgtaga caaaaataat cgactaaaaa aaacagatac ggctgtcttt    7980
gctttatata ataaagatgt gttttttgat gttggactt ttaatgaagt attagataga    8040
aatcaagata ttgatttca taagagagtt ttaagcaata ttttttcatt atatacagat    8100 aatagttat tgttgagta ttatgttaga gataattta aagatttcat aaagaaaggt    8160
tttcttgatg gtttttgggt tgttatgtct ggagcatatt attttagaca tatcgtgcca    8220
```

```
cttttttttg ttttgtattt aattgtatct ttttctcttt tctttgctac tggtgattat    8280
atatatttat ctttcttatt ttcttatttt cttatttcta ttttgttttc aattcgagat    8340
gggcgaagtt ttataggtaa agtatttctt cctttatat ttttgtctta tcatatttct    8400
tatggatgtg gatcgttatt atcttttttg aaaaggtatt ttaaatgaaa aattttattc    8460
cttttgcgtt acctgaaatt ggcgaagaag aaattgcaga ggtaattgac tctttacgtt    8520
caggttggat tacgacaggt cctaaggcta agcaatttga caagaatttt tctaattacc    8580
taggagcgaa cgttcaatca ttagctgtta actctgctac gtcgggctta catttggctc    8640
ttgaagctgt tggcgtaaaa cctggagacc aagttattgt cccatcatat acattcactg    8700
ctactgccga aattgtcagg taccttggtg ctgatcctgt aattgttgat gtagatcgta    8760
aaacatttaa tatatcagtt gatgccattg agaaggctat tactaataaa acaaaggcga    8820
ttattccagt acacttcgct ggattagctt gtgacatgga ttcaatctta tcaattgcta    8880
aaaaatatga cctaaaggtt gtcgaggatg ccgctcatgc atttcctaca acatataaag    8940
gaagtaagat aggaacgctt gattcagatg ctacggtttt tagcttctac gccaataaaa    9000
ctatgacaac cggtgaaggc ggaatggttg tttcaaaaaa taaagatata attgagcgtt    9060
gtaaggtaat gcgtttacat ggaatcagtc gtgacgcttt tgaccggtac cagtctaaaa    9120
ctccttcttg gttttatgag gttgtagctc cagggtttaa atacaatatg cctgatatct    9180
gtgcggcaat cggtattcat caacttagaa agatcgatga ttttcagaaa aaacgtcaac    9240
gaatggcaaa aatttacgat gatgcgttaa aagaattgcc acttgaattg cctgaatggc    9300
ctactaatgc tagtgatatt catgcttggc atctatatcc tatccgctta aaaactgatt    9360
cggctattaa tcgcgatgat tttattaaga agttatcaga tcttggaatt ggttgttctg    9420
tccattttat accgttgcat aagcaaccgg tttggcgtga tacatataat ttgaacgcca    9480
gtgactttcc agtttctgag gagtgttatt taaatgaaat atctattcct ctttatacta    9540
aaatgacgga tcaagatcag ttgttcgtta tcgaatcgat tagacaatta tttatgtaat    9600
ggtattttat attaaatgaa acgtattttt gatgttatcg tggcaggctt aggcctgctt    9660
tttctatttc ctgtttttat cattgtgtca atgttaattg ttgctgattc taagggagt    9720
gttttttta ggcagtatag agttgggaga tttgggaaag attttaggat acataaattt    9780
agaacgatgt ttatcgattc agaaaaaaaa ggacggataa cagttggtca agatgctcgg    9840
gtaaccagag ttggatggta tttacggaag tacaaaatcg atgagctgcc tcaattgata    9900
gatgttcttt ctggaacaat gagtttggtt ggcccaagac cggaagtgag ggagtttatt    9960
gatgagtatc ctgatgatat aagggaaaaa gttttatcgg ttaggccagg gataactgac    10020
ttagcatcta tagaaatggt agatgaaaat gagattttgt ctagttatga tgacccacgt    10080
agggcttata tagatataat tcttccaatc aagcaaagat attatttgga ttatgttgct    10140
aacaattcag taaagtatga ttgtgtgata atttggaaaa ctattattaa gattttgtcg    10200
cgataataag gtagtgtagg atgattgata gaatattgga gctgccaaga attgttaaga    10260
gaggtatcat catctgcatt gatgtagtta tggtgatatt ctcattttgg ttgtcttatt    10320
ggttgaggct tgatgagcaa acggcttttc ttagtgcacc gatgtggttt gctgcagcta    10380
ttcttaccat atttaccgtg tttatattta tcaggattgg gctttatcgg gcagtcttac    10440
ggtatgttag tgcaaagata atgttgctaa tatcagttgg tattctggcc tcaacgttat    10500
ctcttgtcgt tatatcatat tcgctatcca taatgttgcc gcgcactgtt gtcggaattt    10560
atttttggt tttactttta ctgacatcag gctctagatt gcttttaga atgatactta    10620
```

```
actatggagt taagggtagt gcgcctgttt tgatttatgg cgctggtgaa tctggccgac    10680
aattattgcc agcattaatg caggcaaaag aatattttcc tgtggcattt gtggatgata    10740
atcctcgctt gcataaggcc gtcattcatg gtgtaacagt ttatccctcg gataaactga    10800
gttacctagt agatcgctat ggtataaaga aaattctttt ggcgatgccg agcgtcagta    10860
agtcacaaag gcagaaagtg attactcgtt tagagcattt accgtgtgaa gttctctcta    10920
ttccgggcat ggtcgattta gtcgaaggtc gagcacaaat cagtaatctc aaaaaagtat    10980
cgattgatga cttgctaggc cgtgatccag ttgctcctga tgccaaattg atggcggaga    11040
acattacagg caaagcagtt atggtcactg gggcggagg atcgatcggc tctgagcttt     11100
gtcgtcaaat tgttcgatat aagccagcca aattggttct atttgaactg tctgaatatg    11160
ccctgtatgc cattgagaaa gagctatcga cgctgtgtga taagaaggt ttggatgtct     11220 cagtgatccc tctgttgggc tcggtgcagc gtcagaatcg cttacagatg gtgatgaagt    11280
cctttggtat tcaaacggtt tatcatgcgg ctgcttataa acatgtgcct ctggttgagc    11340
ataatgtggt ggaaggggtg cgtaataatg tgtttggtac cttgtactgc gctgagtcgg    11400
cgatcgatag tggcgttgaa acctttgtgt tgatttccac cgataaagcg gtgcggccga    11460
ccaacactat ggggacaacc aagcgcctgg ctgagttggt attgcaggcg ttgtctgcac    11520
ggcaaagcaa aacccgtttt tgtatggtgc gatttggtaa tgtgctggga tcctcgggct    11580
cagttgtacc attgtttgaa aagcagattg cccaaggtgg gccagttacc ctgactcatc    11640
gtgacattat tcgctatttt atgacaattc ctgaagcatc gcagttggtg attcaagcgg    11700
gggcgatggg gcatggcggc gatgtctttg tcttagacat gggcgatccg gttaagattt    11760
atgacttagc caaacgcatg atccggttaa gtggcttgac tgtgcgggat gataaaaatc    11820
cagatggcga tattgccatt gaagttacgg gattacgtcc aggtgagaaa ctgtatgaag    11880
aattactgat tggtgattca gttcaaggta cctctcatcc acgaattatg acggccaacg    11940
aagtgatgct accgtggcag gatctatcgc tcttacttaa agagctggat caagcctgtc    12000
atgactttga tcatgagcgc attcgcagct tattgttaca agcaccagcg gcattcaatc    12060
caactgatga tatttgcgat ctagtttggc agcagaaaaa atcgctgtta tcacaagcga    12120
gcaatgtcat acgcctgtga ttgtttagat ttaaccttcc acaccaattc ttcacctctc    12180
ttacaaatcc ccgctaggcg gttcatcgtg accgccttta ccctgatgtc agctctttaa    12240
caaacaggac atcagtgtat gtttaaacct tttagcgccg aattttttcgg tactttctgg    12300 ctggttctgg gtggctgtgg tagcgccttg atctctgctg cttttccctca gttaggtatt    12360 ggcttttttgg gcgtggcgtt ggcttttggt ctgacagtag tcaccatggc ttatgcggtc    12420
gggcatatct ccggagcgca ttttaacccc gcggtgacct tgggtctgtg ggccggtgga    12480
cgcttccctg cggcgcgcgt gttaccttac atcatcgctc aggttatcgg cggtattgcc    12540
```

<210> SEQ ID NO 18
<211> LENGTH: 14991
<212> TYPE: DNA
<213> ORGANISM: Plesiomonas shigelloides
<220> FEATURE:
<223> OTHER INFORMATION: GenBank Accession No. AB025970, Plesiomonas
    shigelloides Related Sequences, Plesiomonas shigelloides gene for
    ORF1P, ORF2P, ORF3P, ORF4P, ORF5P, ORF6P, ORF7P, ORF8P, ORF9P,
    ORF10P, and ORF11P

<400> SEQUENCE: 18

```
aagcttgatc aaatagctca tattcagcga gatttaacaa ctgcggaaca agccggaatc      60
attgattatc gctctagcaa aggcggcttc gataatgcgc aaagtagcta taagttcttg     120
ctcggcgaaa aactgttatc agcagagcta aaagcaacta aagatgcgcc aattatttac     180
ccatttagat attacgaagt gaaacgtcaa attgatgagt tagaaggaat gttacgcgat     240
aacattcagg cgcaagcata tcgatatcaa atgaagccat ctgagccagt tataaaagac     300
aaacccaaca aagcattaat tttgattctt ggtgcattac tagggcaat gtttgctata      360
gttggtacat tagtttatgc gacattaaaa gataaaacca gttagatta aactgggtta      420
cgtattgttg tgtcaatgcg aaatagatgt tctatgtgca ctttataatg ataagaaaa      480
tgaaattcga tactttgaat gcgaaaattg ggattatagg ccttggttat gttggattgc     540
ctcttgctgt tgagtttgga aagaaagtaa cgacgattgg atttgatatt aataagtctc     600
gtattgatga attgcgaaat ggtcacgata gtacattaga gtgctcaaat ttagagttgt     660
tagaagcaac taaattgacg tacgcctgtt cattagatgc actaaaagag tgtaatgtat     720
ttattgtaac tgttccaact ccaattgata aacataaaca gccagatcta acacctctaa     780
ttaaagcatc tgaaacattg ggtaagataa taagaaagg cgatgttatt atttatgagt      840
caacagttta ccctggagcg acagaagaag attgtatacc agttgtagag aaagtatcag     900
gtcttaagtt taatattgat ttttttgccg gttattcacc tgagcgtatt aatcctgggg     960
ataaagagca tcgtgtaact aatatcctta aggtgaccag tggatctaca ccggatgttg    1020
ctgagtatgt agatcagcta tataaattaa taattactgt cggtacgcat aaagcatcat    1080
cgataaaagt agcagaggct gcaaaagtaa ttgaaaacac gcagcgagat gtcaatattg    1140
cattgattaa tgagttatct attatattta ataagttagg gattgatacc ttagaggttc    1200
ttgaggctgc aggtacgaag tggaattttt tacctttag gcccggttta gtaggtggcc     1260
actgtatagg tgtagatcct tattatctta cacataaagc gcaaagtgtc ggctatcatc    1320
cagagatgat tttagccgga cgtcgtttaa atgatagtat ggggcagtat gtcgtttccc    1380
agttagtcaa aaaaatgttg aaacaacgga ttcaagttga aggggcgaat gtgttagtga    1440
tggggcttac atttaaagag aattgcccag atctacgaaa cactaaagtg attgatatta    1500
tttcagagtt aaaagaatac aatatcaata tagatattat agatccatgg tgttctaccg    1560
atgaggcaca acatgaatat ggattaactt tatgtgaaga tcctaaagtt aatcattatg    1620
atgcaataat tatcgctgtt gcacacaatg agtttcgcga gatgggagag agcgctattc    1680
gtgcattagg taaagacgag cacgttttgt tcgatttaaa atatgtgctt gataaaaaaa    1740
gtatcgatat gcgcttgtaa gagtgattaa aaaaatcaaa tcctctttga tatgatacac    1800
ctcagcattt tatgctaggt ttagcacttg attaatatac atggatattt atatgtctcg    1860
ctatgaagag attacacagc agttaatttt ttcaccgaaa acttggttaa ttactggtgt    1920
cgctggcttt ataggatcaa atcttttaga aaagttactt aaattaaacc aggttgttat    1980
tgggttagat aacttttcca cgggacatca atataatctt gatgaagtta aaacattagt    2040
ttccactgaa cagtggagtc gattttgctt tatagaaggt gatattcgag atctcactac    2100
ctgtgagcaa gttatgaaag gtgttgatca tgtcttacat caggctgcgc taggttctgt    2160
acctcgttca attgttgatc ctataacaac caatgcaact aatattactg gattttgaa     2220
tatcttacat gcggctaaaa atgcacaagt acaaagtttt acttatgctg catcaagctc    2280
aacttatgga gatcatcccg cactaccaaa agtagaggaa acattggta atccactttc     2340
```

```
tccttatgca gttactaaat atgttaacga gatttatgct caggtatatg ctcgaacata   2400
tggttttaaa actattggat tacgttattt taatgtattt ggtcgtcgtc aagatcctaa   2460
tggagcttat gctgcagtaa ttccaaaatg gacagcagca atgcttaaag gtgatgacgt   2520
atatattaat ggcgatggtg aaacgagtcg tgattttgt tatatagata atgttataca    2580
aatgaatata ttatctgcat tagcgaagga cagtgctaaa gataatatat ataatgttgc   2640
agttggtgat agaacaacat taaatgaatt atctggttac atttatgatg agcttaattt   2700
aattcaccat atcgataaat tgagcattaa gtatagagag tttagatctg gagatgttag   2760
gcattctcag gctgatgtta ctaaggctat agatttacta cagtatagac caaatataaa   2820
aatcagagag ggattacgac tttcaatgcc gtggtatgtg agatttttaa aaggctaaat   2880
tatattaaca tgaataaata atctatttca cctctgttat taatgcaggg gtgaaaatct   2940
atgtgtttat tctaaatggt cagtgtatgt ttagaaaaat gattgatgca ggtggtacat   3000
ttttacttaa agcaatattt caaataggag ttttgtta tttcgcacat gtgtcagata    3060
ttactacatt tggtattatt agttatgtgt ttactgttta ttggtttgtg cttaacttct   3120
ctgattatgg atttagaaca aaattagtga agatatttc tgataatagt tattctgcat    3180
cagaattatt atccagaagt gatggagtta aaacatatgt ttttttcttc attttataa    3240 tcttcatgtt ttattcttat gtttctgatt caatttcatt aactctgctt gtttatattt   3300
catctgcata ttttgtttgt atttcaagtg gtagatttag cttgctacag gctgttggtc   3360
ggtttagatg tgaattatat ataaatatct actcaacaat tatatatatt gggtgtaatt   3420 tattttatc tctgtttatc gaacctctat attatagtgc gatatcaata ttcatatact    3480
caatttcgct tttggttttc tcatcacata atgcaatgt ccatgtttt catataaaaa    3540 gaccaagtct tttagtttat aaagattttt tggatgcaac tccgttcgct attctggtgt   3600
tactaaatgt tgtttatct agtattgacc ttttatatt aaaagaatat ttctcttata    3660
atagtgttgc tatatatcag gtggtaacta gggttaatac cggtctaatg atagtgttta   3720
atgttattta tactgtttta ttgccttcat tttcttatta tctgaaaaat tctgaatggg   3780
gtaatataag gaaattacaa cgatatatat cactgttagt cttattacta tgtttatgct   3840 attattttt tggcatctat ttcgtaggga tattgtttgg tgatgagtat aaggtaatat   3900
cttctgcaac atttttgata atgtttatgg ctcttattaa atataatttt tggctaataa   3960
atgaacttta tcttgtgtgt agtggaaatc aaagcgagcg agttaaatcg tattgtattg   4020
gtgtggtcat ttcaatagcg gttttctttt atttataccc tcggtatgga tggagtgggg   4080
cggttttggg aagtgccatt gcaacattag taattggaat attttatat ttctgtga     4140 aaaaagattg tgggaaaatt cttcatgata agtattcact aatgatgatc tttgtcccaa   4200 ttttcttta ttttattatt aatggtcagt agcggttgtt atattaatct gttgttgttt     4260
tatatcgttc cattaatatg tttagactcg attggaagtc taataaaggt taagtatgtt   4320
aatataccta tatcctgtac ttttgttatt taatatcctt ccggtttttt tttatggaca   4380
aatgaactct gatttagagc gttttttttgg agttcctatt ggctatattt cagatttaat   4440
attttatttc tttgttgctt taacatctat aataacgttg aggtttcacg tttctctgtg   4500
gacaaagaaa ttattatttt taggcatcat attcctgatt tatatcagca ttcagatgtt   4560
gttgttatca gcggatatct caggtgtcgt aatttattta tcgtttttt ctaatttat     4620 agctttggtt cttttggtat cattttgcat tggtaaagat gagctttatt taactcattc   4680
ggttagaaat ataaatgttg taatgtgttt tggtattatc tgtggagttg taaaattatt   4740
```

```
tattggttat tctgaagata gtaattttat agtttattta aatagaaatg ccaccgcaat    4800
tatagtagtg tgcttttatt gtgtatattc atacttttat cgtggtcgaa agtcttggta    4860
tgtctcatct gtattgtact ctctgttctt tcttttctta gatagccgag caggaataat    4920
atcatttgct atatcgttgt ttttgtttt tcttcagtta acaaagaagg aaaagttatt    4980
aatatcattg ttttttgttc ctcttctaac tttaggtatt tcttttactg ataaggcac    5040 tcgtcttgaa cgaatgctgt cttcgtcaca ggttatattc tctggtggta acactcttac    5100
aaaaagtcag aatgattatc gtcgagttga gttagtattt attggggttg atgttttaaa    5160
agaaaattat ttaattggca ctggattagg tgttgcaaat tatgtaaagg ctatagataa    5220
aaagttttta ggaagtacca actttgggtt ggcgcataat ttttatttat cttattcggc    5280
tcagttaggg attattggtt ttattttgct tatttctgta ttttatataa tgctgtctcc    5340 aattttaaa tgcggagggt atattggtaa agggtgcgtt tttgctttgg ctttctatgt    5400
cttttttaat gagtatatat tgacgccagc gatatatatt tatatttcta tttttttatc    5460
ggtggttttt atacgtaatt ctaggatgag aatatgttgt tagaatatgt tgaaagaaaa    5520
atttccttag ccttgagtaa gtatcctaag gtaagggatg ttattaagtt cttttatta    5580 tatatcgcat cattattcgg aattattttg aataaaaata agacggttat tcaatcaaaa    5640
atatacgaga tttcaattga tgattctgaa gaatcatttt ttggctatta tgaccatagt    5700
ccaatgagct ctaatgggcg gtacgtattg ttccactcta gtgcgtttag cactaaacga    5760
cacccaaaga aagttaagta tatatctatt tgcgtaaaag accttcttaa taacaaagtt    5820
tataagctat atgatacgcg agcatttaat tggcagcagg gaagccgatt aatgtggatt    5880
gatgatgaca atataatttt taatgactat gaaaataatg gatacattag tgttgtctat    5940
tctttgtctt tgatgaaggt tataaaaaaa ataaactatc cgatttatga tgtgaataat    6000
tacaaggctg tgacgttaga tttctcatgg ctggctaaat atgatagcga ttatggttat    6060
tataataaaa aatcattttc tacagatatt tcaatcatta atttgaacac gggcggaata    6120
gaattatttt tatccttaga cgaaatgcta aagagaacta attttaaatg taatattgat    6180
gttgaacatg tggtcaatca ttttatgttt gctcccgatg gacgttccgt tatgttcata    6240
catcgatact atacacctaa aggaaagcgt gaaaggttaa tacattggaa tttaataaat    6300
gataatgttc gagtcctaat aaatgaatcg attattagtc attgttgttg gaatgggaat    6360
gatgaaatta taggttttttt tggtgcagaa atagattcgc ttaattatta tagattgtca    6420
attgaatcct gtaatacaga gaaattgttt tttgatgcaa gaaaatattc tgatggacat    6480
cctactatag ttcataatag atatattata tctgatactt acccagataa aaatagaatt    6540
aaaaagttgt ttgtttatga ccttgtcaaa atgattatc gcgagcttgg attgttttat    6600
gagtcaatga gttttttttc ttattctcga tgtgacttac atccaaggat ctcggttgat    6660
aatagatttt tgtttgttga ttcagttcac tcagggaaaa gaaaactata ttttatgagg    6720
agtggtattt gtgagtgatg ttctagtatc tttaattata gtttgcttta atgcagagaa    6780
gtatattgaa aaatctcttt tggcatttat taatcaagat gttggattag ataaatttga    6840
attgattatt gtagatgggg attcatctga taatacaata tctattgttc agaatgtttt    6900
ttctaaacat agtaacatta agcataaaat tatcaataat aaaaaaagaa ctcttgctac    6960
gggttggaat attggggtgc tagaagctaa tggtaagttt gtgtgtagag ttgatgcaca    7020
tagtgatatt ccaaataact atatatctaa attattgat gattattta atattatgca    7080 gtttgatgat agcgttgttg gtgttggagg tgtattaact aattcttata aaactaagtt    7140
```

```
tggttcaatt gtagcggatt tttatgcatc gaaatttggt gttggtaatt ctccatttag    7200
gtgcgtagac aaaaataatc gactaaaaaa aacagatacg gctgtctttg ctttatataa    7260
taaagatgtg ttttttgatg ttggacttttt taatgaagta ttagatagaa atcaagatat    7320
tgattttcat aagagagttt taagcaataa tttgtcatta tatacagata atagtttatt    7380
tgttgagtat tatgttagag ataattttaa agatttcata agaaaggtt ttcttgatgg     7440 tttttgggtt gttatgtctg gagcatatta ttttagacat atcgtgccac ttttttttgt    7500
tttgtattta attgtatctt tttctctttt ctttgctact ggtgattata tatatttatc    7560
tttcttattt tcttattttc ttatttctat tttgttttca attcgagatg ggcgaagttt     7620
tataggtaaa gtatttcttc ctttatatt tttgtcttat catatttctt atggatgtgg      7680
atcgttatta tctttttga aaggtattt taaatgaaaa attttattcc ttttgcgtta       7740
cctgaaattg gcgaagaaga aattgcagag gtaattgact ctttacgttc aggttggatt    7800
acgacaggtc ctaaggctaa gcaatttgaa caagaatttt ctaattaccct aggagcgaac   7860 gttcaatcat tagctgttaa ctctgctacg tcgggcttac atttggctct gaagctgtt     7920 ggcgtaaaac ctggagacca agttattgtc ccatcatata cattcactgc tactgccgaa    7980
attgtcaggt accttggtgc tgatcctgta attgttgatg tagatcgtaa aacatttaat    8040
atatcagttg atgccattga gaaggctatt actaataaaa caaaggcgat tattccagta    8100
cacttcgctg gattagcttg tgacatggat tcaatcttat caattgctaa aaaatatgac   8160
ctaaaggttg tcgaggatgc cgctcatgca tttcctacaa catataaagg aagtaagata   8220
ggaacgcttg attcagatgc tacggttttt agcttctacg ccaataaaac tatgacaacc   8280
ggtgaaggcg gaatggttgt ttcaaaaat aaagatataa ttgagcgttg taaggtaatg    8340
cgtttacatg gaatcagtcg tgacgctttt gaccggtacc agtctaaaac tccttcttgg   8400 tttttatgagg ttgtagctcc agggtttaaa tacaatatgc ctgatatctg tgcggcaatc  8460
ggtattcatc aacttagaaa gatcgatgat tttcagaaaa aacgtcaacg aatggcaaaa   8520
atttacgatg atgcgttaaa agaattgcca cttgaattgc ctgaatggcc tactaatgct   8580
agtgatattc atgcttggca tctatatcct atccgcttaa aaactgattc ggctattaat   8640
cgcgatgatt ttattaagaa gttatcagat cttggaattg gttgttctgt ccattttata   8700
ccgttgcata agcaaccggt ttggcgtgat acatataatt tgaacgccag tgactttcca   8760
gtttctgagg cgtgttattt aaatgaaata tctattcctc tttatactaa aatgacggat    8820
caagatcagt tgttcgttat cgaatcgatt agacaattat ttatgtaatg gtattttata   8880
ttaaatgaaa cgtattttg atgttatcgt ggcaggctta ggcctgcttt ttctatttcc    8940
tgtttttatc attgtgtcaa tgttaattgt tgctgattct aaagggagtg ttttttttag   9000
gcagtataga gttgggagat ttgggaaaga ttttaggata cataaattta gaacgatgtt   9060
tatcgattca gaaaaaaaag gacggataac agttggtcaa gatgctcggg taaccagagt   9120
tggatggtat ttacggaagt acaaaatcga tgagctgcct caattgatag atgttctttc   9180
tggaacaatg agtttggttg gcccaagacc ggaagtgagg gagtttattg atgagtatcc   9240
tgatgatata agggaaaaag ttttatcggt taggccaggg ataactgact tagcatctat   9300
agaaatggta gatgaaaatg agattttgtc tagttatgat gacccacgta gggcttatat   9360
agatataatt cttccaatca agcaaagata ttatttggat tatgttgcta acaattcagt   9420
aaagtatgat tgtgtgataa tttggaaaac tcttattaag attttgtcgc gataataagg   9480
tagtgtagga tgattgatag aatattggag ctgccaagaa ttgttaagag aggtatcatc   9540
```

```
atctgcattg atgtagttat ggtgatattc tcattttggt tgtcttattg gttgaggctt    9600
gatgagcaaa cggcttttct tagtgcaccg atgtggtttg ctgcagctat tcttaccata    9660
tttaccgtgt ttatatttat caggattggg ctttatcggg cagtcttacg gtatgttagt    9720
gcaaagataa tgttgctaat atcagttggt attctggcct caacgttatc tcttgtcgtt    9780
atatcatatt cgctatccat aatgttgccg cgcactgttg tcggaattta ttttttggtt    9840
ttacttttac tgacatcagg ctctagattg ctttttagaa tgatacttaa ctatggagtt    9900
aagggtagtg cgcctgtttt gatttatggc gctggtgaat ctggccgaca attattgcca    9960
gcattaatgc aggcaaaaga atattttcct gtggcatttg tggatgataa tcctcgcttg   10020
cataaggccg tcattcatgg tgtaacagtt tatccctcgg ataaactgag ttacctagta   10080
gatcgctatg gtataaagaa aattcttttg gcgatgccga gcgtcagtaa gtcacaaagg   10140
cagaaagtga ttactcgttt agagcattta ccgtgtgaag ttctctctat tccgggcatg   10200
gtcgatttag tcgaaggtcg agcacaaatc agtaatctca aaaagtatc gattgatgac    10260
ttgctaggcc gtgatccagt tgctcctgat gccaaattga tggcggagaa cattacaggc   10320
aaagcagtta tggtcactgg ggcgggagga tcgatcggct ctgagctttg tcgtcaaatt   10380
gttcgatata agccagccaa attggttcta tttgaactgt ctgaatatgc cctgtatgcc   10440
attgagaaag agctatcgac gctgtgtgat aaagaaggtt tggatgtctc agtgatccct   10500
ctgttgggct cggtgcagcg tcagaatcgc ttacagatgg tgatgaagtc ctttggtatt   10560
caaacggttt atcatgcggc tgcttataaa catgtgcctc tggttgagca taatgtggtg   10620
gaaggggtgc gtaataatgt gtttggtacc ttgtactgcg ctgagtcggc gatcgatagt   10680
ggcgttgaaa cctttgtgtt gatttccacc gataaagcgg tgcggccgac caacactatg   10740
gggacaacca agcgcctggc tgagttggta ttgcaggcgt tgtctgcacg gcaaagcaaa   10800
acccgttttt gtatggtgcg atttggtaat gtgctgggat cctcgggctc agttgtacca   10860
ttgtttgaaa agcagattgc ccaaggtggg ccagttaccc tgactcatcg tgacattatt   10920
cgctatttta tgacaattcc tgaagcatcg cagttggtga ttcaagcggg ggcgatgggg   10980
catggcggcg atgtctttgt cttagacatg ggcgatccgg ttaagattta tgacttagcc   11040
aaacgcatga tccggttaag tggcttgact gtgcgggatg ataaaaatcc agatggcgat   11100
attgccattg aagttacggg attacgtcca ggtgagaaac tgtatgaaga attactgatt   11160
ggtgattcag ttcaaggtac ctctcatcca cgaattatga cggccaacga agtgatgcta   11220
ccgtggcagg atctatcgct cttacttaaa gagctggatc aagcctgtca tgactttgat   11280
catgagcgca ttcgcagctt attgttacaa gcaccagcgg cattcaatcc aactgatgat   11340
atttgcgatc tagtttggca gcagaaaaaa tcgctgttat cacaagcgag caatgtcata   11400
cgcctgtgat tgtttagatt taaccttcca caccaattct tcacctctct tacaaatccc   11460
cgctaggcgg ttcatcgtga ccgcctttac cctgatgtca gctctttaac aaacaggaca   11520
tcagtgtatg tttaaacctt ttagcgccga atttttcggt actttctggc tggttctggg   11580
tggctgtggt agcgccttga tctctgctgc tttccctcag ttaggtattg cttttttggg   11640
cgtggcgttg gcttttggtc tgacagtagt caccatggct tatgcggtcg ggcatatctc   11700
cggagcgcat tttaaccccg cggtgacctt gggtctgtgg gccggtggac gcttccctgc   11760
ggcgcgcgtg ttaccttaca tcatcgctca ggttatcggc ggtattgccg ctgcggcagt   11820
gctgtatggt atcgccagcg gtaaggcggg gtttgatgcg acaaccagcg gctttgcagc   11880
taatggctat ggcattcact caccaggcgg ttatgcgtta agcgcctgta tgctgagcga   11940
```

```
gtttgtcctc agtgcgtttt ttgtcatcgt gatccacggg gcgacagaaa aacgcgctcc   12000
tgcgggcttt gcgccgttgg cgattggtct gacgctgacc atcattcatt tggtgagcat   12060
ccctgtcacc aatacctcgg ttaaccctgc gcgtagtatc gcggcggcag ttttccaagg   12120
tacttgggcg ttagatcagt tgtggatgtt ttgcttgatc ccatcattag gcggaattgc   12180
cggtggtctg atttaccgcg cattgctggc gcgtccggct gaagcataaa actgagacaa   12240
tcatttaaag aggaaaggtg ttggagtgat ccggcgcctt tcttttttt atggcttttt    12300 ttggggatag gtcaggggat attggtcaga tacagaatgg atgtgtcagt cggcaaccta   12360
ggcatcgaca caaaaaaagg cggcataaat gccgcctgaa ttggctacag aatatcgtat   12420
aaacgatgtc tgtgatcaca aagataaaat agcatcaaca aaaaacggc aattcggtgt     12480 gtgttacgaa gccatgcaga cagcacttaa atgggcggta actgcatggc ttttttagct   12540
tatttgaacg ggtaagtaat ataaccgcgt tccattttt cttgttttac atcgtaatcg     12600
cttggtacgt cattcgcagc gatgaagccg tagaagatgt aacccagcag agtcaggatt   12660
gagccgtaga acacggcagt ctgaccacaa gcgtacacac cgtagatact gtagatggca   12720
gcgaaagcac ccaccacggc accaatcttc cattggctag cactgacgtg gtttttacgc   12780
agcataacaa acagaccagt ttgagacagt acgtatggca ccatgttgat gaacactgac   12840
aggttcagca gggtattgaa ctgttgtacg gtgttcggag aaatactcat ggttgccagc   12900
agcaactcca gcaccagcat gatcagcata ccggcgatag gtgcgttgta tttgttcatt   12960
ttgccgaaga tgcttgggaa cagcttcatt tgcgctgccg cccaagatac ttgcgcgtta   13020
gtgaactgcc aagccagcag agaaccgata caggcgatga tggccagagc acaaatcact   13080
tggcccacaa acggtgtgaa catcatgctg aataccagac cgaacggcgc actggatttc   13140
gccagttcag cgttaggcac gataccctga attacggtag ttgacgcgat gtacacgata   13200
gccacggaaa cggtcgccag cataacggcc agtggtacgg ttttttctgg gttacgaacg   13260
gcgccggagt tagcacctgc agtttcaatc cccaagaagg cccacagagt cagagcgata   13320
ccggaagaga tcccgtccat agtgccaacg tggtgtgggt tccagccggc ggcgaacagt   13380
tcaggtttga accagaacca accgatgatg gacagaccca ccacaggaat gatgatcccc   13440
catacagtta cgctggaaat accaccggtg tatttaggac cccagaagtt agctaccatg   13500
gtcaacacca gaacgcccac gacaccccag aaagcgtgta ctgcagattc agataaccat   13560
gggaagaaag gtttcatgta gccaaccgca gatacggcaa tcgccaccgc actgatgacc   13620
aagcaaatat aataggtata agacgcgatg aagaaggagg acttaccgtg cgcttcttgt   13680
gagtaggcag acataccgcc atcacggtga cagaacatac cgcattttgc gtaagtgtaa   13740
gcgatacaca gcgcacccac ggtagtgacc agccaggaga gcatggtaat accacctgta   13800
ccggcgaggt tagccggcag catgataata ccggagccca tcatgtttac tgttaccagc   13860
acagtgaggc ccataagccc cattttgtta tcatctgaag atgccataaa atttatctct   13920
ttattcgata aacttaatat ttattcatcc aaagtcacta aaatatgcac aggatgtgca   13980
taactgagga tgaggaaccc ttatttgttg ctgcagcgaa acccacacc aaggatgtta     14040 ataaatgaga taacggcgca ggaataatac cgttattgca tttatgtttt tgctgaaaat   14100
aaggccatta atgttgatgc gtgaataaac atttctggct cgatatacat cccgtatatg   14160
agttggttta ttttttaaca cagctgcata gggaagaaaa taaggtcga gaaaatcgga     14220 ttgtgccttg tgtcgcgtaa ttatttatga atttatgaat aatcagtaat cctgacgaaa   14280
agtcgttatt gtatgtaatc atctttaagt gtaatttcac gcaaccagat gtttctttcc   14340
```

```
ttgcgccgcc agcgctttgt tttatgtgtt gaaataatct tttctgtaac cgcgcgtaat    14400
ttatcctttc ctctctttat tttgtgtatt tcgttgtaca taagtggtgt ttatttatgc    14460
atgtcattta ttgatggttt attgctgcgt actgaatgaa gtgtaacttg gtagaaaaag    14520
aaggctgaat gtttattgcc tcctgtttca ggttatgaca atgaatgctc tatttgtaca    14580
gttaacttta cgtcatttga taatgtcatt tactgtgcca gcgtaatttt attaatggcg    14640
tgctgtcggg caatttggtt ttcggcgcct taataaaata ttccgcgatc aatatcacaa    14700
atagcatttt cattaggaaa ttaaatatca attttctgcg gataggctgg gcgcactatt    14760
gagcgataaa acgctgtgaa aatagcgatt ggcagcattg cgttgcctgt atttatctcg    14820
tttgccggat ttttatgcat ttgagtgcgc agccgccgtg ccgcccatac atgctctatc    14880
ttttactgtg gggtctcaca tattccaccg ttattacatg tgatggctat tactcgttgt    14940
gctggcgtgt tggcgagcgg atgcagagcg tggcaagcag agccggtcga c             14991
```

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence:putative
      promoter, -35 and -10 consensus sequence of AF294823
      (SEQ ID NO:7 positions 1645-1671)
<220> FEATURE:
<221> NAME/KEY: modified_base
<222> LOCATION: (7)..(21)
<223> OTHER INFORMATION: n = g, a, c or t

<400> SEQUENCE: 19
attaccnnnn nnnnnnnnnn ntatagt                                         27

<210> SEQ ID NO 20
<211> LENGTH: 14
<212> TYPE: DNA
<213> ORGANISM: Artificial Sequence
<220> FEATURE:
<223> OTHER INFORMATION: Description of Artificial Sequence:region of
      pWR102 plasmid upstream of wbgT gene containing left inverted
      repeat (IRL) of IS91

<400> SEQUENCE: 20
cctactcgat cagc                                                       14

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence:region of
      pWR101 plasmid downstream of wbgZ gene containing right inverted
      repeat (IRR) and target sequence of IS91

<400> SEQUENCE: 21
ggttgcgttc atcgatagg                                                  19

<210> SEQ ID NO 22
<211> LENGTH: 14
<212> TYPE: DNA
<213> ORGANISM: Artificial Sequence
<220> FEATURE:
<223> OTHER INFORMATION: Description of Artificial Sequence: a portion
      of the pWR101 cosmid downstream from gene wbgZ containing IRL of
      IS91 and target sequence.

-continued

```
<220> FEATURE:
<223> OTHER INFORMATION: Description of Artificial Sequence:region of
      pWR101 plasmid downstream of wbgZ gene containing left inverted
      repeat (IRL) of IS91

<400> SEQUENCE: 22
cctactcggg ggtt                                                    14
```